(12) United States Patent
Bergstrom et al.

(10) Patent No.: US 7,456,165 B2
(45) Date of Patent: Nov. 25, 2008

(54) HCV NS5B INHIBITORS

(75) Inventors: Carl P. Bergstrom, Madison, CT (US);
Scott W. Martin, Middletown, CT (US);
Thomas W. Hudyma, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/671,753

(22) Filed: Feb. 6, 2007

(65) Prior Publication Data

US 2007/0185083 A1     Aug. 9, 2007

Related U.S. Application Data

(60) Provisional application No. 60/771,391, filed on Feb. 8, 2006.

(51) Int. Cl.
*A61K 31/55* (2006.01)
*A61P 31/00* (2006.01)
*C07D 223/14* (2006.01)

(52) U.S. Cl. .................. 514/214.01; 540/576
(58) Field of Classification Search ............ 514/214.01; 540/576
See application file for complete search history.

(56) References Cited

U.S. PATENT DOCUMENTS

| 7,153,848 | B2 | 12/2006 | Hudyma et al. | 514/214.01 |
| 2006/0166964 | A1 | 7/2006 | Hudyma et al. | 514/211.09 |
| 2007/0060565 | A1 | 3/2007 | Meanwell et al. | 514/214.01 |
| 2007/0078122 | A1 | 4/2007 | Bergstrom et al. | 514/214.01 |
| 2007/0185083 | A1 | 8/2007 | Bergstrom et al. | 514/214.01 |

FOREIGN PATENT DOCUMENTS

| WO | WO2005/080399 | 9/2005 |
| WO | WO2006/040039 | 4/2006 |
| WO | WO2006/046030 | 5/2006 |
| WO | WO2007/029029 | 3/2007 |

OTHER PUBLICATIONS

U.S. Appl. No. 11/752,354, filed May 23, 2007, Robert G. Gentles, et al.
U.S. Appl. No. 11/753,137, filed May 24, 2007, Carl P. Bergstrom.
U.S. Appl. No. 11/756,203, filed May 31, 2007, Kap-Sun Yeung, et al.

*Primary Examiner*—Brenda L Coleman
(74) *Attorney, Agent, or Firm*—James Epperson

(57) ABSTRACT

The invention encompasses compounds of Formula I as well as compositions and methods of using the compounds. The compounds have activity against hepatitis C virus (HCV) and are useful in treating those infected with HCV.

8 Claims, No Drawings

HCV NS5B INHIBITORS

CROSS REFERENCE TO RELATED APPLICATIONS

This application claims the benefit of U.S. Provisional Application Ser. No. 60/771,391 filed Feb. 8, 2006.

BACKGROUND OF THE INVENTION

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

DESCRIPTION OF THE INVENTION

The invention encompasses compounds and pharmaceutically acceptable salts of formula I, and compositions and methods of treatment using these compounds.

One aspect of the invention is a compound of formula I

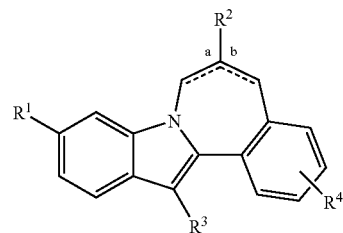

wherein:

$R^1$ is $CO_2R^5$ or $CONR^6R^7$;

$R^2$ is furanyl, pyrrolyl, thienyl, pyrazolyl, oxazolyl, thiazolyl, isoxazolyl, isothiazolyl, oxadiazolyl, triazolyl, or tetrazolyl, and is substituted with 0-2 substituents selected from oxo, amino, alkylamino, dialkylamino, alkyl, (cycloalkyl)alkyl, hydroxyalkyl, (tetrahydrofuranyl)alkyl, (tetrahydropyranyl)alkyl, $(CO_2R^5)$alkyl, $(CON(R^5)_2)$alkyl, $(COR^9)$alkyl, (alkylsulfonyl)alkyl, and $((R^9)$alkyl$)CON(R^5)$;

$R^3$ is $C_{5-7}$cycloalkyl;

$R^4$ is hydrogen, halo, hydroxy, alkyl, or alkoxy;

$R^5$ is hydrogen, alkyl, or cycloalkyl;

$R^6$ is hydrogen, alkyl, cycloalkyl, alkoxy, or $SO_2R^8$;

$R^7$ is hydrogen, alkyl, or cycloalkyl;

or $NR^6R^7$ taken together is pyrrolidinyl, piperidinyl, piperazinyl, N-alkylpiperazinyl, homomorpholinyl, homopiperidinyl, morpholinyl, or thiomorpholinyl;

$R^8$ is alkyl, haloalkyl, cycloalkyl, amino, alkylamino, dialkylamino, or phenyl;

or $R^8$ is pyrrolidinyl, piperidinyl, piperazinyl, N-alkylpiperazinyl, homomorpholinyl, homopiperidinyl, morpholinyl, or thiomorpholinyl;

$R^9$ is pyrrolidinyl, piperidinyl, piperazinyl, N-alkylpiperazinyl, homomorpholinyl, homopiperidinyl, morpholinyl, or thiomorpholinyl; and (a) is a single bond or a double bond, (b) is a single bond or a double bond, provided that at least one of (a) and (b) is a single bond;

or a pharmaceutically acceptable salt thereof.

Another aspect of the invention is a compound of formula I selected from the group consisting of

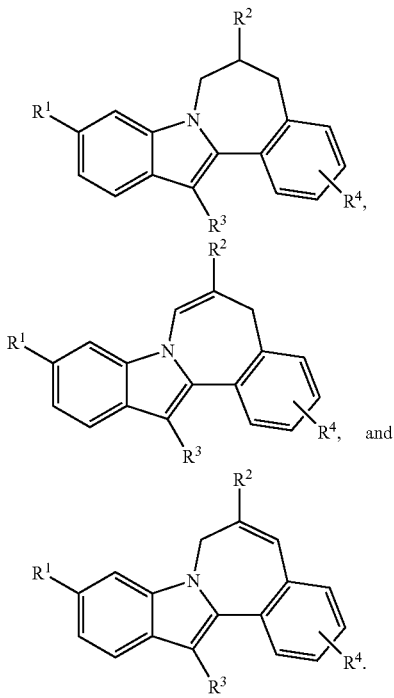

and

Another aspect of the invention is a compound of formula I where $R^1$ is $CONR^6R^7$; $R^6$ is $SO_2R^8$; and $R^7$ is hydrogen.

Another aspect of the invention is a compound of formula I where $R^3$ is cyclohexyl.

Another aspect of the invention is a compound of formula I where $R^4$ is hydrogen.

Another aspect of the invention is a compound of formula I where $R^4$ is methoxy.

For a compound of Formula I, any scope of $R^1$, $R^2$, $R^3$, $R^4$, $R^5$, $R^6$, $R^7$, $R^8$, $R^9$, (a), and (b) can be used independently with the scope of any other variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods known in the art.

Synthetic Methods

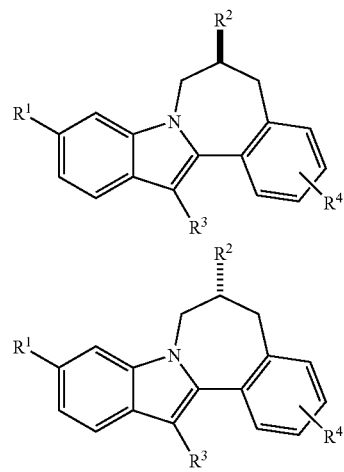

Formula I compounds may be made by methods known in the art including those described below. Some reagents and intermediates are known in the art. Other reagents and intermediates can be made by methods known in the art using readily available materials. The variables (e.g. numbered "R" substituents) used to describe the synthesis of formula I compounds are intended only to illustrate how to make and are not to be confused with variables used in the claims or in other sections of the specification. Abbreviations used within the schemes generally follow conventions used in the art.

Abbreviations used within the schemes generally follow conventions used in the art. Some examples are as follows: THF means tetrahydrofuran; DMF means N,N-dimethylformamide; RCM means ring-closing methasis; Boc means tert-butoxycarbonyl; TFA means trifluoracetic acid; DMA means N,N-dimethylacetamide; $PPh_3$ means triphenylphosphine; OAc means acetate; Me means methyl; COD (or cod) means 1,5-cyclooctadiene; dtbpy means 4,4'-di-tert-butyl-2,2'-bipyridine; dba means dibenzylideneacetone; Xantphos means 4,5-bis(diphenylphosphino)-9,9-dimethylxanthine; aq means aqueous; EtOH means ethanol; MeOH means methanol; TBTU means 2-(1H-benzotriazole-1-yl)-1,1,3,3-tetramethyluronium tetrafluroborate; DMSO means dimethylsulfoxide; HATU means O-(7-azabenzotriazol-1-yl)-N,N,N',N'-tetramethyluronium hexafluorophosphate; EEDQ means 2-ethoxy-1-ethoxycarbonyl-1,2-dihydroquinoline; WSC means 1-[3-(dimethylamino)propyl]-3-ethylcarbodiimide hydrochloride; DMAP means 4-dimethylaminopyridine; n-Bu means n-butyl; BEMP means 2-tert-butylimino-2-diethylamino-1,3-dimethylperhydro-1,3,2-diazaphosphorine, polymer-bound; DIPEA means diisopropylethylamine; and TEA means triethylamine.
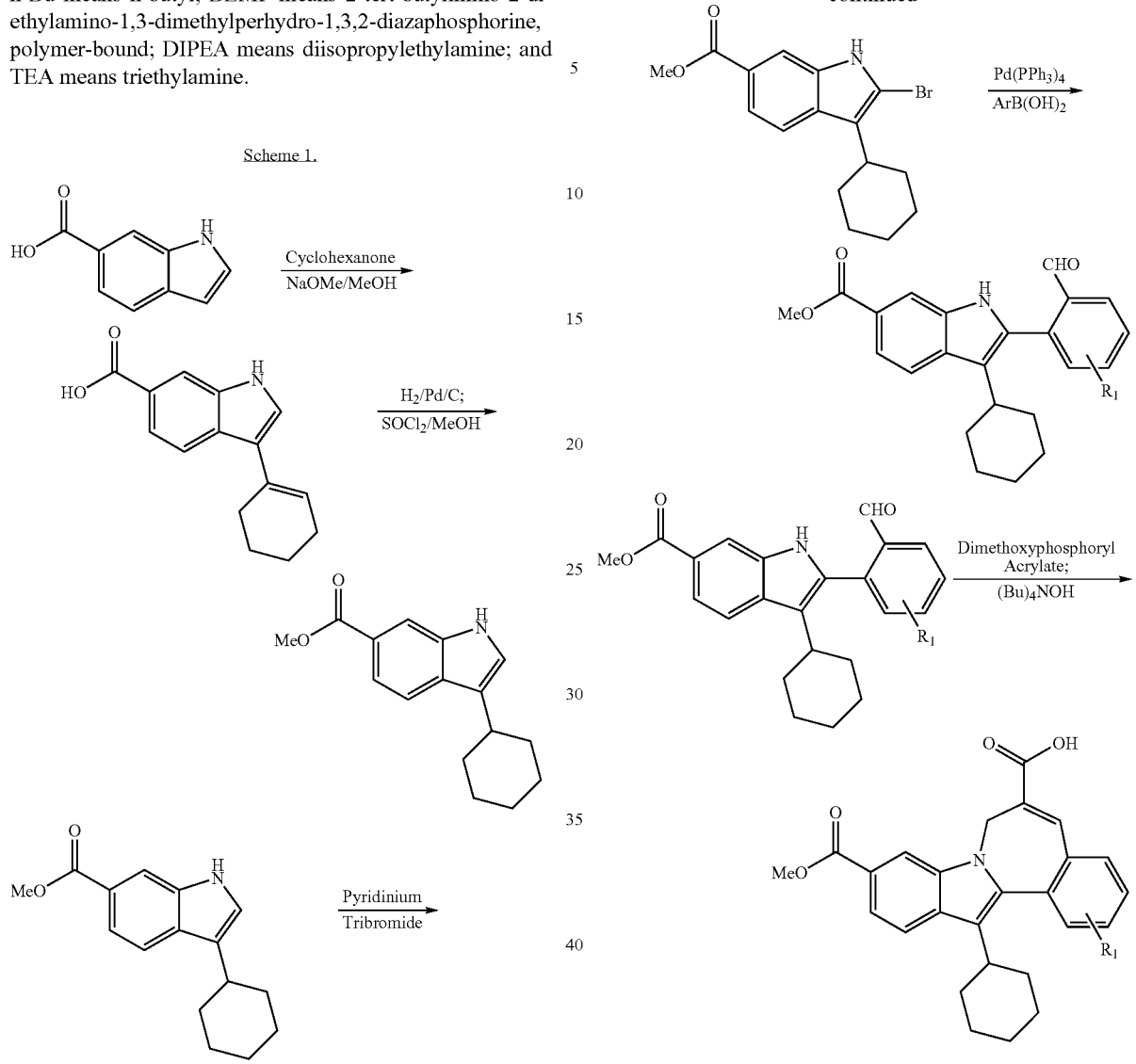
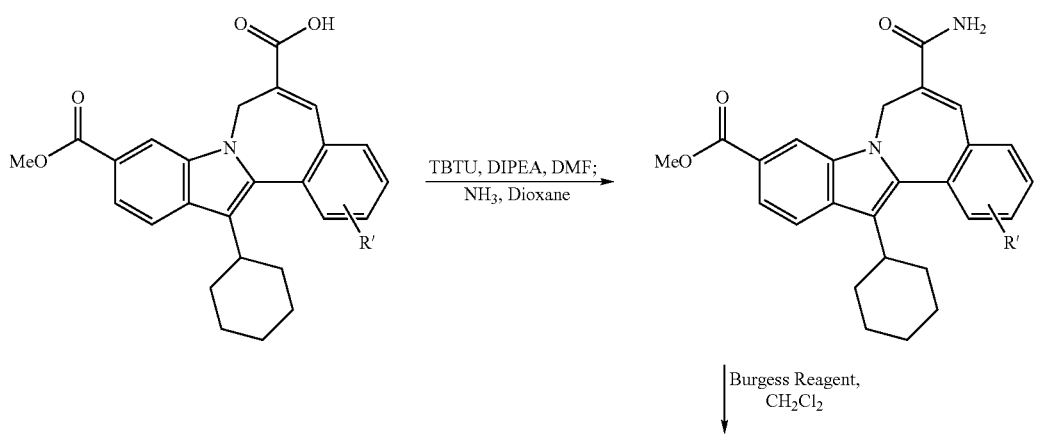

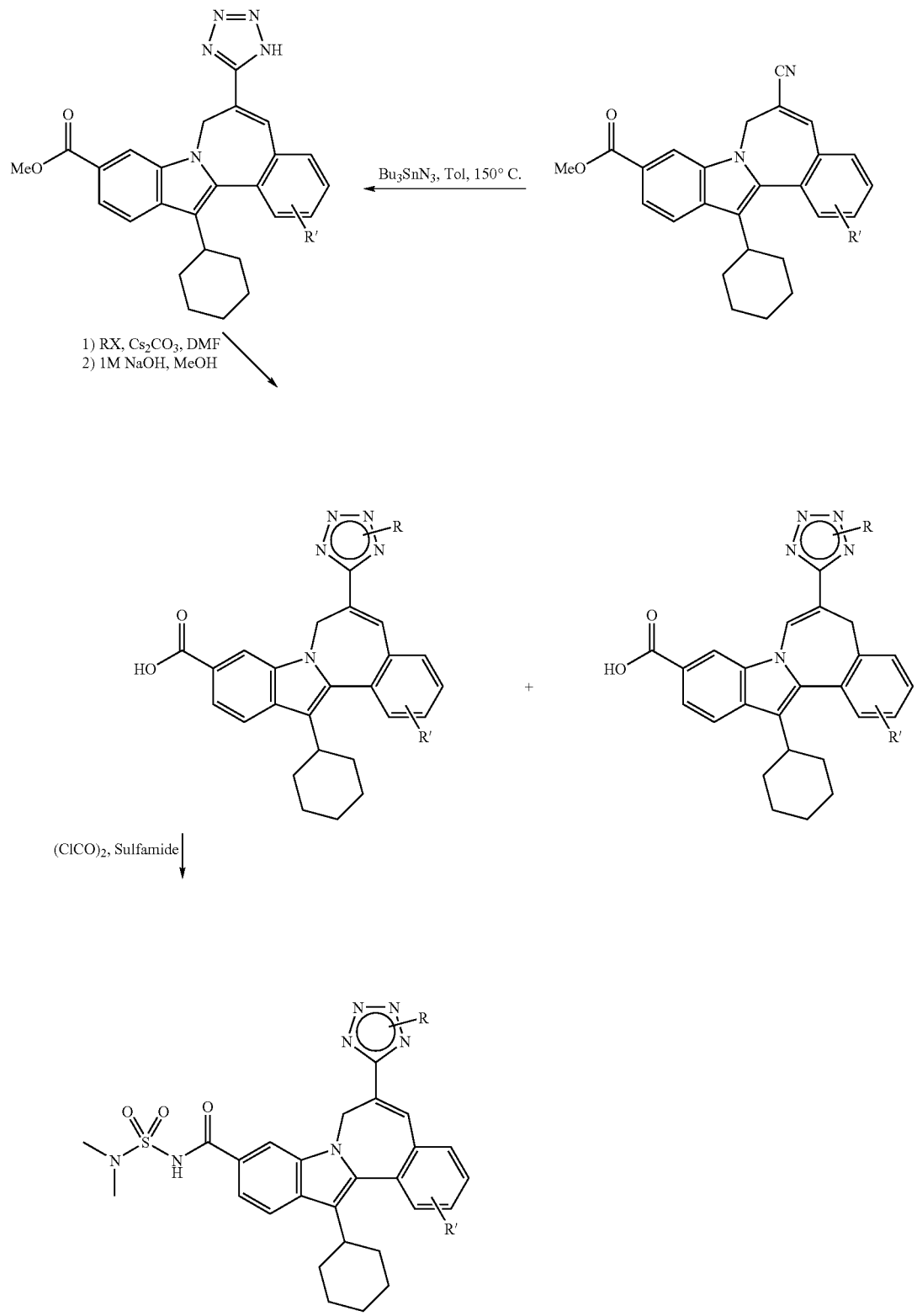

Scheme 3.
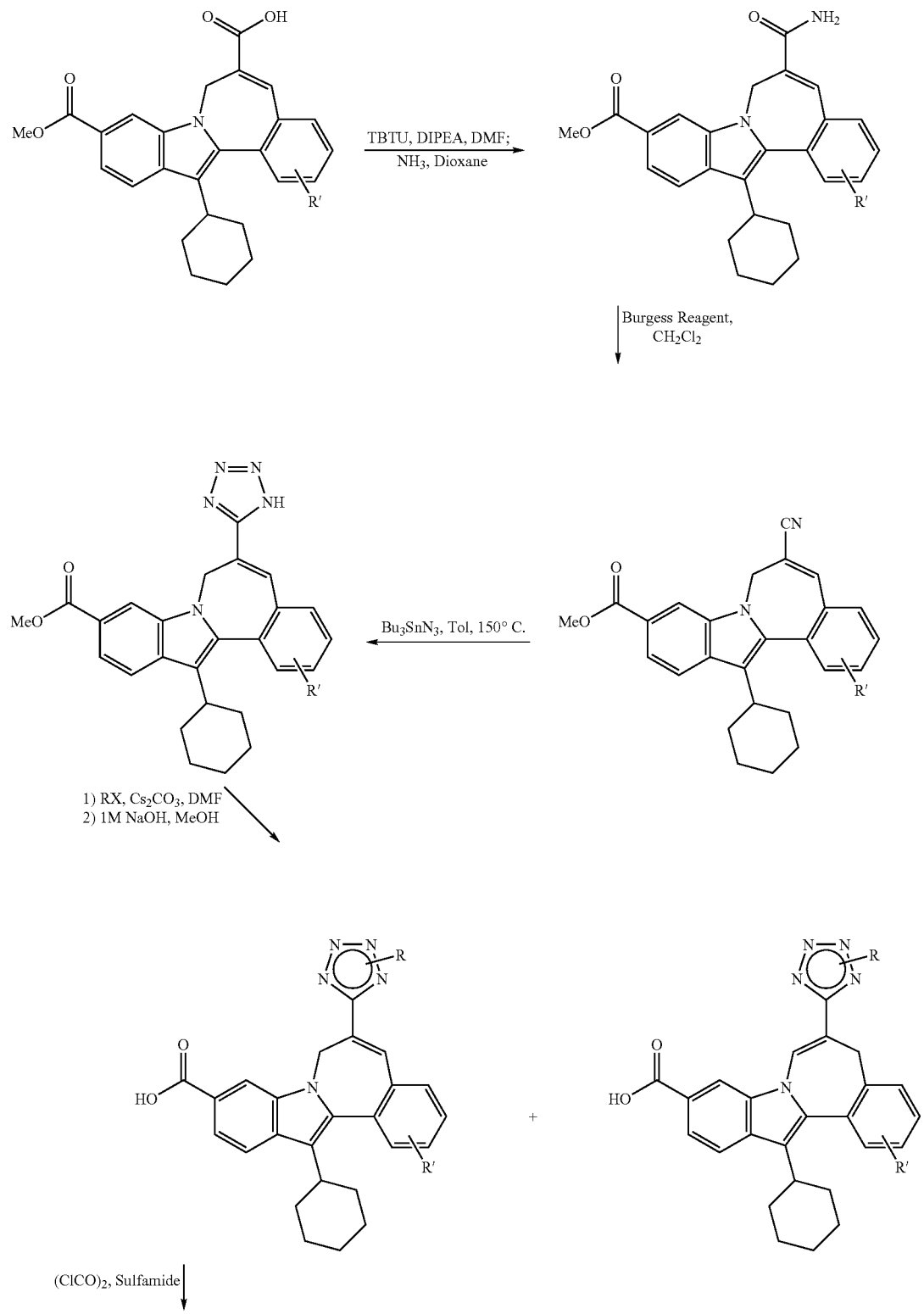

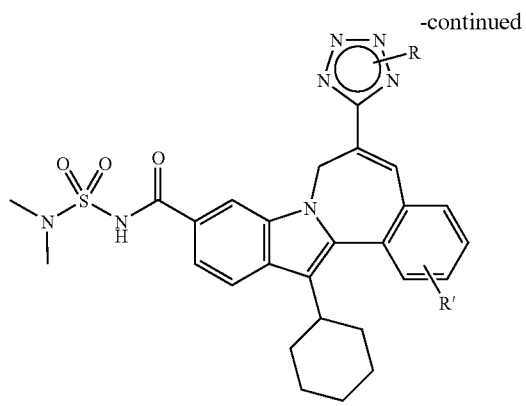
Scheme 4.
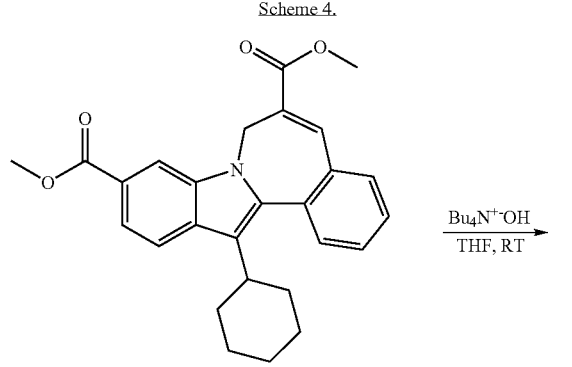
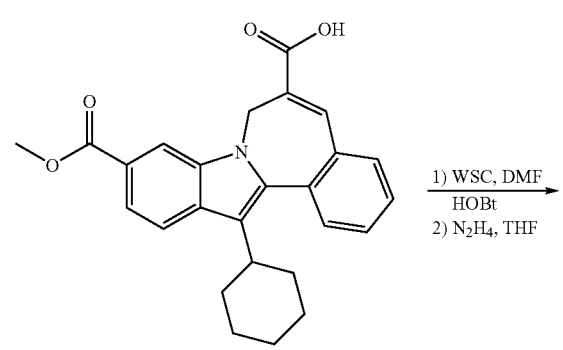
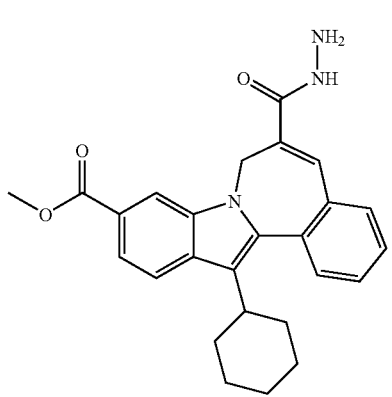
Scheme 5.
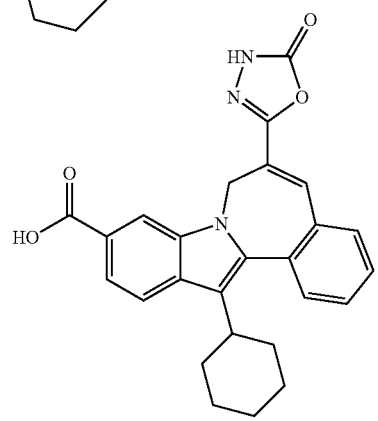

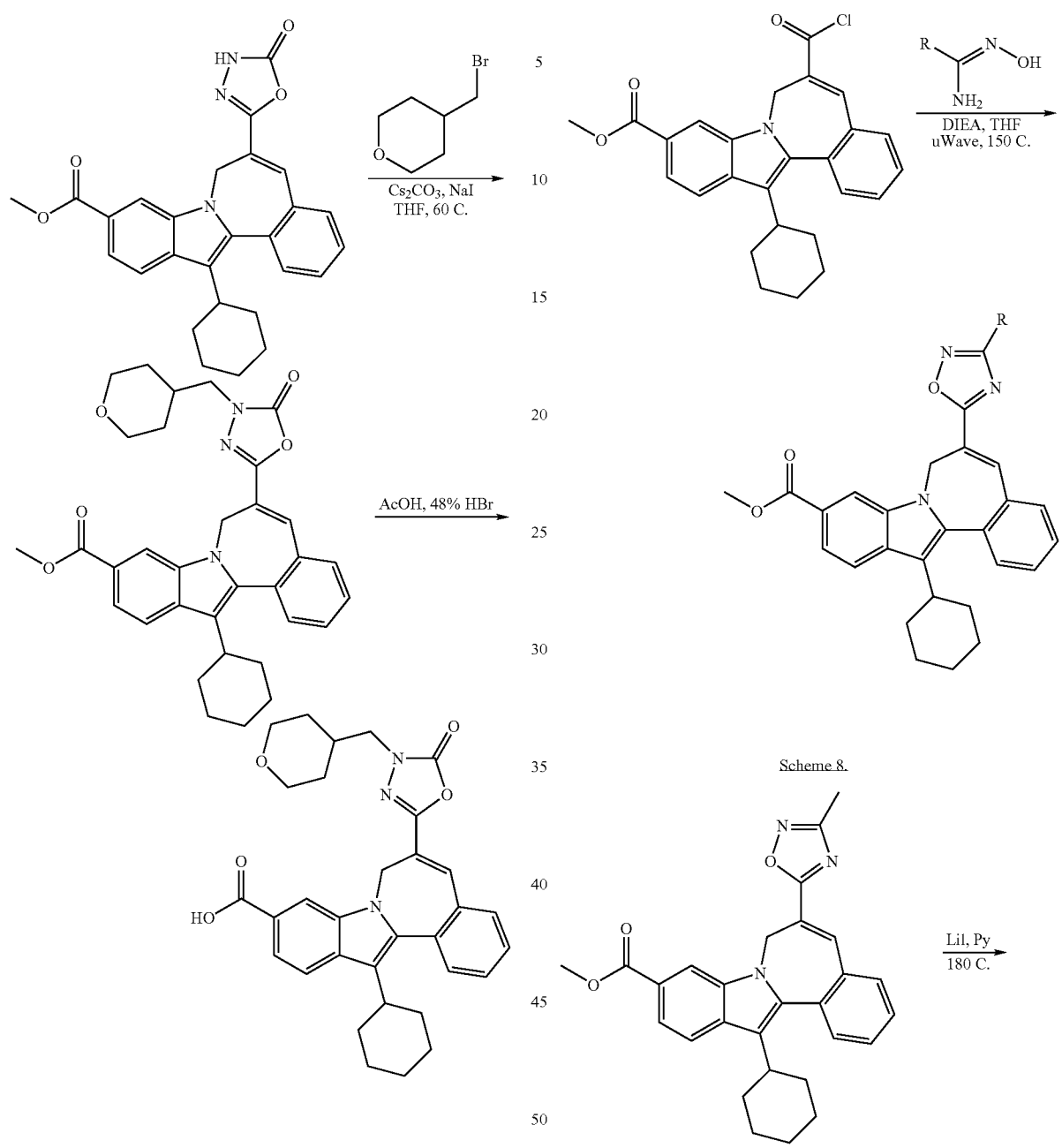
Scheme 6.
Scheme 7.
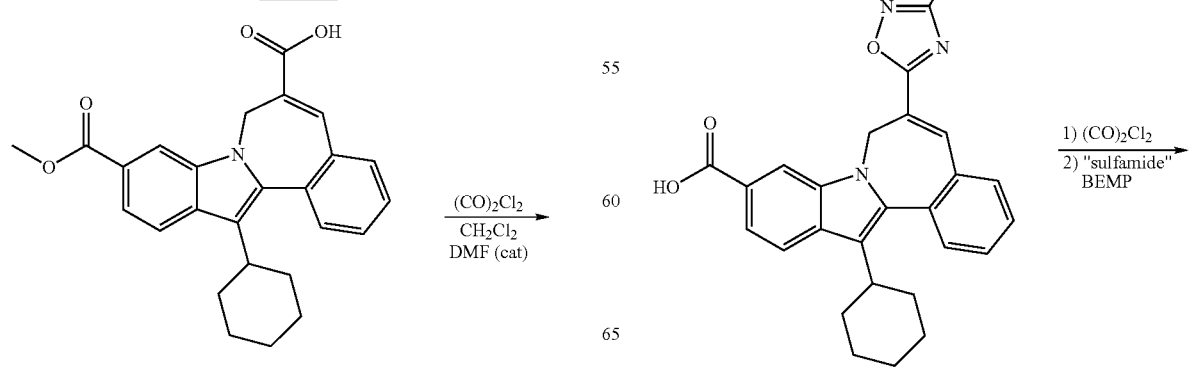
Scheme 8.
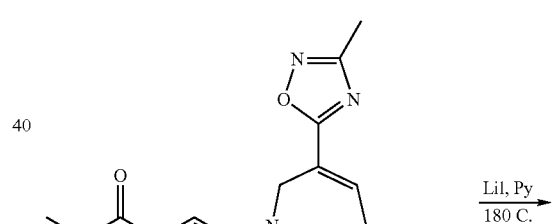

-continued
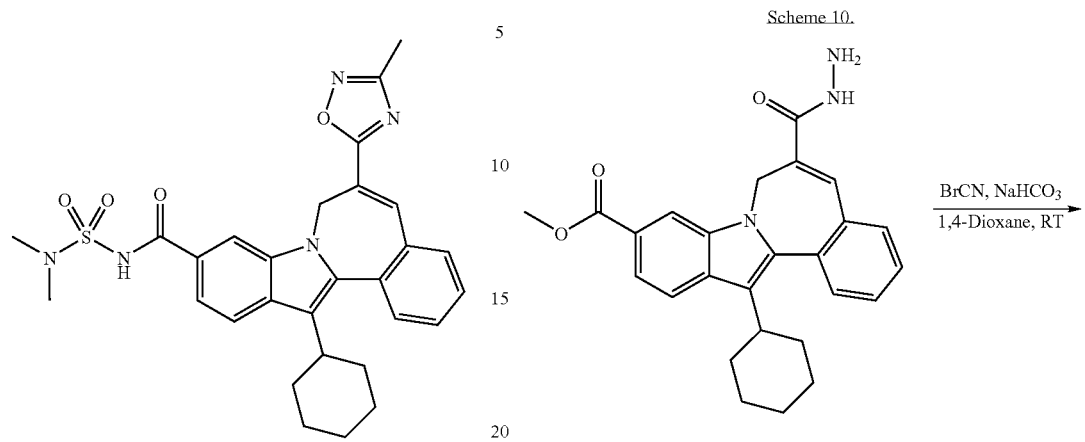
Scheme 9.
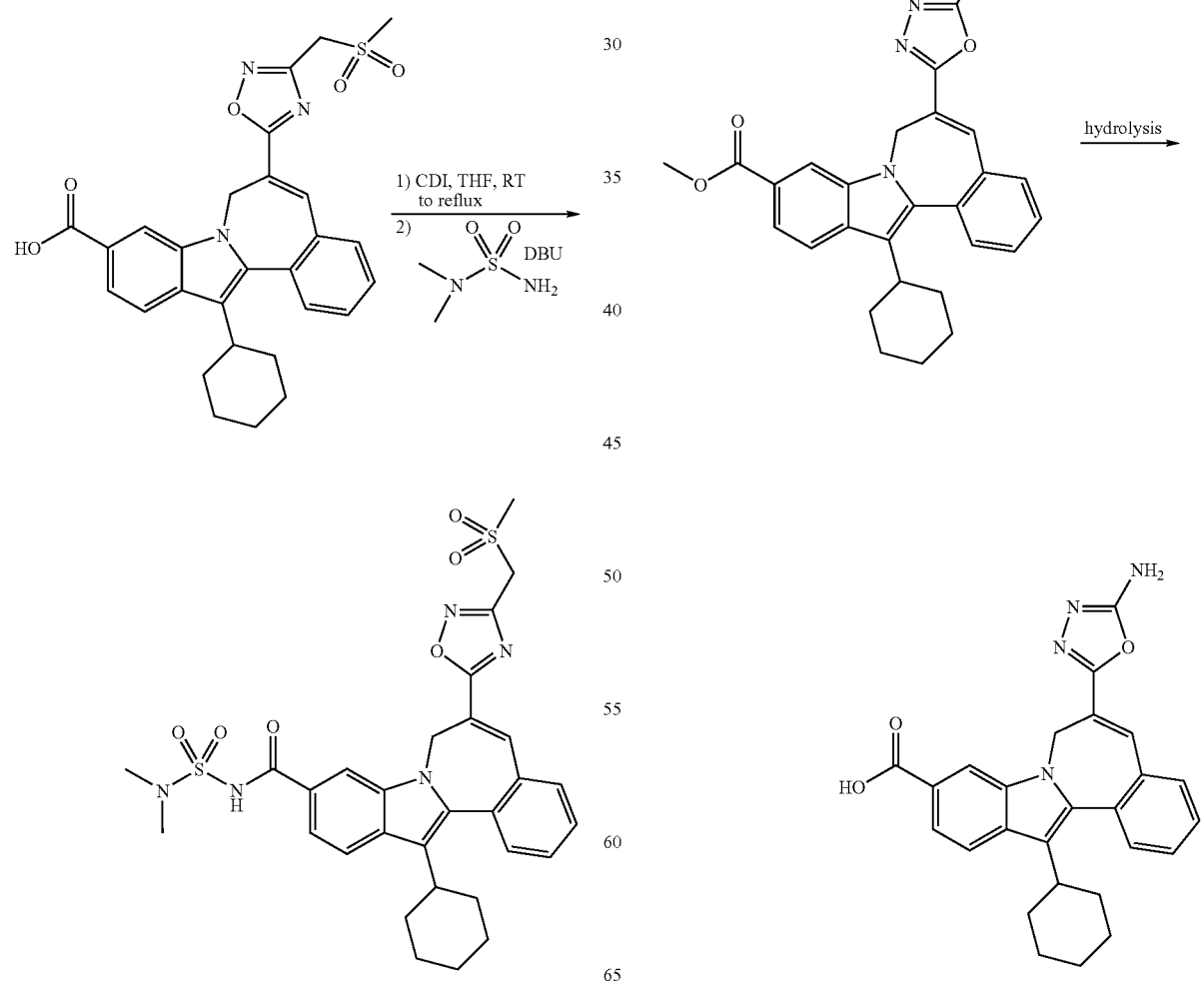

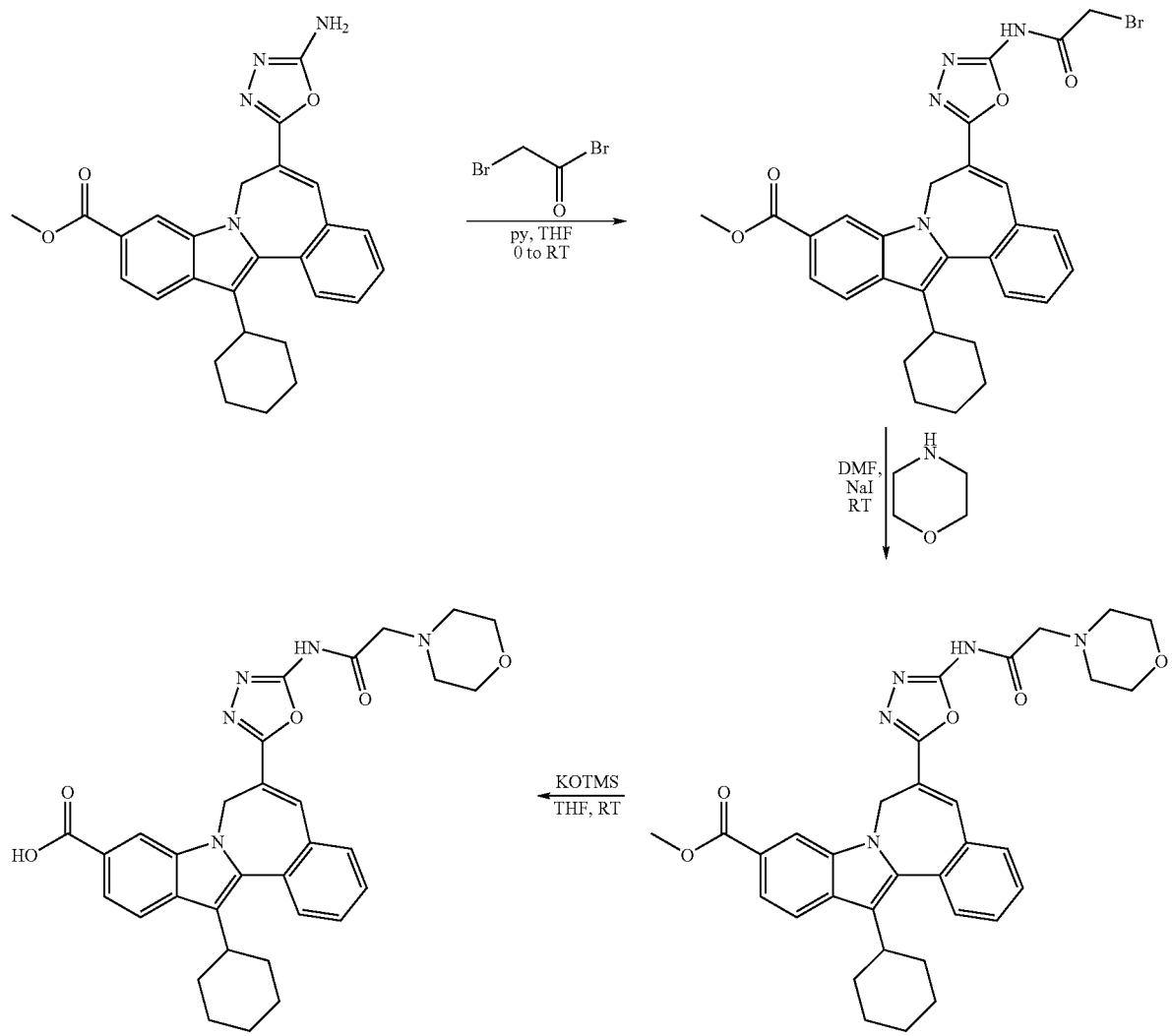
Scheme 11.
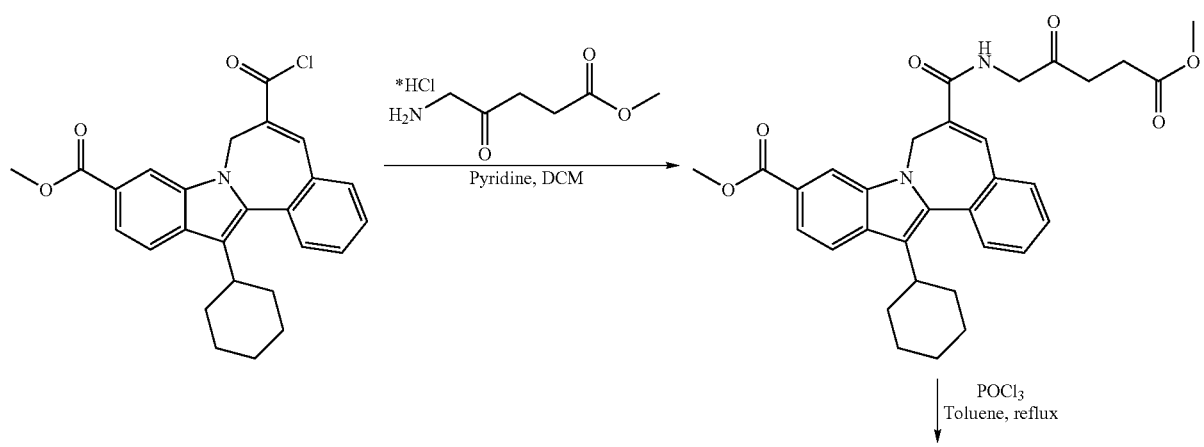
Scheme 12.

-continued
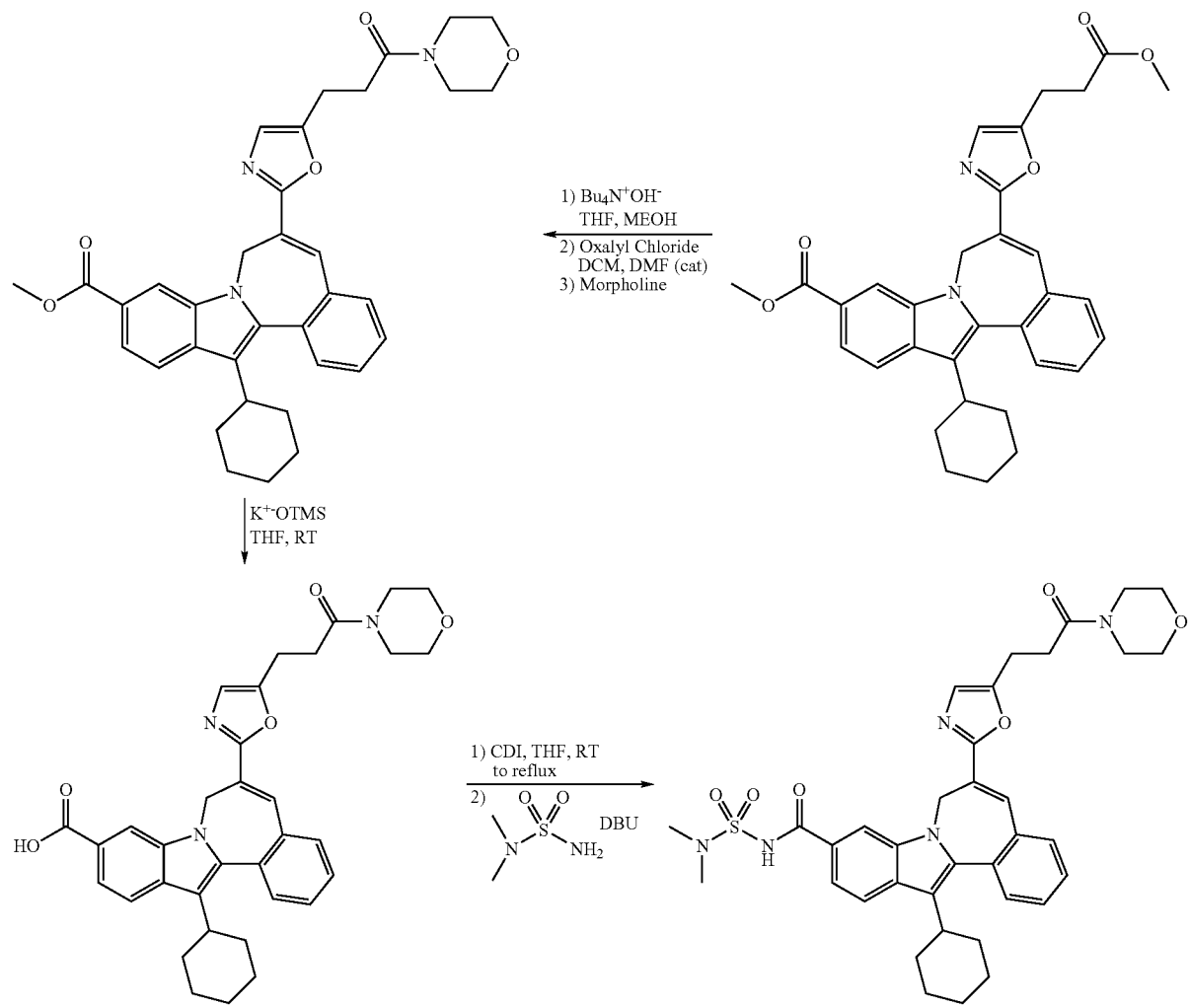
Scheme 13.
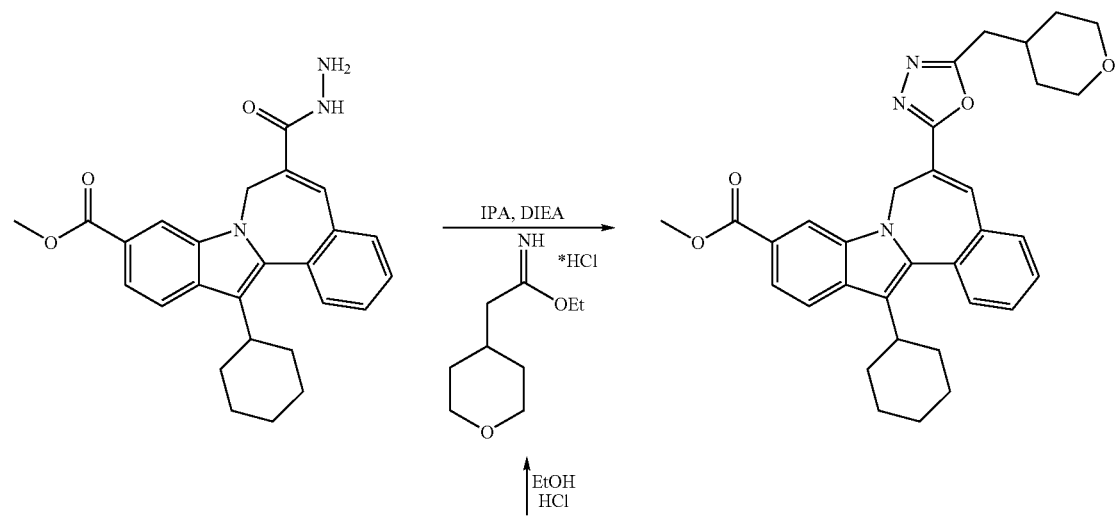

-continued
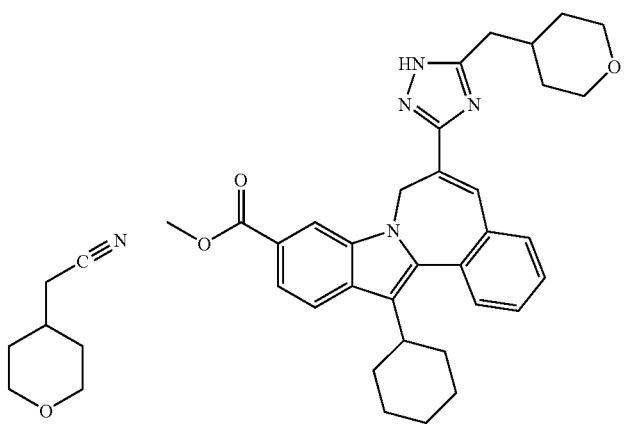
Scheme 14.
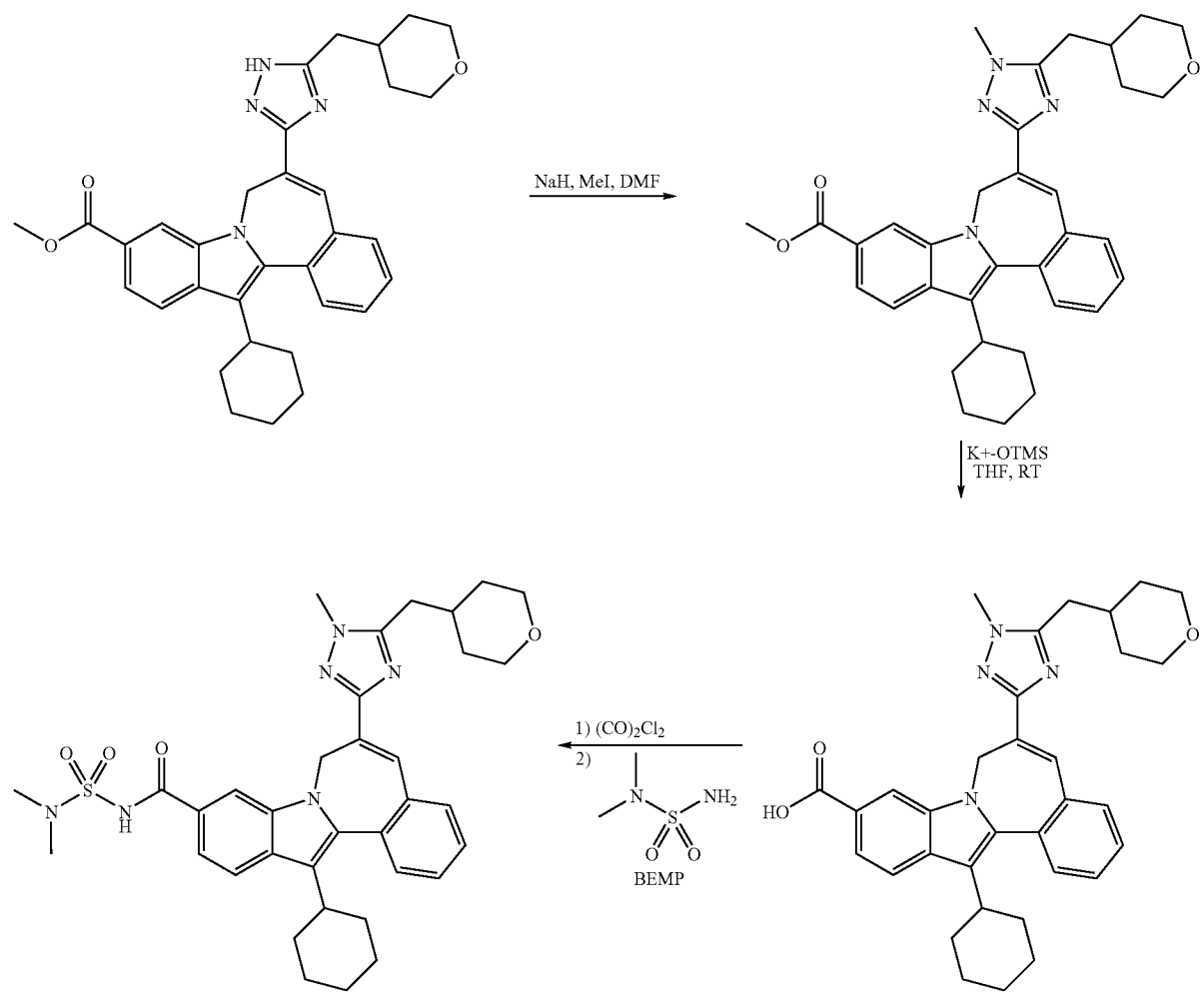

Scheme 15.

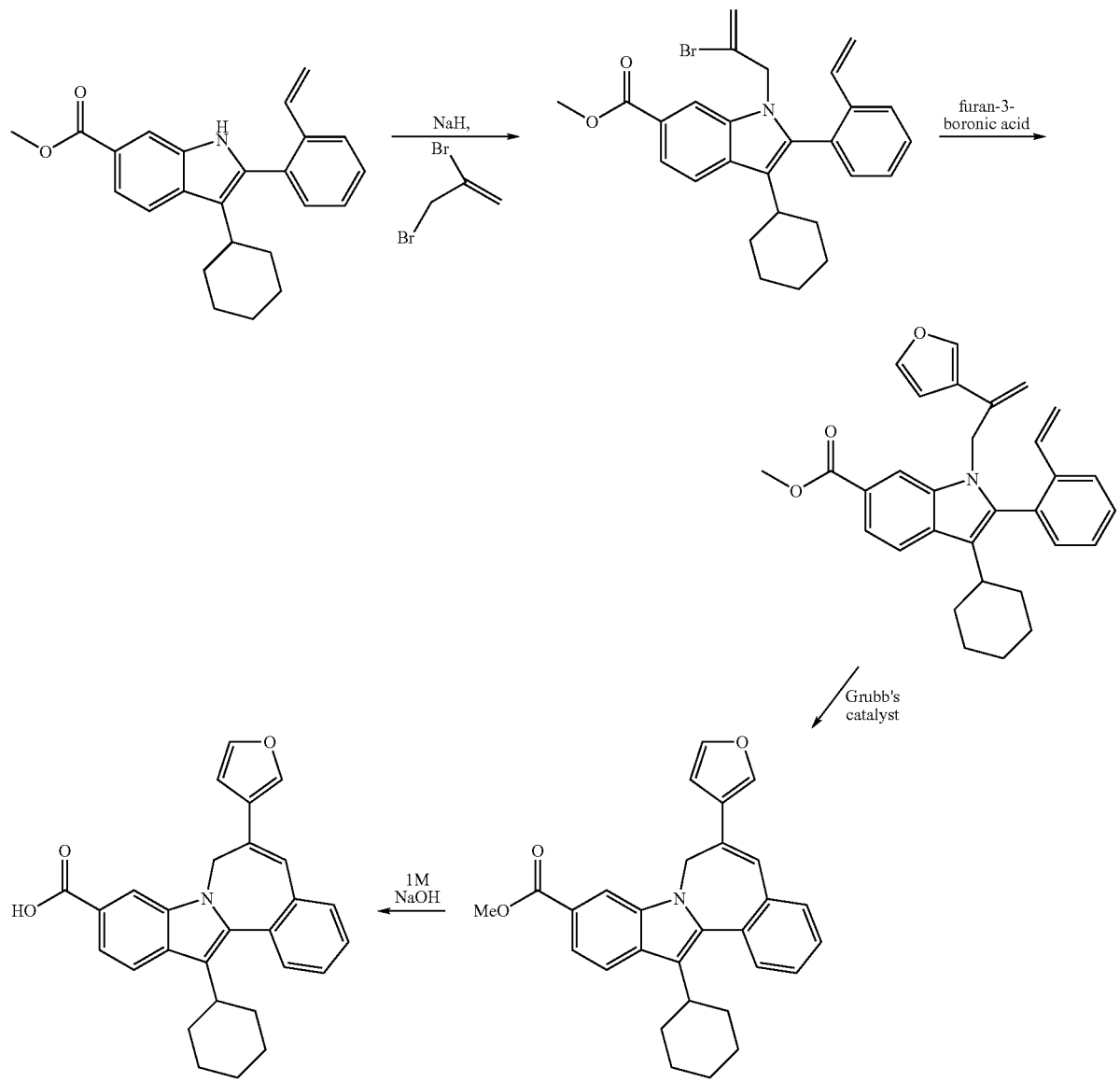

Biological Methods

The compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/ml and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 μm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 µl in 96 well plates (Costar 3912 H. The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 µCi (0.29 µM total UTP). Reactions were initiated by the addition of enzyme, incubated at 30° C. for 60 min, and stopped by adding 25 µl of 50 mM EDTA containing SPA beads (4 µg/µl, Amersham RPNQ 0007 H. Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 µg/µl beads. Order of addition in the assay: enzyme (14 nM) was added to diluted compound followed by the addition of a mixture of template (0.2 nM), 3H-UTP (0.6 µCi, 0.29 µM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)^{\wedge}D)))$.

FRET Assay Preparation. To perform the HCV FRET screening assay, 96-well cell culture plates were used. The FRET peptide (Anaspec, Inc.) (Taliani et al., *Anal Biochem.* 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with dH$_2$O, NaCl added to 150 mM final, the FRET peptide diluted to 20 µM final from a 2 mM stock.

To prepare plates, HCV replicon cells, with or without a *Renilla luciferase* reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a CO$_2$ incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity. The two numbers generated for the compound plate, percent cytotoxicity and percent activity were used to determine compounds of interest for further analysis.

Representative data for Formula I compounds are reported in Table 1.

TABLE 1

| Example | $IC_{50}$ | $EC_{50}$ |
|---|---|---|
| 1 | A | A |
| 2 | B | A |
| 3 | B | A |
| 4 | B | A |
| 5 | A | A |
| 6 | A | A |
| 7 | A | A |
| 8 | B | A |
| 9 | A | A |
| 10 | B | A |
| 11 | B | A |
| 12 | A | A |
| 13 | B | A |
| 14 | A | A |
| 15 | B | A |
| 16 | B | A |
| 17 | B | B |
| 18 | — | — |
| 19 | B | A |
| 20 | — | — |
| 21 | B | A |
| 22 | B | A |
| 23 | A | A |
| 24 | B | A |
| 25 | B | B |
| 26 | A | A |
| 27 | B | A |
| 28 | B | A |
| 29 | — | — |

TABLE 1-continued

| Example | IC$_{50}$ | EC$_{50}$ |
| --- | --- | --- |
| 30 | A | A |
| 31 | — | — |
| 32 | — | — |
| 33 | B | A |
| 34 | — | — |
| 35 | A | A |
| 36 | B | A |
| 37 | B | B |
| 38 | B | B |
| 39 | A | A |
| 40 | A | A |
| 41 | A | A |
| 42 | A | A |
| 43 | B | A |
| 44 | B | A |
| 45 | B | A |
| 46 | A | A |
| 47 | B | A |
| 48 | A | A |
| 49 | A | — |
| 50 | B | B |
| 51 | B | A |
| 52 | B | B |
| 53 | B | B |
| 54 | B | B |
| 55 | A | — |
| 56 | B | A |
| 57 | B | B |
| 58 | B | B |

A >0.5 μM;
B 0.001 μM-0.5 μM;
C <0.02 μM but an exact value was not determined;
IC$_{50}$ values were determined using the preincubation protocol.
EC50 values were determined using the FRET assay.

Additionally, compounds disclosed in U.S. patent application Ser. No. 11/181,639, filed Jul. 14, 2005 were shown to have activity in these assays (see Table 2).

TABLE 2

Structure

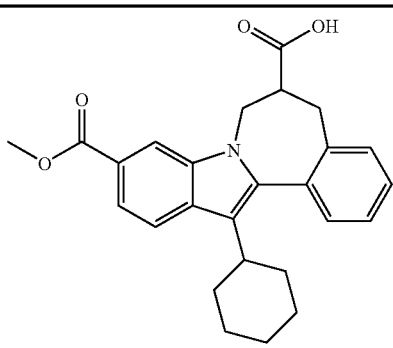

TABLE 2-continued

Structure

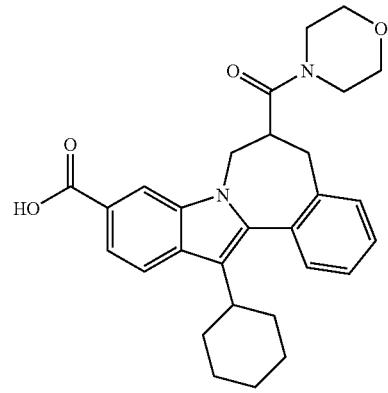

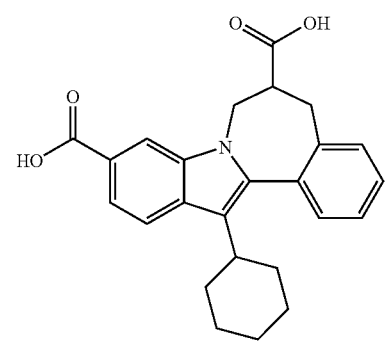

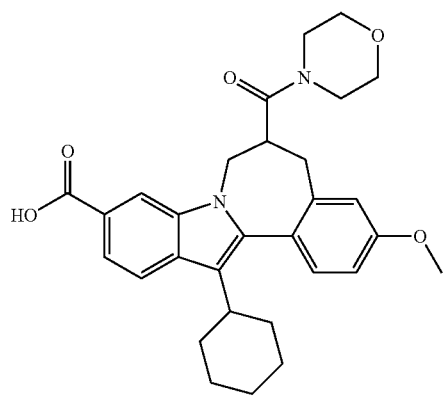

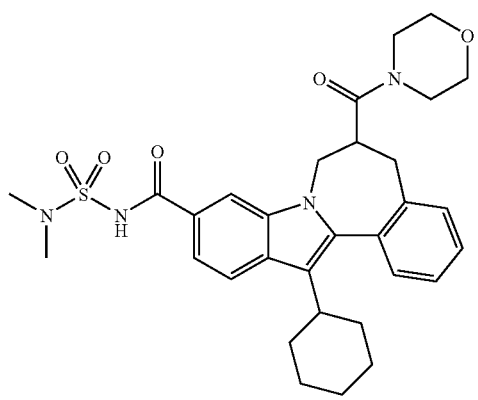

TABLE 2-continued
Structure
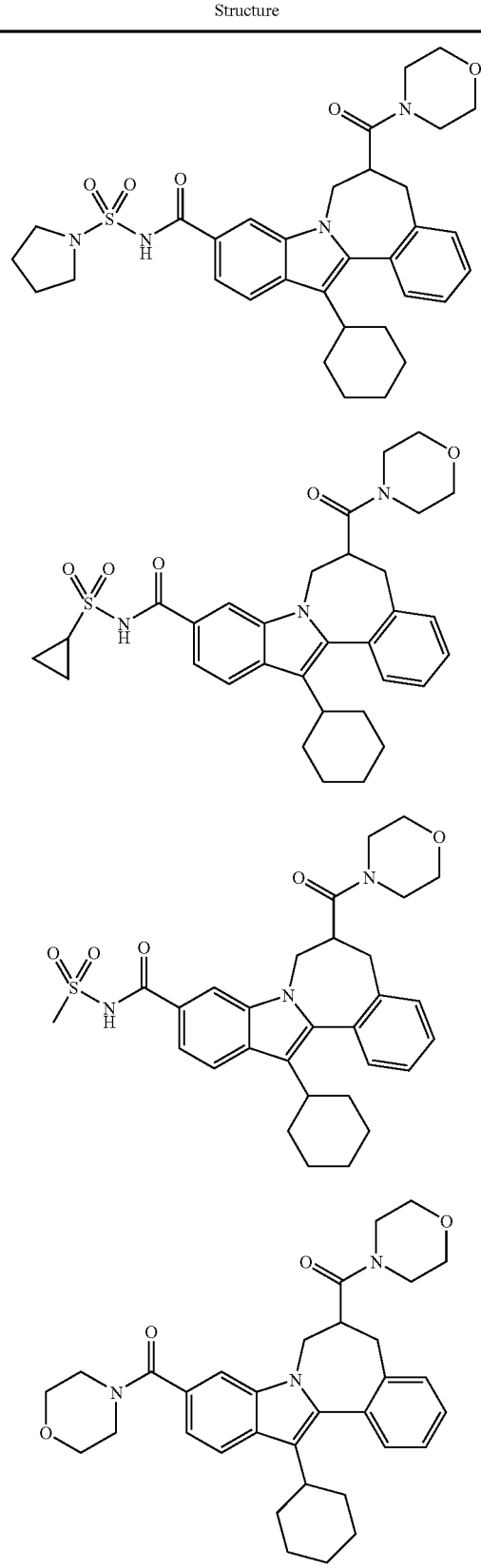
TABLE 2-continued
Structure
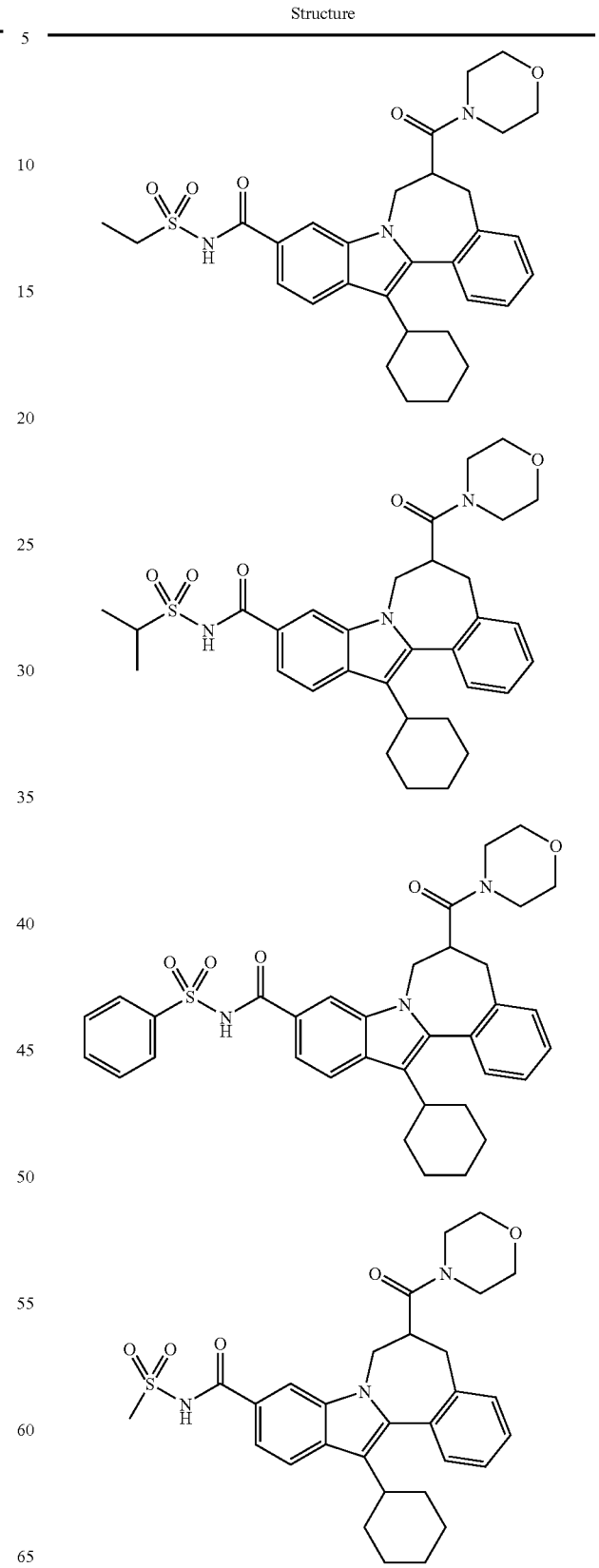

TABLE 2-continued
Structure
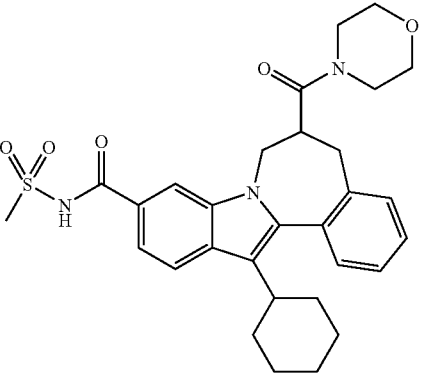
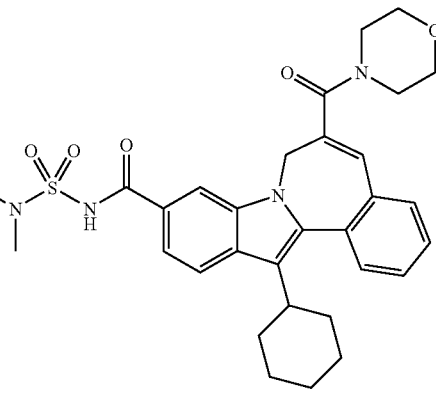
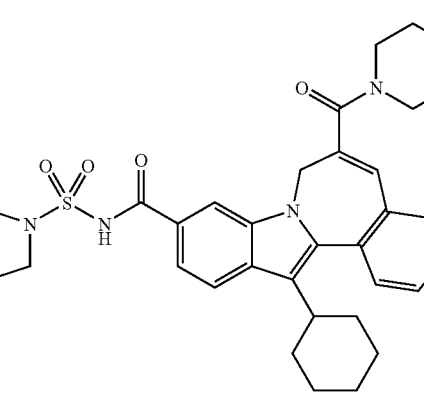
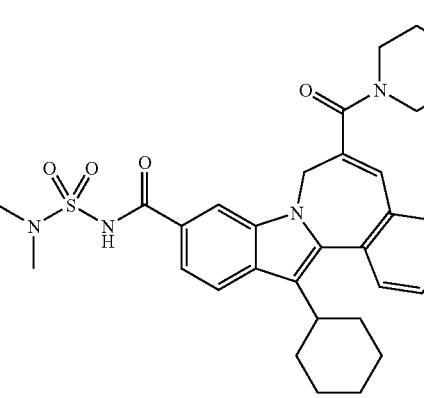
TABLE 2-continued
Structure
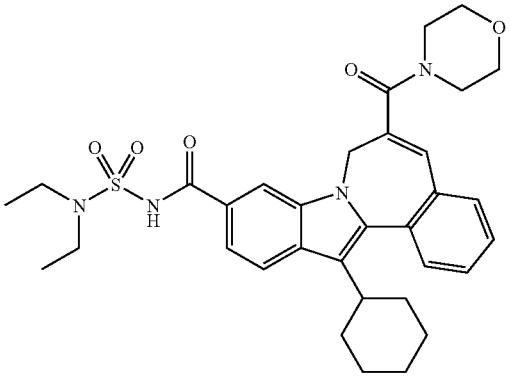
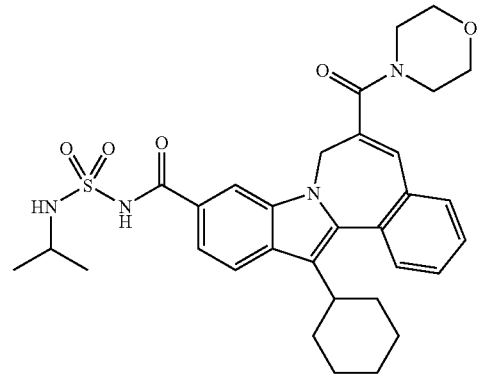
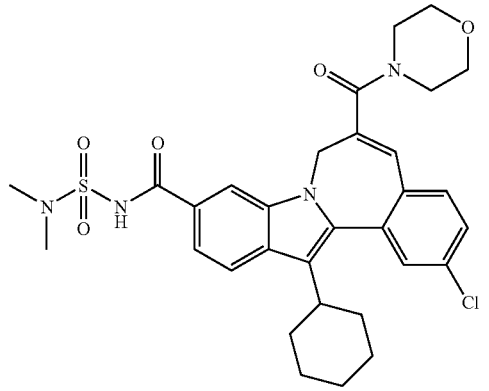
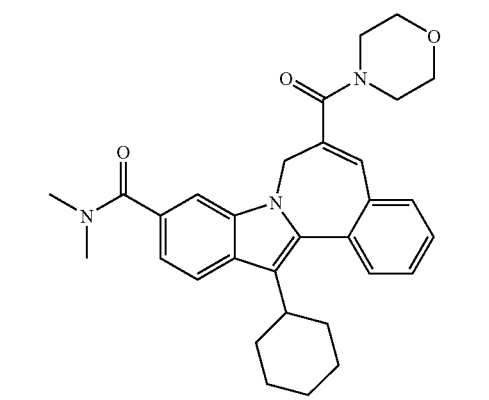

TABLE 2-continued
Structure
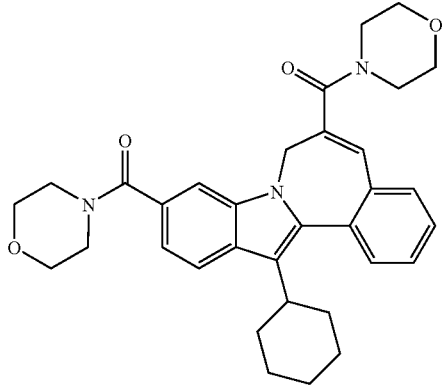
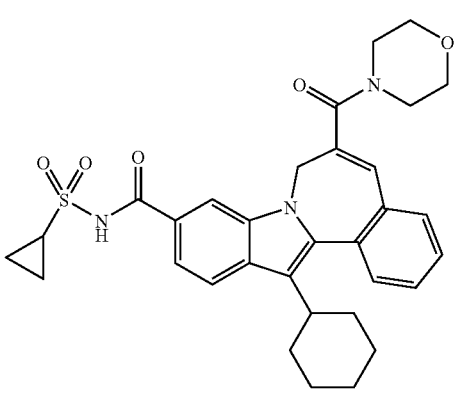
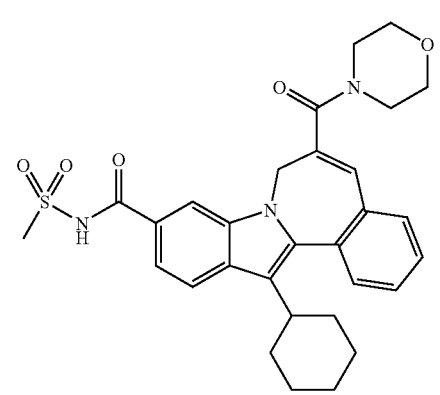
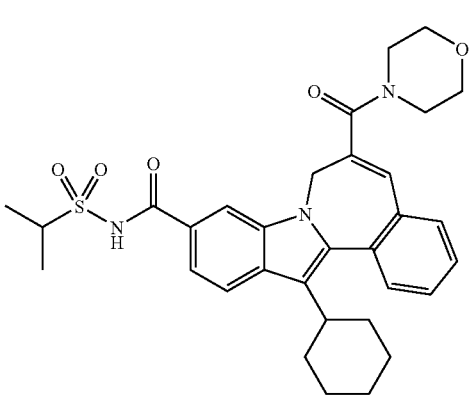
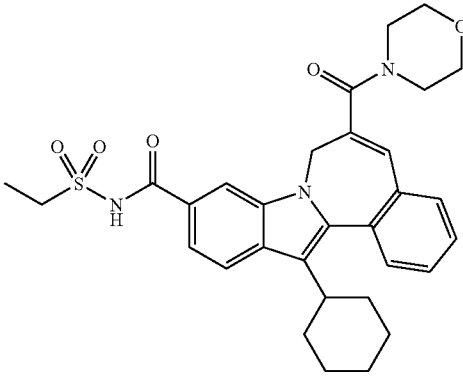
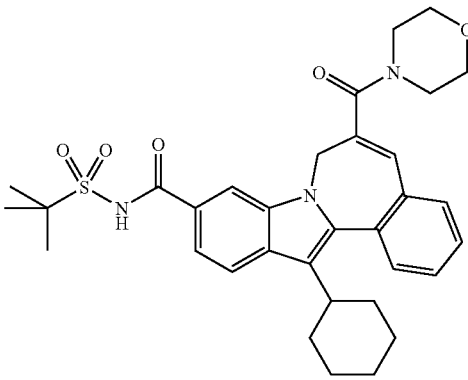
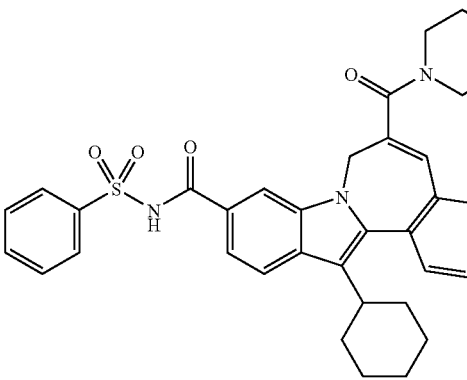
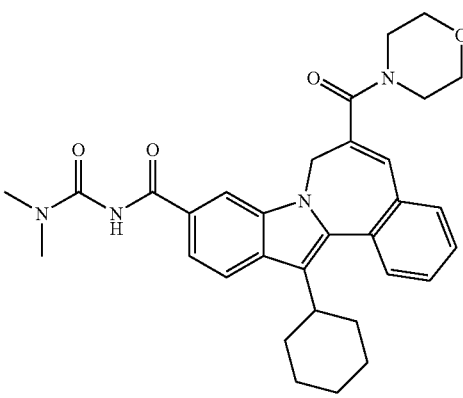

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound of formula I or a pharmaceutically acceptable salt thereof.

Another aspect of the invention is a method of inhibiting the function of the HCV NS5B protein comprising contacting the HCV NS5B protein with a compound of formula I or a pharmaceutically acceptable salt thereof.

Another aspect of the invention is a method of treating an HCV infection in a patient comprising administering to the patient a therapeutically effective amount of a compound or a pharmaceutically acceptable salt thereof. Another aspect of the invention is a method of inhibiting the function of the HCV replicon. Another aspect of the invention is a method of inhibiting the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgment.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
| --- | --- | --- |
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon - α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/ SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |

TABLE 2-continued

| Brand Name | Type of Inhibitor or Target | Source Company |
| --- | --- | --- |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | Immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO 2005047288 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

DESCRIPTION OF SPECIFIC EMBODIMENTS

Analytical HPLC and LC/MS were performed by using Shimadzu-VP instrument with UV detection at 220 nM and Waters Micromass. NMR spectra were collected by using Bucker DPX-300 MHz or DRX-500 MHz instruments.

Intermediate 1

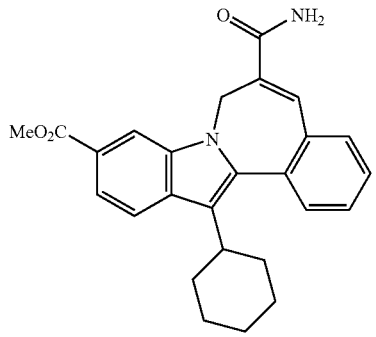

Intermediate 3

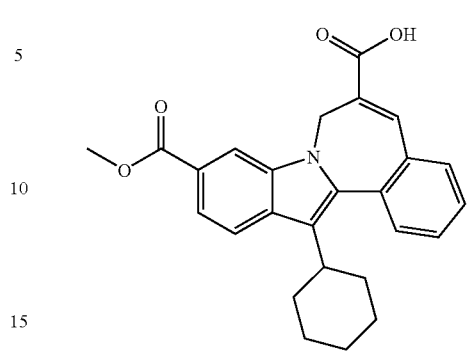

6-(aminocarbonyl)-13-cyclohexyl-7H-indolo[2,1-a][2]benzazepine-10-carboxylic acid, methyl ester. To a solution of 7H-indolo[2,1-a][2]benzazepine-6,10-dicarboxylic acid, 13-cyclohexyl-, 10-methyl ester (1.10 g, 2.65 mmol) in DMF (7.0 mL) and DIPEA (1.85 mL, 10.6 mmol) was added TBTU (1.28 g, 3.97 mmol). The resulting solution was stirred at 22° C. for 15 min. Ammonia (0.5M in dioxane, 21.2 mL, 10.6 mmol) was added and this solution was stirred at 22° C. for 18 hr. 1M HCl (50 mL) was added and the aqueous layer was extracted with CHCl$_3$ (2×50 mL). The organic phase was dried over Na$_2$SO$_4$, filtered, and concentrated under reduced pressure. Silica gel chromatography (4:1 EtOAc:hexanes) of the concentrate afforded the title compound (900 mg, 82%) as a yellow oil. MS m/z 415 (MH$^+$), $^1$H NMR (300 MHz, CDCl$_3$) δ ppm 1.17-1.69 (m, 5H), 1.79 (m, 2H), 1.87-2.16 (m, 3H), 2.86 (m, 1 H), 3.94 (s, 3H), 4.14 (broad m, 1 H), 5.72 (broad m, 1 H), 7.38 (s, 1 H), 7.46 (m, 2 H), 7.53 (dd, J=7.6, 8.4 Hz, 1 H), 7.61 (d, J=7.6 Hz, 1 H), 7.74 (d, J=8.4 Hz, 1 H), 7.87 (d, J=8.4 Hz, 1 H), 8.29 (s, 1 H).

13-cyclohexyl-7H-indolo[2,1-a][2]benzazepine-6,10-dicarboxylic acid, 10-methyl ester. Dissolve 7H-indolo[2,1-a][2]benzazepine-6,10-dicarboxylic acid, 13-cyclohexyl-, dimethyl ester (98 mg, 0.23 mMol) in 1.5 ml of THF, add 0.24 mL of 1.0M tetrabutylammonium hydroxide in methanol. The reaction was stirred at room temperature for 16 hrs then partitioned between ethyl acetate and 1N hydrochloric acid. The organic layer was washed with 1N hydrochloric acid, water, then brine and dried over magnesium sulfate to yield 93 mg (98%) of mono-acid product. $^1$H NMR (500 MHz, CHLOROFORM-D) δ ppm 8.29 (s, 1 H) 8.00 (s, 1 H) 7.88 (d, J=8.55 Hz, 1 H) 7.74 (d, J=8.55 Hz, 1 H) 7.58-7.65 (m, 1 H) 7.45-7.59 (m, 3 H) 5.67 (s, 1 H) 4.21 (s, 1 H) 2.84 (t, J=12.05 Hz, 1 H) 1.99-2.18 (m, 3 H) 1.92 (d, 3 H) 1.77 (d, J=7.63 Hz, 2 H) 1.40 (d, J=12.51 Hz, 2 H) 1.17-1.31 (m, 6 H, trace Bu4NOH). MS m/z 416(MH$^+$).

Intermediate 2

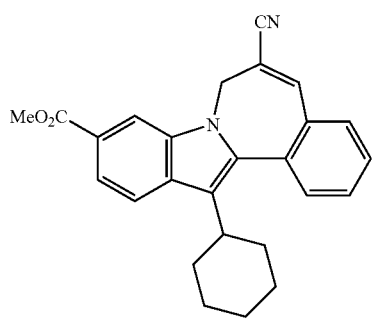

Intermediate 4

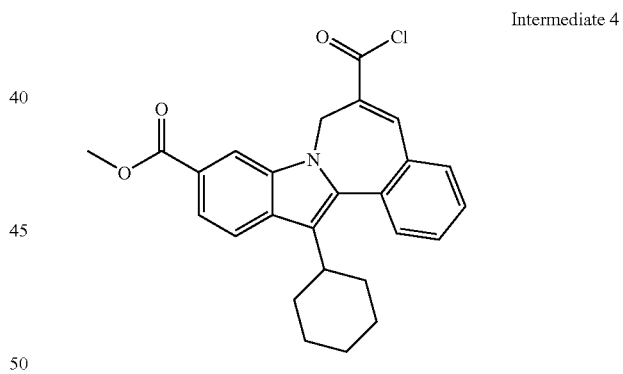

6-cyano-13-cyclohexyl-7H-indolo[2,1-a][2]benzazepine-10-carboxylic acid, methyl ester. To a solution of 7H-indolo[2,1-a][2]benzazepine-10-carboxylic acid, 6-(aminocarbonyl)-13-cyclohexyl-, methyl ester (220 mg, 0.531 mmol) in dichloromethane (5.1 mL) was added Burgess Reagent (506 mg, 2.12 mmol). The resulting solution was stirred at 22° C. for 6 hr. 1M HCl (50 mL) was added and the aqueous layer was extracted with CHCl$_3$ (2×30 mL). The organic phase was dried over Na$_2$SO$_4$, filtered, and concentrated under reduced pressure to afford the title compound (200 mg, 95%) as a yellow oil. MS m/z 397 (MH$^+$), $^1$H NMR (300 MHz, CDCl$_3$) δ ppm 1.21-1.72 (m, 5H), 1.79 (m, 2H), 1.82-2.14 (m, 3H), 2.81 (m, 1 H), 3.96 (s, 3H), 4.47 (broad m, 1 H), 5.08 (broad m, 1 H), 7.42 (d, J=8.4 Hz, 1H), 7.49-7.59 (m, 4 H), 7.78 (d, J=8.4 Hz, 1 H), 7.88 (d, J=8.4 Hz, 1 H), 8.19 (s, 1 H).

6-(chlorocarbonyl)-13-cyclohexyl-7H-indolo[2,1-a][2]benzazepine-10-carboxylic acid, methyl ester. 7H-indolo[2,1-a][2]benzazepine-6,10-dicarboxylic acid, 13-cyclohexyl-, 10-methyl ester (1.50 g, 3.61 mMol) was suspended in 30 ml of anhydrous dichloromethane. A solution of oxalyl chloride in dichloromethane (4.0 ml, 2.0M, 8.0 mMol) was added to the reaction. A catalytic amount of DMF (3 drops) was added. The reaction briefly was brought to reflux under nitrogen and allow to cool and stir under nitrogen for 2.5 hours. The reaction volatiles were removed in vacuuo. Residual oxalyl chloride was removed by azeotrop with a mixture of benzene/dichloromethane to yield 1.59 g of a yellow solid. $^1$H NMR (500 MHz, CHLOROFORM-D) δ ppm 8.25 (s, 1 H) 8.22 (s, 1 H) 7.89 (d, J=8.54 Hz, 1 H) 7.75-7.80 (m, 1 H) 7.61-7.66 (m, 2 H) 7.57-7.61 (m, 1 H) 7.54 (dd, J=5.95, 1.98 Hz, 1 H) 5.62-5.75 (m, J=14.65 Hz, 2 H) 4.23 (s, 1 H) 3.96 (s, 3 H)

2.79-2.88 (m, 1 H) 1.99-2.17 (m, 3 H) 1.87-1.99 (m, 2 H) 1.77 (d, J=7.63 Hz, 2 H) 1.31-1.68 (m, 3 H) 1.13-1.30 (m, 1 H).

Intermediate 5

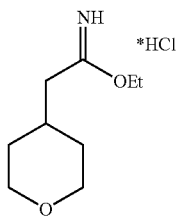

Ethyl 2-(tetrahydro-2H-pyran-4-yl)acetimidate hydrochloride. In a 3 neck round bottom flask equipped with a pipet gas inlet tube connected to an anhydrous hydrogen chloride lecture bottle and a gas out let adapter to an bubbler containing ethanol was charged 4-cyanomethyltetrahydropyran (970 mg, 775 mMol) and approximately 15 ml of anhydrous ethanol. The reaction was cooled with an ice bath and hydrogen chloride bubbled into the reaction for 1 hr. The reaction was then capped with a rubber septa and placed in a freezer for 3 days. The reaction removed from the freezer, warmed to room temperature and volatiles removed in vacuuo from the reaction mixture, to obtain 1.657 g of an amber oil. The oil was placed under nitrogen and placed in a freezer to crystallize overnight to a off white solid. 1H NMR (500 MHz, CHLOROFORM-D) δ ppm 12.41 (s, 1 H) 11.52 (s, 1 H) 4.62 (q, J=7.12 Hz, 2 H) 3.92 (dd, J=11.44, 3.51 Hz, 2 H) 3.29-3.44 (m, 2 H) 2.65 (d, J=7.32 Hz, 2 H) 2.04-2.18 (m, 1 H) 1.54-1.63 (m, 2 H) 1.43-1.51 (m, 4 H) 1.38-1.43 (m, 1 H).

Intermediate 6

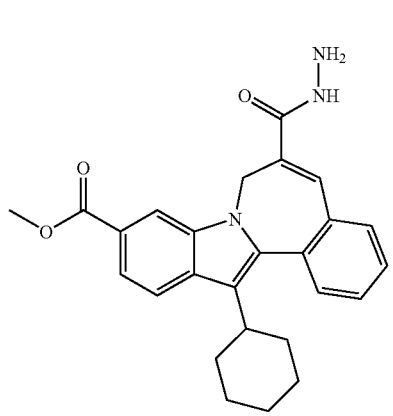

13-cyclohexyl-7H-indolo[2,1-a][2]benzazepine-6,10-dicarboxylic acid, 10-methyl ester, 6-hydrazide. The acid 7H-indolo[2,1-a][2]enzazepine-6,10-dicarboxylic acid, 13-cyclohexyl-, 10-methyl ester, (2.527 g, 6.08 mMol) was dissolved in 45 ml of DMF with hydroxybenzotriazole (HOBt) (1.27 g, 9.4 mMol). The coupling agent 1-[3-(dimethylamino)propyl]-3-ethylcarbodiimide hydrochloride (1.752 g, 9.14 mMol) was added to the reaction mixture. A bright yellow precipitate was formed within 1 hour with stirring at room temperature and 50 mL of THF added to dissolve the precipitate. The reaction was cannula transferred to a stirred flask containing 2 ml of hydrazine (63.7 mMol) in 25 mL of THF and stirred for 3 hours at room temperature. The reaction was transferred to a 1 L Erlenmeyer flask and 500 ml of water added with rapid stirring. A yellow precipitate was filtered off, rinsed with water and dried in vacuuo over phosphorus pentoxide. To yield 2.618 g (100%) of a pale yellow solid. 1H NMR (500 MHz, CHLOROFORM-D) δ ppm 8.25 (s, 1 H) 7.85 (d, J=8.54 Hz, 1 H) 7.73 (d, J=8.55 Hz, 1 H) 7.57 (d, J=7.63 Hz, 1 H) 7.48-7.54 (m, 1 H) 7.40-7.48 (m, 2 H) 7.30 (s, 1 H) 5.57 (s, 1 H) 4.17 (s, 1 H) 3.92 (s, 3 H) 3.21 (s, 2 H) 2.76-2.90 (m, 1 H) 1.87-2.23 (m, 4 H) 1.47-1.82 (m, 3 H) 1.07-1.47 (m, 4 H); MS m/z 430(MH+).

Intermediate 7

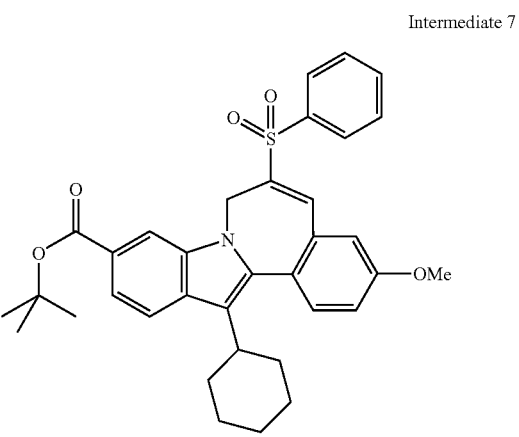

7H-Indolo[2,1-a][2]benzazepine-10-carboxylic acid, 13-cyclohexyl-3-methoxy-6-(phenyllsulfonyl)-, tert-butyl ester. To a solution of methyl 3-cyclohexyl-2-(2-formyl-4-methoxyphenyl)-1H-indole-6-carboxylate (6.00 g, 13.8 mmol) in dioxane (28.0 mL) and BEMP (7.97 mL, 27.6 mmol) was added phenyl vinyl sulfone (27.6 g, 2.21 mmol). The resulting mixture was stirred in a sealed tube in a microwave at 120° C. for 15 min. The resulting solution was concentrated under reduced pressure. Silica gel chromatography (CH₂Cl₂ H of the concentrate afforded the title compound (5.64 g, 70%) as a yellow oil. MS m/z 584 (MH+). 1H NMR (500 MHz, CHLOROFORM-d) δ ppm 1.18-1.33 (1 H, m), 1.34-1.45 (2 H, m), 1.49-57 (1 H, m), 1.64 (9 H, s.), 1.74-1.82 (2 H, m), 1.90-2.09 (4 H, m), 2.73 (1 H, m,), 3.93 (3 H, s), 4.38 (1 H, broad d), 5.08 (1 H, br. d), 7.09 (1 H, d, J=2.75 Hz), 7.12-7.18 (3 H, m), 7.22 (1 H, d, J=7.45 Hz), 7.30 (1 H, s), 7.48 (1 H, d, J=8.85 Hz), 7.54 (1 H, dd, J=8.55, 1.22 Hz), 7.61 (2 H, m), 7.67 (1 H, d, J=8.55 Hz, 8.01 (1 H, s).

Intermediate 8

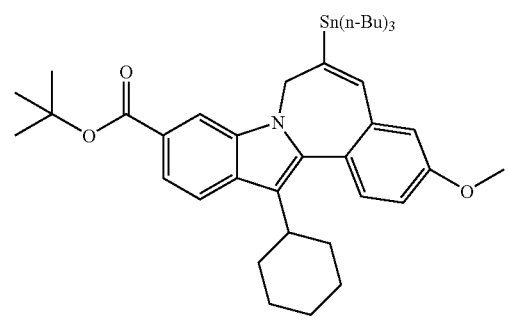

7H-indolo[2,1-a][2]benzazepine-10-carboxylic acid, 13-cyclohexyl-3-methoxy-6-(tributylstannyl)-, 1,1-dimethylethyl ester. 1,1-dimethylethyl 13-cyclohexyl-3-(methyloxy)-6-(tributylstannanyl)-7H-indolo[2,1-a][2]benzazepine-10-carboxylate. Dissolve 7H-indolo[2,1-a][2]benzazepine-10-carboxylic acid, 13-cyclohexyl-3-methoxy-6-(phenylsulfonyl)-, 1,1-dimethylethyl ester (1.00 g, 1.71 mMol) in 26 mL of benzene along with bis(tributyltin) (2.8 mL, 5.54 mMol), tributyltin hydride (136 uL, 0.513 mMol) and triethylamine (1.05 mL, 7.5 mMol). The solution was sparged for approximately for 10 minutes with nitrogen then 2,2'-bisazoisobutyronitrile (AIBN) (96 mg, 0.58 mMol) added to the reaction. The reaction was heated to reflux under nitrogen for 2 hr. The reaction was followed by LC-MS using the following HPLC conditions: Shimadzu Analytical HPLC using Discovery VP software: % A=5% acetonitrile, 95% water, 10 mmol Ammonium Acetate % B=95% acetonitrile, 5% water, 10 mmol Ammonium Acetate; Initial % B=0; Final % B=100; Gradient=3 min; Runtime=10 min; Flow rate=5 ml/min; Wavelength=220 nm; Column=Waters Xterra, 3 mm×50 mm, S7. To the reaction was added tributyltin hydride (0.45 mL, 1.7 mMol) and AIBN (95 mg, 0.58 mMol), the reaction heated to reflux for 2 hrs, and analyzed for progress. AIBN (99 mg, 0.60 mMol) added to the reaction and the reaction heated to reflux under for an additional 6 hrs using a timer. The reaction was analyzed by LC-MS for progress then tributyltin hydride (1.0 ml, 3.8 mMol) and AIBN (97 mg, 0.59 mMol) was added and the reaction heated to reflux for 2 hrs 20 min. The reaction was analyzed by LC-MS and AIBN (97 mg, 0.59 mMol) added to the reaction. The reaction was heated for 1 hr under nitrogen at reflux and the cooled and analyzed by LC-MS. Volatiles were removed in vacuuo from the reaction and the reaction was purified by column chromatography using a $C_{18}$ packing of 190 g of YMC GEL ODS-A, 120A spherical 75 uM. The reaction residue (6.67 g of yellow oil) was dissolved in a minimum of dichloromethane and the solution applied onto the reverse phase column packed in 10% dichloromethane in acetonitrile. Initial elution was done using 10% dichloromethane in acetonitrile followed by elution with 15% dichloromethane in acetonitrile. The chromatography was monitored by TLC using Whatman MKC18F reverse phase 1"×3" 200 uM thickness TLC plates eluting using 15% dichloromethane in acetonitrile. Compound observation was accomplished by UV lamp at 254 nm and iodine staining of TLC plates. Product fractions were collected and volatiles removed in vacuuo to yield 647 mg (52%) as a pale yellow foam. 1H NMR (500 MHz, CHLOROFORM-D) δ ppm 0.71-0.83 (m, 9 H) 0.85-0.96 (m, 3 H) 0.95-1.08 (m, 6 H) 1.15-1.27 (m, 7 H) 1.27-1.49 (m, 11 H) 1.53 (s, 5 H) 1.60-1.67 (m, 9 H) 1.68-1.82 (m, 2 H) 1.84-1.96 (m, 1 H) 1.96-2.16 (m, 3 H) 2.74-2.91 (m, 1 H) 3.90 (s, 3 H) 4.16-4.40 (m, 1 H) 4.82-5.03 (m, 1 H) 6.72-6.90 (m, 2 H) 6.96 (dd, J=8.55, 2.44 Hz, 1 H) 7.43 (d, J=8.55 Hz, 1 H) 7.66 (dd, J=8.39, 1.37 Hz, 1 H) 7.81 (d, J=8.55 Hz, 1 H) 8.04 (s, 1 H). LC-MS: Shimadzu Analytical HPLC using Discovery VP software: % A=5% acetonitrile, 95% water, 10 mmol Ammonium Acetate; % B=95% acetonitrile, 5% water, 10 mmol Ammonium Acetate; Initial % B=0; Final % B=100; Gradient=3 min; Runtime=10 min; Flow rate=5 ml/min; Wavelength=220 nm; Column=Waters Xterra, 3 mm×50 mm, S7. Retention Time=4.2 min, MS m/z 734(MH$^+$).

Methyl 13-cyclohexyl-3-(methyloxy)-6-(((5-(methyloxy)-2,5-dioxopentyl)amino)carbonyl)-7H-indolo[2,1-a] [2]benzazepine-10-carboxylate. 13-cyclohexyl-3-(methyloxy)-10-((methyloxy)carbonyl)-7H-indolo[2,1-a][2] benzazepine-6-carboxylic acid (1.00 g, 2.24 mMol) was dissolved in 20 ml of DMF along with 1-hydroxy-7-azabenzotriazole (483 mg, 3.5 mMol). The reaction was placed under nitrogen and 1-[3-(dimethylamino)propyl]-3-ethylcarbodiimide hydrochloride (663 mg, 3.5 mMol) was added and the reaction stirred for 1 hr at room temperature. 5-aminolevleunic acid hydrochloride (608 mg, 3.35 mMol) was added to the reaction followed by diisopropylethyl amine (0.44 mL, 2.5 mMol). The reaction was stirred overnight under nitrogen at room temperature. Volatiles were removed in vacuuo and the residue was partitioned between ethyl acetate and 0.1 N hydrochloric acid. The aqueous phase was extracted with ethyl acetate and the organic phases combined, washed with brine and dried over magnesium sulfate. Volatiles were removed in vacuuo to yield 1.47 g of crude product which was combined with 698 mg of a previous experiment. The crude product was purified by silica gel chromatography eluting with a gradient of 10% ethyl acetate/dichloromethane to 25% ethyl acetate/dichloromethane to yield 1.64 g (84%) of product as a yellow solid. $^1$H NMR (500 MHz, CHLOROFORM-D) □ ppm 1.12-1.30 (m, 1 H) 1.32-1.50 (m, 2 H) 1.77 (d, J=9.16 Hz, 2 H) 1.89-1.99 (m, 1 H) 1.99-2.18 (m, 3 H) 2.67 (t, J=6.10 Hz, 2 H) 2.72-2.87 (m, 3 H) 3.67 (s, 3 H) 3.91 (s, 3 H) 3.94 (s, 3 H) 4.15 (d, J=19.23 Hz, 1 H) 4.31 (d, J=34.79 Hz, 2 H) 5.62 (d, J=12.82 Hz, 1 H) 6.70 (t, J=4.12 Hz, 1 H) 6.96 (d, J=2.44 Hz, 1 H) 7.08 (dd, J=8.55, 2.75 Hz, 1 H) 7.33 (s, 1 H) 7.51 (d, J=8.55 Hz, 1 H) 7.73 (d, J=8.24 Hz, 1 H) 7.84 (d, J=8.24 Hz, 1 H) 8.26 (s, 1 H); MS m/z 573(MH$^+$); MS m/z 571(M-H)$^-$.

Intermediate 10

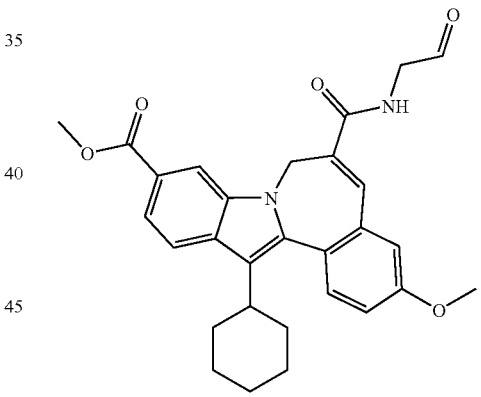

13-cyclohexyl-3-(methyloxy)-10-((methyloxy)carbonyl)-7H-indolo[2,1-a][2]benzazepine-6-carboxylic acid (1.50 g, 3.37 mMol) was dissolved in 32 ml of DMF along with 1-hydroxy-7-azabenzotriazole (697 mg, 5.1 mMol). The reaction was placed under nitrogen and 1-[3-(dimethylamino)propyl]-3-ethylcarbodiimide hydrochloride (967 mg, 5.04 mMol) was added and the reaction stirred for 1.5 hr at room temperature. Aminoacetaldehyde dimethylacetal (0.44 mL, 4.1 mMol) was added to the reaction and the reaction stirred at room temperature under nitrogen for 16 hrs. Volatiles were removed in vacuuo and the residue was partitioned between ethyl acetate and 0.1 N hydrochloric acid. The aqueous phase was extracted with ethyl acetate and the organic phases combined, washed with 0.1N hydrochloric acid then brine and dried over magnesium sulfate. Volatiles were removed in vacuuo to yield 1.98 g of crude product which was used in the next reaction without purification. The crude acetal (1.4 g, 2.7 mMol) was dissolved in 30 mL of acetone and 2M hydrochloric acid (1.6 mL, 3.2 mMol) and briefly Intermediate 9

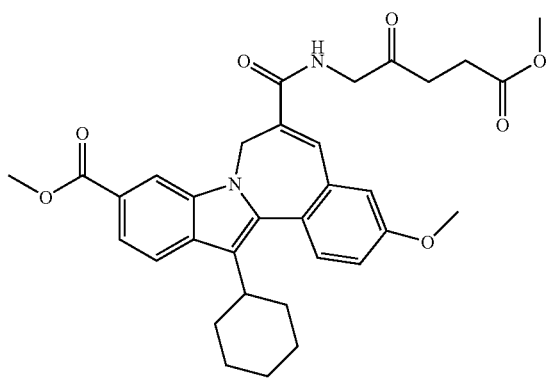

heated to reflux then allow to stir for 2.5 hrs before being briefly heated to reflux again and allowed to stir an additional 1.5 hrs. 1N hydrochloric acid (200 mL) was added to the reaction and a precipitate filtered off and rinsed with water and dried in vacuuo, to yield 1.14 g (87%) of crude product. The product was purified by silica gel chromatography eluting with a gradient of 15% ethyl acetate in hexanes to 25% ethyl acetate in hexanes to yield 0.81 g (62%) of product as a yellow solid. 1H NMR (500 MHz, CHLOROFORM-D) δ ppm 1.25 (t, J=7.17 Hz, 1 H) 1.31-1.48 (m, 2 H) 1.48-1.63 (m, 3 H) 1.77 (d, J=9.46 Hz, 2 H) 1.86-1.98 (m, 1 H) 1.98-2.16 (m, 3 H) 2.77-2.89 (m, 1 H) 3.91 (s, 3 H) 3.94 (s, 3 H) 4.18 (d, J=14.04 Hz, 1 H) 4.32 (d, J=34.79 Hz, 2 H) 5.62 (d, J=11.29 Hz, 1 H) 6.65 (s, 1 H) 6.97 (d, J=2.75 Hz, 1 H) 7.09 (dd, J=8.55, 2.75 Hz, 1H) 7.35 (s, 1 H) 7.52 (d, J=8.85 Hz, 1 H) 7.73 (d, J=8.55 Hz, 1 H) 7.84 (d, J=8.54 Hz, 1 H) 8.26 (s, 1 H) 9.71 (s, 1 H). Shimadzu LC-MS discovery software; % A=10% methanol, 90% water, 0.1% TFA; % B=90% methanol, 10% water, 0.1% TFA Initial % B=50; Final % B=100; Gradient=5 min; Runtime=6 min; Flow rate=5 ml/min; UV@ 220 nm; Column=Phenomenex Luna C18, 10u, 3.0 mm×50 mm Product Retention time=4.2 min. MS m/z 487(MH$^+$).

Intermediate 11

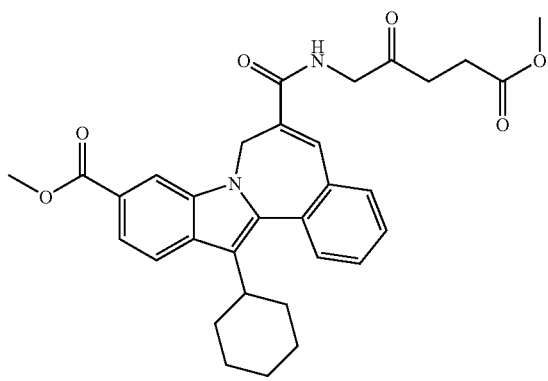

13-cyclohexyl-6-[[(5-methoxy-2,5-dioxopentyl)amino]carbonyl]-7H-indolo[2,1-a][2]benzazepine-10-carboxylic acid, methyl ester. 7H-indolo[2,1-a][2]benzazepine-10-carboxylic acid, 6-(chlorocarbonyl)-13-cyclohexyl-, methyl ester (499 mg, 1.15 mMol) was dissolved in 10 ml of anhydrous dichloromethane and methyl 5-aminolevulinate hydrochloride (244 mg, 1.34 mMol) was added to the reaction mixture followed by 0.5 ml of pyridine (6.2 mMol). The reaction was stirred under nitrogen at room temperature for 40 hours. Volatiles were removed in vacuuo and the residue was partitioned between ethyl acetate and 0.1 N hydrochloric acid. The organic phase was washed with brine, dried over magnesium sulfate to yield 603 mg of crude product. The product was combined with 433 mg of a previous reaction run under the same conditions. The mixture was purified by silica column chromatography eluting with a gradient of 20% ethyl acetate in dichloromethane to 20% ethyl acetate in dichloromethane to yield 0.56 g (45%) of product. 1H NMR (500 MHz, CHLOROFORM-D) δ ppm 8.28 (s, 1 H) 7.87 (d, J=8.55 Hz, 1 H) 7.74 (dd, J=8.55, 1.22 Hz, 1 H) 7.59 (d, J=7.93 Hz, 1 H) 7.43-7.56 (m, 3 H) 7.38 (s, 1 H) 6.71 (t, J=4.12 Hz, 1 H) 5.65 (d, J=10.99 Hz, 1 H) 4.31 (d, J=27.16 Hz, 2 H) 4.14-4.23 (m, 1 H) 3.94 (s, 3 H) 3.67 (s, 3 H) 2.80-2.91 (m, 1 H) 2.01-2.16 (m, 3 H) 1.70-2.00 (m, 3 H) 1.29-1.70 (m, 6 H) 1.14-1.31 (m, 2 H); MS m/z 543(MH$^+$), 560(MNH$_4^+$).

Intermediate 12

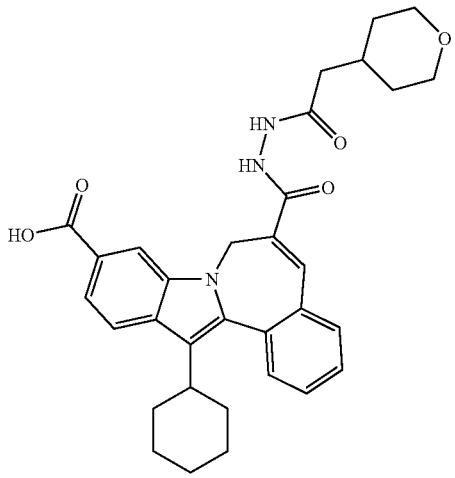

13-cyclohexyl-, 6-[2-[2-(tetrahydro-2H-pyran-4-yl)acetyl]hydrazide]-7H-indolo[2,1-a][2]benzazepine-6,10-dicarboxylic acid. 7H-indolo[2,1-a][2]benzazepine-6,10-dicarboxylic acid, 13-cyclohexyl-, 6-[2-[2-(tetrahydro-2H-pyran-4-yl)acetyl]hydrazide] was isolated as a by-product from the hydrolysis of 7H-indolo[2,1-a][2]benzazepine-10-carboxylic acid, 13-cyclohexyl-6-[5-[(tetrahydro-2H-pyran-4-yl)methyl]-1,3,4-oxadiazol-2-yl]-, methyl ester using the above HPLC conditions. Retention time was 6.9 minutes. 1H NMR (500 MHz, CHLOROFORM-D) δ ppm 11.64 (s, 1 H) 9.68 (d, J=5.80 Hz, 1 H) 8.56 (s, 1 H) 7.92 (d, J=8.54 Hz, 1 H) 7.78 (d, J=8.24 Hz, 1 H) 7.65 (d, J=7.63 Hz, 1 H) 7.46-7.61 (m, 4 H) 5.84 (d, J=14.95 Hz, 1 H) 4.18 (d, J=14.34 Hz, 1 H) 3.93 (d, J=10.99 Hz, 2 H) 3.37 (t, J=11.44 Hz, 2 H) 2.79-2.91 (m, 1 H) 2.44 (d, J=6.71 Hz, 2 H) 1.92-2.25 (m, 7 H) 1.76 (t, J=11.29 Hz, 3 H) 1.67 (t, J=9.92 Hz, 3 H) 1.53 (d, J=10.99 Hz, 2 H) 1.32-1.50 (m, 5 H) 1.15-1.28 (m, 1 H); MS m/z 542 (MH$^+$).

EXAMPLE 1

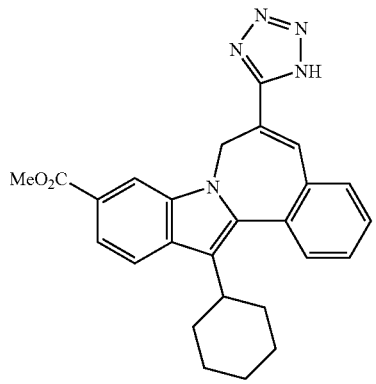

13-cyclohexyl-6-(1H-tetrazol-5-yl)-7H-indolo[2,1-a][2]benzazepine-10-carboxylic acid, methyl ester. To a solution of 7H-indolo[2,1-a][2]benzazepine-10-carboxylic acid, 6-cyano-13-cyclohexyl-, methyl ester (200 mg, 0.504 mmol) in toluene (2.0 mL) was added tributyltin azide (502 mg, 1.51 mmol). The resulting solution was stirred in a sealed tube in a microwave at 150° C. for 30 min. 1M HCl (15 mL) was added and the aqueous layer was extracted with CHCl$_3$ (2×30 mL). The organic phase was dried over Na$_2$SO$_4$, filtered, and concentrated under reduced pressure. Silica gel chromatography (9:1 EtOAc:methanol) of the concentrate afforded the title compound (191 mg, 86%) as a yellow oil. MS m/z 440 (MH$^+$), $^1$H NMR (300 MHz, CD$_3$OD) δ ppm 1.18-1.69 (m, 5H), 1.79 (m, 2H), 1.86-2.15 (m, 3H), 2.87 (m, 1 H), 3.94 (s, 3H), 4.52 (broad m, 1 H), 5.97 (broad m, 1 H), 7.49-7.54 (m, 3 H), 7.62 (d, J=7.6 Hz, 1 H), 7.68 (d, J=8.4 Hz, 1 H), 7.75 (s, 1 H), 7.86 (d, J=8.4 Hz, 1 H), 8.38 (s, 1 H).

EXAMPLES 2 AND 3

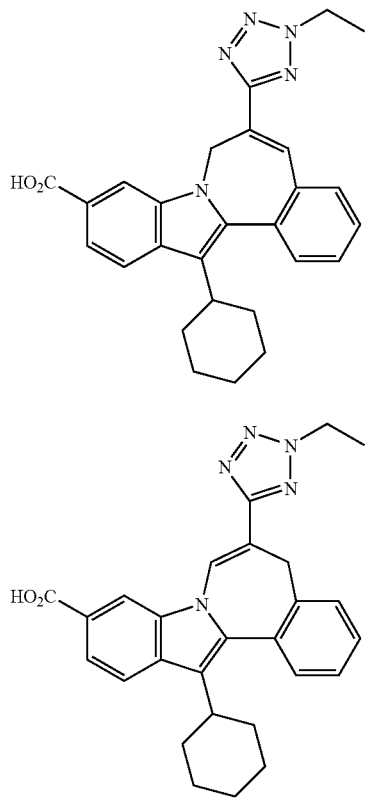

13-cyclohexyl-6-(2-ethyl-2H-tetrazol-5-yl)-5H-indolo[2,1-a][2]benzazepine-10-carboxylic acid and 13-cyclohexyl-6-(2-ethyl-2H-tetrazol-5-yl)-7H-indolo[2,1-a][2]benzazepine-10-carboxylic acid. To a solution of 7H-indolo[2,1-a][2]benzazepine-10-carboxylic acid, 13-cyclohexyl-6-(1H-tetrazol-5-yl)-, methyl ester (40 mg, 0.09 mmol) in DMF (1.0 mL) and cesium carbonate (60 mg, 0.18 mmol) was added iodoethane (28 mg, 0.18 mmol). The resulting mixture was heated at 60° C. for 18 hr. Water (1 mL) was added and the mixture was heated at 60° C. for an additional 8 hr. 1M HCl (15 mL) was added and the aqueous layer was extracted with CHCl$_3$ (2×30 mL). The organic phase was dried over Na$_2$SO$_4$, filtered, and concentrated under reduced pressure. This oil was purified by reverse-phase prep HPLC to afford the title compounds. 7H-indolo[2,1-a][2]benzazepine-10-carboxylic acid, 13-cyclohexyl-6-(2-ethyl-2H-tetrazol-5-yl)-: 20 mg, 49% yield. MS m/z 454 (MH$^+$), $^1$H NMR (300 MHz, CD$_3$OD) δ ppm 1.17-1.66 (m, 5H), 1.68 (t, 3 H), 1.79 (m, 2H), 1.86-2.15 (m, 3H), 2.88 (m, 1 H), 4.49 (broad m, 1 H), 4.70 (q, 2 H), 5.97 (broad m, 1 H), 7.47-7.58 (m, 3 H), 7.62 (d, J=7.6 Hz, 1 H), 7.71 (d, J=8.4 Hz, 1 H), 7.86 (d, J=8.4 Hz, 1 H), 7.90 (s, 1 H), 8.41 (s, 1 H). 5H-indolo[2,1-a][2]benzazepine-10-carboxylic acid, 13-cyclohexyl-6-(2-ethyl-2H-tetrazol-5-yl)-: 11 mg, 27% yield. MS m/z 454 (MH$^+$), $^1$H NMR (300 MHz, CD$_3$OD) δ ppm 1.16-1.64 (m, 5H), 1.68 (t, 3H), 1.79 (m, 2H), 1.86-2.15 (m, 3H), 3.05 (m, 1 H), 3.68 (broad m, 1 H), 4.13 (broad m, 1 H), 4.67 (q, 2 H), 7.31-7.39 (m, 2 H), 7.41-7.48 (m, 2 H), 7.96 (t, J=8.4, 8.4 Hz, 2 H), 8.20 (s, 1 H), 8.38 (s, 1 H).

EXAMPLE 4

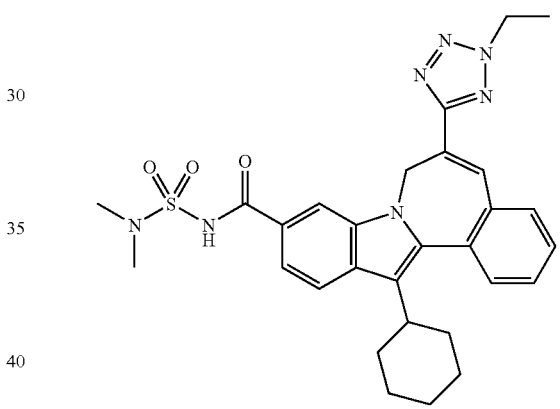

13-cyclohexyl-N-[(dimethylamino)sulfonyl]-6-[2-ethyl)-2H-tetrazol-5-yl]-7H-indolo[2,1-a][2]benzazepine-10-carboxamide. To a solution of 7H-indolo[2,1-a][2]benzazepine-10-carboxylic acid, 13-cyclohexyl-6-(2-ethyl-2H-tetrazol-5-yl)-(87 mg, 0.19 mmol) in CH$_2$Cl$_2$ (1.0 mL) was added 2M oxalyl chloride (0.48 mL, 0.96 mmol). This solution was stirred at 22° C. for 3 hr and then concentrated under reduced pressure. BEMP (0.22 mL, 0.76 mmol), CH$_2$Cl$_2$ (1.0 mL) and N,N-dimethylsulfamide (120 mg, 0.96 mmol) was added to the resulting oil. The resulting mixture was stirred for 6 hr at 22° C. 1M HCl (15 mL) was added and the aqueous layer was extracted with CHCl$_3$ (2×30 mL). The organic phase was dried over Na$_2$SO$_4$, filtered, and concentrated under reduced pressure. This oil was purified by reverse-phase prep HPLC to afford the title compound (56 mg, 52%) as a yellow paste. MS m/z 561 (MH$^+$), $^1$H NMR (300 MHz, CD$_3$OD) δ ppm 1.16-1.64 (m, 5H), 1.68 (t, 3 H), 1.80 (m, 2H), 1.86-2.16 (m, 3H), 2.89 (m, 1 H), 3.09 (s, 6H), 4.52 (broad m, 1 H), 4.71 (q, 2 H), 5.97 (broad m, 1 H), 7.45-7.56 (m, 3 H), 7.61 (d, J=7.6 Hz, 1 H), 7.69 (d, J=8.4 Hz, 1 H), 7.83 (d, J=8.4 Hz, 1 H), 7.87 (s, 1 H), 8.40 (s, 1 H), 8.69 (broad s, 1H).

EXAMPLE 5

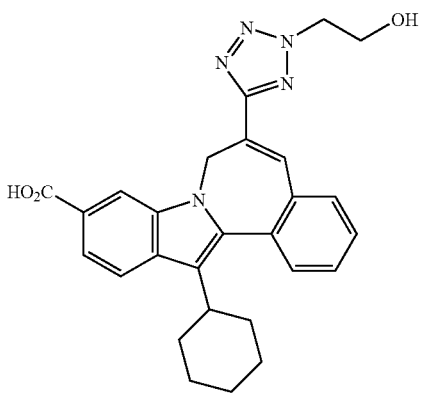

13-cyclohexyl-6-[2-(2-hydroxyethyl)-2H-tetrazol-5-yl]-7H-indolo[2,1-a][2]benzazepine-10-carboxylic acid. To a solution of 7H-indolo[2,1-a][2]benzazepine-10-carboxylic acid, 13-cyclohexyl-6-(1H-tetrazol-5-yl)-, methyl ester (40 mg, 0.09 mmol) in DMF (1.0 mL) and cesium carbonate (60 mg, 0.18 mmol) was added 2-chloroethanol (15 mg, 0.18 mmol). The resulting mixture was heated at 60° C. for 18 hr. Water (1 mL) was added and the mixture was heated at 60° C. for an additional 8 hr. 1M HCl (15 mL) was added and the aqueous layer was extracted with CHCl$_3$ (2×30 mL). The organic phase was dried over Na$_2$SO$_4$, filtered, and concentrated under reduced pressure. This oil was purified by reverse-phase prep HPLC to afford the title compound (21 mg, 49% yield) as a yellow paste. MS m/z 470 (MH$^+$), $^1$H NMR (300 MHz, CD$_3$OD) δ ppm 1.18-1.69 (m, 5H), 1.79 (m, 2H), 1.86-2.15 (m, 3H), 2.89 (m, 1 H), 4.20 (broad m, 1 H), 4.32-4.56 (broad m, 2H), 4.68-4.92 (broad m, 2H), 5.92 (broad m, 1 H), 7.48-7.58 (m, 3 H), 7.61 (d, J=7.6 Hz, 1 H), 7.66 (d, J=8.4 Hz, 1 H), 7.75 (d, J=8.4 Hz, 1 H), 7.90 (s, 1 H), 8.39 (s, 1 H).

EXAMPLES 6 AND 7

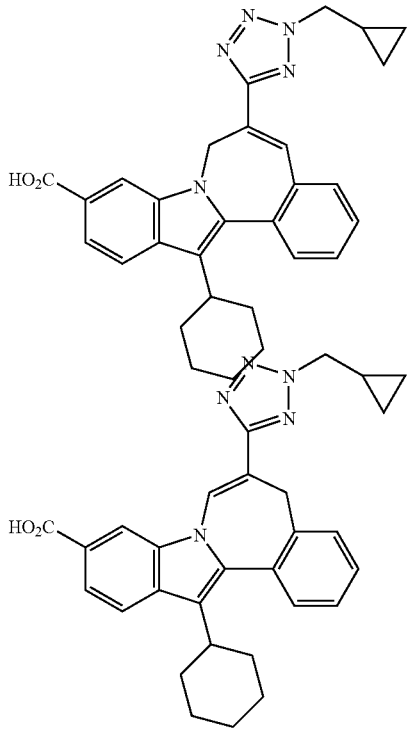

13-cyclohexyl-6-[2-(cyclopropylmethyl)-2H-tetrazol-5-yl]-7H-indolo[2,1-a][2]benzazepine-10-carboxylic acid and 13-cyclohexyl-6-[2-(cyclopropylmethyl)-2H-tetrazol-5-yl]-5H-indolo[2,1-a][2]benzazepine-10-carboxylic acid. To a solution of 7H-indolo[2,1-a][2]benzazepine-10-carboxylic acid, 13-cyclohexyl-6-(1H-tetrazol-5-yl)-, methyl ester (40 mg, 0.09 mmol) in DMF (1.0 mL) and cesium carbonate (60 mg, 0.18 mmol) was added (bromomethyl)cyclopropane (24 mg, 0.18 mmol). The resulting mixture was heated at 60° C. for 18 hr. Water (1 mL) was added and the mixture was heated at 60° C. for an additional 8 hr. 1M HCl (15 mL) was added and the aqueous layer was extracted with CHCl$_3$ (2×30 mL). The organic phase was dried over Na$_2$SO$_4$, filtered, and concentrated under reduced pressure. This oil was purified by reverse-phase prep HPLC to afford the title compounds. 7H-indolo[2,1-a][2]benzazepine-10-carboxylic acid, 13-cyclohexyl-6-[2-(cyclopropylmethyl)-2H-tetrazol-5-yl]-: 22 mg, 50% yield. MS m/z 480 (MH$^+$), $^1$H NMR (300 MHz, CD$_3$OD) δ ppm 0.58 (m, 2 H), 0.70 (m, 2 H), 1.17-1.67 (m, 6H), 1.80 (m, 2H), 1.85-2.15 (m, 3H), 2.90 (m, 1 H), 4.42-4.58 (broad m, 3 H), 5.94 (broad m, 1 H), 7.49-7.54 (m, 3 H), 7.62 (d, J=7.6 Hz, 1 H), 7.72 (d, J=8.4 Hz, 1 H), 7.86 (d, J=8.4 Hz, 1 H), 7.91 (s, 1 H), 8.49 (s, 1 H). 5H-indolo[2,1-a][2]benzazepine-10-carboxylic acid, 13-cyclohexyl-6-[2-(cyclopropylmethyl)-2H-tetrazol-5-yl]-: 11 mg, 25% yield. MS m/z 480 (MH$^+$), $^1$H NMR (300 MHz, CD$_3$OD) δ ppm 0.50 (m, 2 H), 0.59 (m, 2 H), 1.19-1.69 (m, 6H), 1.81 (m, 2H), 1.85-2.15 (m, 3H), 3.10 (m, 1 H), 3.71 (broad m, 1 H), 4.18 (broad m, 1H), 4.49 (d, 2H), 7.31-7.39 (m, 2 H), 7.42-7.49 (m, 2 H), 7.96 (t, J=8.4, 8.4 Hz, 2 H), 8.20 (s, 1 H), 8.37 (s, 1 H).

EXAMPLES 8, 9, AND 10

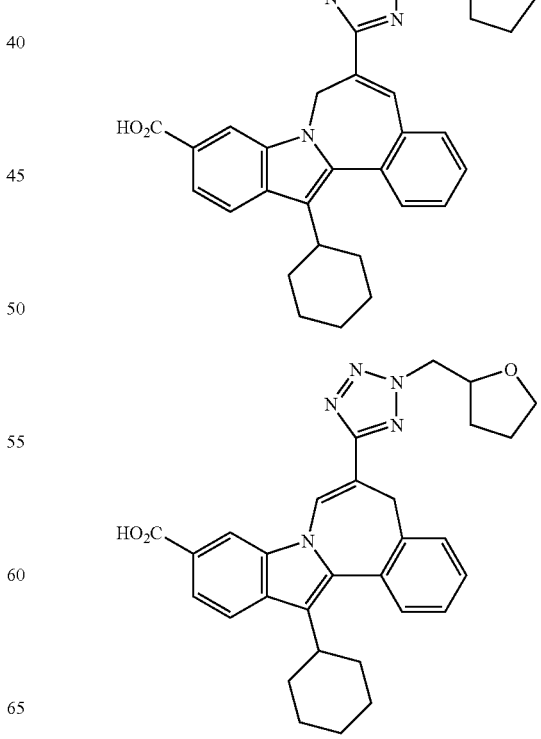

-continued

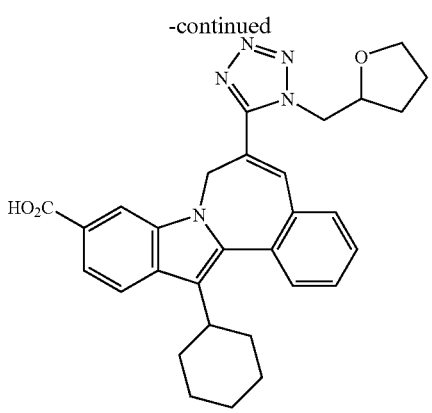

EXAMPLES 11, 12, 13, AND 14

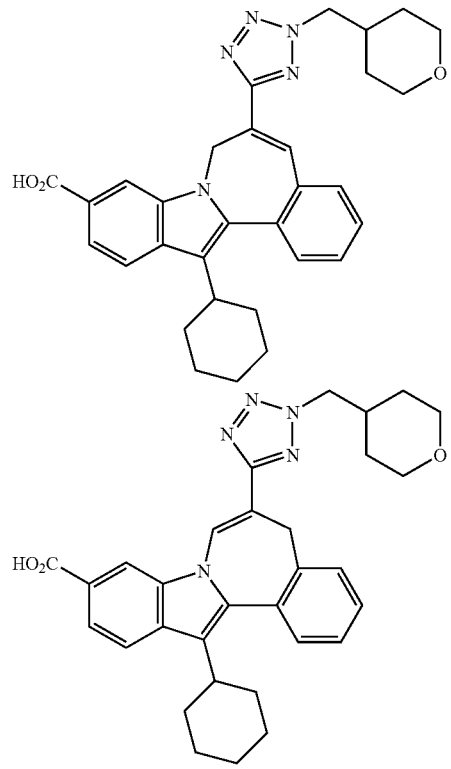

13-cyclohexyl-6-[2-[(tetrahydro-2-furanyl)methyl]-2H-tetrazol-5-yl]-5H-indolo[2,1-a][2]benzazepine-10-carboxylic acid and 13-cyclohexyl-6-[2-[(tetrahydro-2-furanyl)methyl]-2H-tetrazol-5-yl]-7H-indolo[2,1-a][2]benzazepine-10-carboxylic acid and 13-cyclohexyl-6-[1-[(tetrahydro-2-furanyl)methyl]-1H-tetrazol-5-yl]-7H-indolo[2,1-a][2]benzazepine-10-carboxylic acid. To a solution of 7H-indolo[2,1-a][2]benzazepine-10-carboxylic acid, 13-cyclohexyl-6-(1H-tetrazol-5-yl)-, methyl ester (40 mg, 0.09 mmol) in DMF (1.0 mL) and cesium carbonate (60 mg, 0.18 mmol) was added 2-(bromomethyl)-tetrahydrofuran (30 mg, 0.18 mmol). The resulting mixture was heated at 60° C. for 18 hr. Water (1 mL) was added and the mixture was heated at 60° C. for an additional 8 hr. 1M HCl (15 mL) was added and the aqueous layer was extracted with CHCl$_3$ (2×30 mL). The organic phase was dried over Na$_2$SO$_4$, filtered, and concentrated under reduced pressure. This oil was purified by reverse-phase prep HPLC to afford the title compounds. 7H-indolo[2,1-a][2]benzazepine-10-carboxylic acid, 13-cyclohexyl-6-[2-[(tetrahydro-2-furanyl)methyl]-2H-tetrazol-5-yl]-: 22 mg, 48% yield. MS m/z 510 (MH$^+$), $^1$H NMR (300 MHz, CD$_3$OD) δ ppm 1.18-1.69 (m, 5H), 1.79 (m, 2H), 1.86-2.27 (m, 7H), 2.92 (m, 1 H), 3.78 (m, 1H), 3.93 (m, 1H), 4.52 (broad m, 1 H), 4.54-4.87 (m, 3H), 5.98 (broad m, 1 H), 7.49-7.54 (m, 3 H), 7.64 (d, J=7.6 Hz, 1 H), 7.78 (d, J=8.4 Hz, 1 H), 7.91 (d, J=8.4 Hz, 1 H), 7.95 (s, 1 H), 8.49 (s, 1 H). 5H-indolo[2,1-a][2]benzazepine-10-carboxylic acid, 13-cyclohexyl-6-[2-[(tetrahydro-2-furanyl)methyl]-2H-tetrazol-5-yl]-: 10 mg, 22% yield. MS m/z 510 (MH$^+$), $^1$H NMR (300 MHz, CD$_3$OD) δ ppm 1.19-1.69 (m, 5H), 1.81 (m, 2H), 1.83-2.25 (m, 7H), 3.12 (m, 1 H), 3.71 (broad m, 1 H), 3.83 (m, 1H), 3.92 (m, 1H), 4.15 (broad m, 1H), 4.51 (m, 1H), 4.62 (m, 1H), 4.73 (m, 1H), 7.32-7.38 (m, 2 H), 7.42-7.49 (m, 2 H), 7.98 (t, J=8.4, 8.4 Hz, 2 H), 8.20 (s, 1 H), 8.38 (s, 1 H). 7H-indolo[2,1-a][2]benzazepine-10-carboxylic acid, 13-cyclohexyl-6-[1-[(tetrahydro-2-furanyl)methyl]-1H-tetrazol-5-yl]-: 8 mg, 17% yield. MS m/z 510 (MH$^+$), $^1$H NMR (300 MHz, CD$_3$OD) δ ppm 1.19-1.70 (m, 5H), 1.78 (m, 2H), 1.84-2.26 (m, 7H), 2.92 (m, 1 H), 3.80 (m, 1H), 3.92 (m, 1H), 4.50 (broad m, 1 H), 4.55-4.87 (m, 3H), 5.97 (broad m, 1 H), 7.49-7.54 (m, 3 H), 7.65 (d, J=7.6 Hz, 1 H), 7.78 (d, J=8.4 Hz, 1 H), 7.90 (d, J=8.4 Hz, 1 H), 7.94 (s, 1 H), 8.48 (s, 1 H).

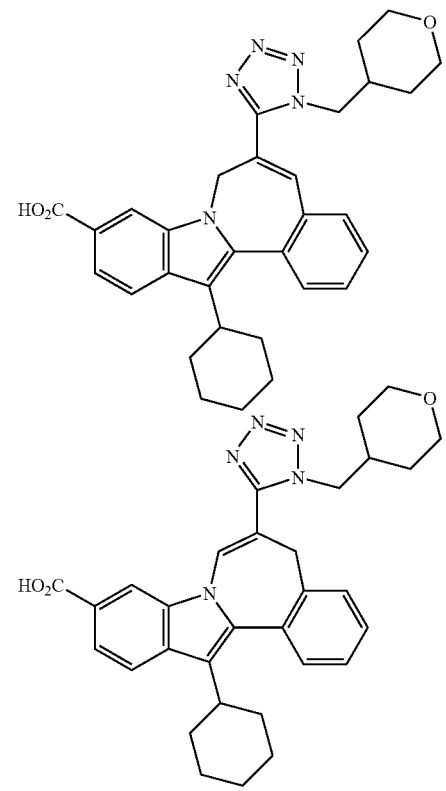

13-cyclohexyl-6-[2-[(tetrahydro-2H-pyran-4-yl)methyl]-2H-tetrazol-5-yl]-7H-indolo[2,1a][2]benzazepine-10-carboxylic acid and 13-cyclohexyl-6-[2-[(tetrahydro-2H-pyran-4-yl)methyl]-2H-tetrazol-5-yl]-5H-indolo[2,1-a][2]benzazepine-10-carboxylic acid and 13-cyclohexyl-6-[1-[(tetrahydro-2H-pyran-4-yl)methyl]-1H-tetrazol-5-yl]-7H-indolo[2,1-a][2]benzazepine-10-carboxylic acid and 13-cyclohexyl6-[1-[(tetrahydro-2H-pyran-4-yl)methyl]-1H-tetrazol-5-yl]-5H-indolo[2,1-a][2]benzazepine-10-carboxylic acid. To a solution of 7H-indolo[2,1-a][2]benzazepine-10-carboxylic acid, 13-cyclohexyl-6-(1H-tetrazol-5-yl)-, methyl ester (40 mg, 0.09 mmol) in DMF (1.0 mL) and cesium carbonate (60 mg, 0.18 mmol) was added 4-(bromomethyl)-tetrahydro-2H-pyran (31 mg, 0.18 mmol). The resulting mixture was heated at 60° C. for 18 hr. Water (1 mL) was added and the mixture was heated at 60° C. for an additional 8 hr. 1M HCl (15 mL) was added and the aqueous layer was extracted with CHCl$_3$ (2×30 mL). The organic phase was dried over Na$_2$SO$_4$, filtered, and concentrated under reduced pressure. This oil was purified by reverse-phase prep HPLC to afford the title compounds. 7H-indolo[2,1-a][2]benzazepine-10-carboxylic acid, 13-cyclohexyl-6-[2-[(tetrahydro-2H-pyran-4-yl)methyl]-2H-tetrazol-5-yl]-: 21 mg, 44% yield. MS m/z 524 (M$^+$), $^1$H NMR (300 MHz, CD$_3$OD) δ ppm 1.18-1.69 (m, 6H), 1.79 (m, 2H), 1.86-2.20 (m, 7H), 2.91 (m, 1 H), 3.39 (m, 2H), 3.96 (m, 2H), 4.52 (broad m, 3 H), 5.97 (broad m, 1 H), 7.48-7.54 (m, 3 H), 7.62 (d, J=7.6 Hz, 1 H), 7.71 (d, J=8.4 Hz, 1 H), 7.87 (d, J=8.4 Hz, 1 H), 7.95 (s, 1 H), 8.39 (s, 1 H). 5H-indolo[2,1-a][2]benzazepine-10-carboxylic acid, 13-cyclohexyl-6-[2-[(tetrahydro-2H-pyran-4-yl)methyl]-2H-tetrazol-5-yl]-: 9 mg, 19% yield. MS m/z 524 (MH$^+$), $^1$H NMR (300 MHz, CD$_3$OD) δ ppm 1.19-1.69 (m, 6H), 1.81 (m, 2H), 1.83-2.21 (m, 7H), 3.10 (m, 1 H), 3.42 (m, 2H), 3.71 (broad m, 1 H), 3.98 (m, 2H), 4.12 (broad m, 1H), 4.51 (m, 2H), 7.32-7.38 (m, 2 H), 7.42-7.49 (m, 2 H), 7.98 (t, J=8.4, 8.4 Hz, 2 H), 8.20 (s, 1 H), 8.38 (s, 1 H). 7H-indolo[2,1-a][2]benzazepine-10-carboxylic acid, 13-cyclohexyl-6-[1-[(tetrahydro-2H-pyran-4-yl)methyl]-1H-tetrazol-5-yl]-: 6 mg, 13% yield. MS m/z 524 (MH$^+$), $^1$H NMR (300 MHz, CD$_3$OD) δ ppm 1.18-1.69 (m, 6H), 1.79 (m, 2H), 1.86-2.20 (m, 7H), 2.90 (m, 1 H), 3.59 (m, 2H), 3.89 (m, 2H), 4.52 (broad m, 1 H), 4.69 (m, 2H), 5.97 (broad m, 1 H), 7.48-7.54 (m, 3 H), 7.62 (d, J=7.6 Hz, 1 H), 7.71 (d, J=8.4 Hz, 1 H), 7.87 (d, J=8.4 Hz, 1 H), 7.94 (s, 1 H), 8.40 (s, 1 H). 5H-indolo[2,1-a][2]benzazepine-10-carboxylic acid, 13-cyclohexyl-6-[1-[(tetrahydro-2H-pyran-4-yl)methyl]-1H-tetrazol-5-yl]-: 3 mg, 6% yield. MS m/z 524 (MH$^+$), $^1$H NMR (300 MHz, CD$_3$OD) δ ppm 1.18-1.70 (m, 6H), 1.79 (m, 2H), 1.84-2.21 (m, 7H), 3.11 (m, 1 H), 3.41 (m, 2H), 3.70 (broad m, 1 H), 4.01 (m, 2H), 4.12 (broad m, 1H), 4.52 (m, 2H), 7.32-7.38 (m, 2 H), 7.43-7.48 (m, 2 H), 7.99 (t, J=8.4, 8.4 Hz, 2 H), 8.21 (s, 1 H), 8.36 (s, 1 H).

EXAMPLE 15

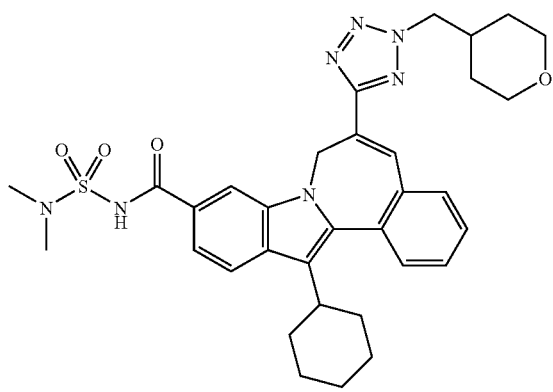

13-cyclohexyl-N-[(dimethylamino)sulfonyl]-6-[2-[(tetrahydro-2H-pyran-4-yl)methyl]-2H-tetrazol-5-yl]-7H-indolo[2,1-a][2]benzazepine-10-carboxamide. To a solution of 7H-indolo[2,1-a][2]benzazepine-10-carboxylic acid, 13-cyclohexyl-6-[2-[(tetrahydro-2H-pyran-4-yl)methyl]-2H-tetrazol-5-yl]-(100 mg, 0.19 mmol) in CH$_2$Cl$_2$ (1.0 mL) was added 2M oxalyl chloride (0.48 mL, 0.96 mmol). This solution was stirred at 22° C. for 3 hr and then concentrated under reduced pressure. BEMP (0.22 mL, 0.76 mmol), CH$_2$Cl$_2$ (1.0 mL) and N,N-dimethylsulfamide (120 mg, 0.96 mmol) was added to the resulting oil. The resulting mixture was stirred for 6 hr at 22° C. 1M HCl (15 mL) was added and the aqueous layer was extracted with CHCl$_3$ (2×30 mL). The organic phase was dried over Na$_2$SO$_4$, filtered, and concentrated under reduced pressure. This oil was purified by reverse-phase prep HPLC to afford the title compound (41 mg, 34%) as a yellow paste. MS m/z 631 (MH$^+$), $^1$H NMR (300 MHz, CD$_3$OD) δ ppm 1.17-1.71 (m, 6H), 1.78 (m, 2H), 1.86-2.20 (m, 7H), 2.89 (m, 1 H), 3.11 (s, 6H), 3.40 (m, 2H), 3.97 (m, 2H), 4.52 (broad m, 3 H), 5.99 (broad m, 1 H), 7.49-7.55 (m, 3 H), 7.62 (d, J=7.6 Hz, 1 H), 7.69 (d, J=8.4 Hz, 1 H), 7.85 (d, J=8.4 Hz, 1 H), 7.92 (s, 1 H), 8.38 (s, 1 H), 8.71 (broad s, 1H).

EXAMPLE 16

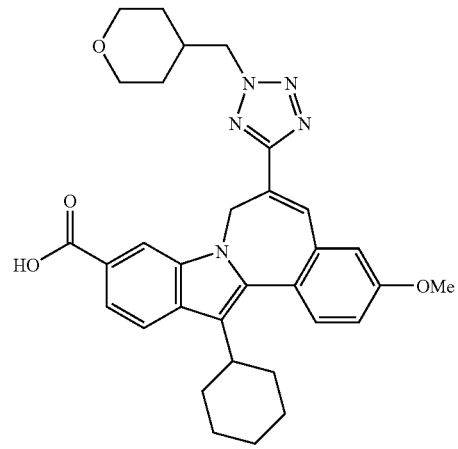

13-cyclohexyl-3-methoxy-6-[2-[(tetrahydro-2H-pyran-4-yl)methyl]-2H-tetrazol-5-yl]-7H-indolo[2,1-a][2]benzazepine-10-carboxylic acid. 7H-indolo[2,1-a][2]benzazepine-10-carboxylic acid, 13-cyclohexyl-3-methoxy-6-[2-[(tetrahydro-2H-pyran-4-yl)methyl]-2H-tetrazol-5-yl]- was made in an analogous fashion to 7H-indolo[2,1-a][2]benzazepine-10-carboxylic acid, 13-cyclohexyl-6-[2-[(tetrahydro-2H-pyran-4-yl)methyl]-2H-tetrazol-5-yl]- (see above) to yield 110 mg (90% yield final step) of a yellow solid. MS m/z 555 (MH$^+$), $^1$H NMR (300 MHz, CD$_3$OD) δ ppm 1.18-1.69 (m, 6H), 1.81 (m, 2H), 1.92-2.38 (m, 7H), 2.89 (m, 1 H), 3.46 (m, 2H), 3.95 (s, 3H), 3.99 (m, 2H), 4.52 (broad m, 1H), 4.56 (m, 2 H), 5.89 (broad m, 1 H), 7.05 (s, 1 H), 7.11 (d, J=8.4 Hz, 1 H), 7.58 (d, J=8.4 Hz, 1 H), 7.79 (d, J=7.8 Hz, 1 H), 7.88 (d, J=7.8 Hz, 1 H), 7.94 (s, 1 H), 8.44 (s, 1 H).

EXAMPLE 17

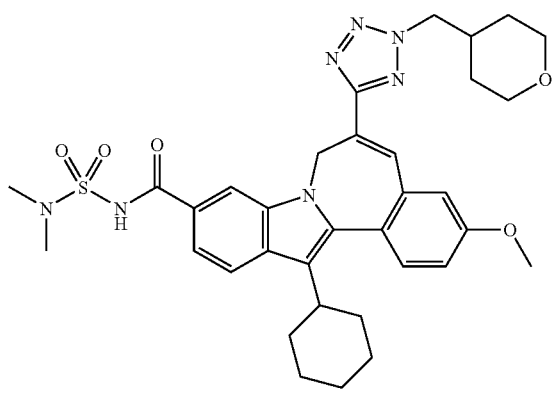

13-cyclohexyl-N-[(dimethylamino)sulfonyl]-3-methoxy-6-[2-[(tetrahydro-2H-pyran-4-yl)methyl]-2H-tetrazol-5-yl]-7H-indolo[2,1-a][2]benzazepine-10-carboxamide. To a solution of 7H-indolo[2,1-a][2]benzazepine-10-carboxylic acid, 13-cyclohexyl-3-methoxy-6-[2-[(tetrahydro-2H-pyran-4-yl)methyl]-2H-tetrazol-5-yl]- (110 mg, 0.20 mmol) in CH$_2$Cl$_2$ (1.0 mL) was added 2M oxalyl chloride (0.50 mL, 1.00 mmol). This solution was stirred at 22° C. for 3 hr and then concentrated under reduced pressure. BEMP (0.23 mL, 0.80 mmol), CH$_2$Cl$_2$ (1.0 mL) and N,N-dimethylsulfamide (124 mg, 1.00 mmol) was added to the resulting oil. The resulting mixture was stirred for 6 hr at 22° C. 1M HCl (15 mL) was added and the aqueous layer was extracted with CHCl$_3$ (2×30 mL). The organic phase was dried over Na$_2$SO$_4$, filtered, and concentrated under reduced pressure. This oil was purified by reverse-phase prep HPLC to afford the title compound (84 mg, 64%) as a yellow paste. MS m/z 661 (MH$^+$), $^1$H NMR (300 MHz, CD$_3$OD) δ ppm 1.18-1.69 (m, 6H), 1.79 (m, 2H), 1.93-2.40 (m, 7H), 2.89 (m, 1 H), 3.09 (s, 6H), 3.42 (m, 2H), 3.93 (s, 3H), 3.96 (m, 2H), 4.52 (broad m, 1H), 4.56 (m, 2 H), 5.92 (broad m, 1 H), 7.05 (s, 1 H), 7.09 (d, J=8.4 Hz, 1 H), 7.58 (d, J=8.4 Hz, 1 H), 7.78 (d, J=7.8 Hz, 1 H), 7.86 (d, J=7.8 Hz, 1 H), 7.90 (s, 1 H), 8.47 (s, 1 H), 8.69 (broad s, 1 H).

EXAMPLE 18

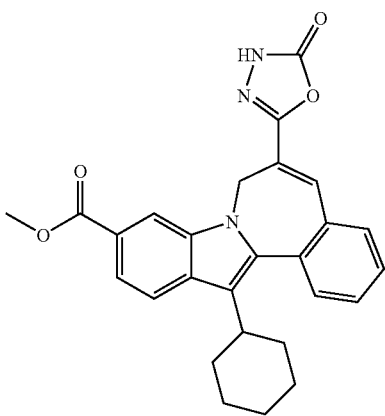

13-cyclohexyl-6-(4,5-dihydro-5-oxo-1,3,4-oxadiazol-2-yl)-7H-indolo[2,1-a][2]benzazepine-10-carboxylic acid, methyl ester. The hydrazide (771 mg, 1.80 mMol) 7H-indolo[2,1-a][2]benzazepine-6,10-dicarboxylic acid, 13-cyclohexyl-, 10-methyl ester, 6-hydrazide was partially dissolved in 18 ml of THF and diisopropylethyl amine (DIEA) (0.34 mL, 1.95 mMol) added and stirred for 5 min then 1,1'-carbonyldiimidazole (CDI) (316 mg, 1.95 mMol) was added and the reaction stirred overnight under nitrogen at room temperature. An additional 100 mg of CDI and 0.1 ml of DIEA was added to drive the reaction to completion. The reaction was partitioned between ethyl acetate and 0.1N hydrochloric acid. The organic phase washed with 0.1N hydrochloric acid, brine, and dried over magnesium sulfate to yield 0.82 g of product. 1H NMR (500 MHz, CHLOROFORM-D) δ ppm 9.43 (s, 1 H) 8.20 (s, 1 H) 7.79 (d, J=8.54 Hz, 1 H) 7.67 (d, J=8.54 Hz, 1 H) 7.61 (d, J=7.63 Hz, 1 H) 7.54 (t, J=7.32 Hz, 1 H) 7.43-7.51 (m, 2 H) 7.41 (s, 1 H) 5.44 (d, J=13.43 Hz, 1 H) 4.00 (d, J=15.87 Hz, 1 H) 3.90 (s, 3 H) 2.80 (t, J=15.87 Hz, 1 H) 2.00-2.17 (m, 2 H) 1.89 (d, J=41.20 Hz, 2 H) 1.51-1.80 (m, 3 H) 1.28-1.53 (m, 4 H) 1.11-1.22 (m, 1 H); MS m/z 456(MH$^+$), MS m/z 454(M-H)$^-$.

EXAMPLE 19

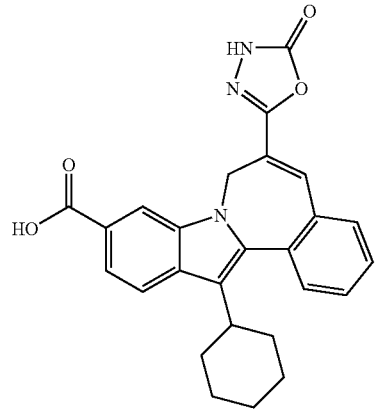

13-cyclohexyl-6-(4,5-dihydro-5-oxo-1,3,4-oxadiazol-2-yl)-7H-indolo[2,1-a][2]benzazepine-10-carboxylic acid. 7H-indolo[2,1-a][2]benzazepine-10-carboxylic acid, 13-cyclohexyl-6-(4,5-dihydro-5-oxo-1,3,4-oxadiazol-2-yl)-, methyl ester (91 mg, 0.20 mMol) was suspended in 5 ml of acetic acid and 2.5 ml of 48% aqueous hydrobromic acid added. The reaction was heated to 111 C for 4 hours. The reaction cooled and a yellow precipitate filtered off and rinsed with a small amount of acetic acid, then water. The product was dried in vacuuo at room temperature to yield 75 mg of product. 1H NMR (500 MHz, CHLOROFORM-D, MeOD) δ ppm 8.17 (s, 1 H) 7.75 (d, J=8.54 Hz, 1 H) 7.61 (d, J=8.55 Hz, 1 H) 7.48 (d, J=7.32 Hz, 1 H) 7.35-7.44 (m, 3 H) 7.30 (s, 1 H) 5.52 (d, J=12.82 Hz, 1 H) 4.18 (d, J=8.85 Hz, 1 H) 2.65-2.78 (m, 1 H) 1.89-2.04 (m, 2 H) 1.71-1.85 (m, 1 H) 1.63 (d, J=10.99 Hz, 2 H) 1.16-1.49 (m, 3 H) 1.11 (s, 2 H); MS m/z 442(MH$^+$).

EXAMPLE 20

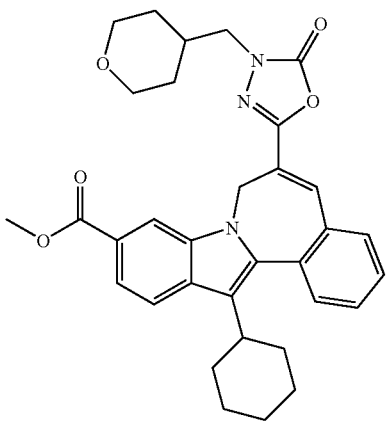

13-cyclohexyl-6-[4,5-dihydro-5-oxo-4-[(tetrahydro-2H-pyran-4-yl)methyl]-1,3,4-oxadiazol-2-yl]-7H-indolo[2,1-a][2]benzazepine-10-carboxylic acid, methyl ester. 7H-indolo[2,1-a][2]benzazepine-10-carboxylic acid, 13-cyclohexyl-6-(4,5-dihydro-5-oxo-1,3,4-oxadiazol-2-yl)-, methyl ester (203 mg, 0.45 mMol) was dissolved in a mixture of 2 ml DMF and 1 ml THF with heating. To the reaction was added 4-(bromomethyl)tetrahydropyran (115 mg, 0.64 mMol), cesium carbonate (201 mg, 0.62 mMol) and sodium iodide (90 mg, 0.6 mMol) was added. The reaction was capped and heated to 60 C overnight. The reaction contents were transferred to a 25 ml Erlenmeyer flask and water added with rapid stirring. A bright yellow precipitate was filtered off and rinsed with water and air dried to yield 236 mg of material (95%). 1H NMR (500 MHz, CHLOROFORM-D) δ ppm 8.32 (s, 1 H) 7.88 (d, J=8.55 Hz, 1 H) 7.74 (dd, J=8.55, 1.22 Hz, 1 H) 7.62 (d, J=7.02 Hz, 1 H) 7.48-7.56 (m, 3 H) 7.43 (s, 1 H) 5.64 (d, J=13.12 Hz, 1 H) 4.31 (d, J=14.95 Hz, 1 H) 3.88-4.02 (m, 5 H) 3.67 (s, 2 H) 3.25-3.44 (m, 2 H) 2.77-2.87 (m, 1 H) 1.88-2.21 (m, 5 H) 1.70-1.82 (m, 2 H) 1.50-1.70 (m, 4 H) 1.11-1.50 (m, 6 H); MS m/z 554(MH$^+$)

EXAMPLE 21

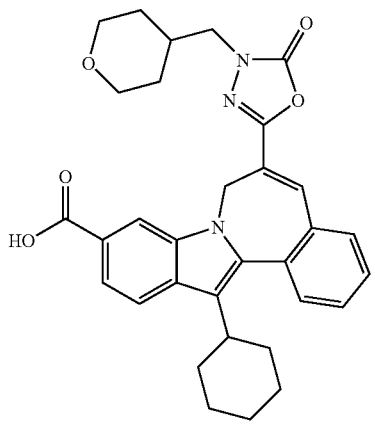

13-cyclohexyl-6-[4,5-dihydro-5-oxo-4-[(tetrahydro-2H-pyran-4-yl)methyl]-1,3,4-oxadiazol-2-yl]-7H-indolo[2,1-a][2]benzazepine-10-carboxylic acid. 7H-indolo[2,1-a][2]benzazepine-10-carboxylic acid, 13-cyclohexyl-6-[4,5-dihydro-5-oxo-4-[(tetrahydro-2H-pyran-4-yl)methyl]-1,3,4-oxadiazol-2-yl]-, methyl ester (225 mg, 0.41 mMol) was suspended in 5 ml of acetic acid and 2.5 ml of 48% aqueous hydrobromic acid was added. The reaction was heated to 100 C for 2 hrs and then to 120 C for 1.5 hrs and finally to 130 C for an additional 3 hours then allow to cool overnight. Filter off yellow solid from reaction mixture (55 mg) whose major component by HPLC analysis was starting material. The filtrate was diluted with 50 ml of water and extracted with ethyl acetate. The organic phase was washed with water, then brine and dried over magnesium sulfate. The crude product residue was isolated by removal of volatiles in vacuuo. The crude product was dissolved in an acetonitrile\DMF mixture and purified by reverse phase HPLC under the following conditions: Shimadzu prep. HPLC using Discovery VP software: % A=10% methanol, 90% water, 0.1% TFA; % B=90% methanol, 10% water, 0.1% TFA Initial % B=35; Final % B=100; Gradient=30 min; Runtime=40 min Flow rate=20 ml/min; Wavelength=220 nm; Column=YMC Pro Pack 20 mm×150 mm S5. 1H NMR (500 MHz, CHLOROFORM-D) δ ppm 8.40 (s, 1 H) 7.92 (d, J=8.54 Hz, 1 H) 7.82 (d, J=8.55 Hz, 1 H) 7.63 (d, J=7.63 Hz, 1 H) 7.47-7.58 (m, 3H) 7.44 (s, 1 H) 5.66 (d, J=14.95 Hz, 1 H) 4.33 (d, J=14.65 Hz, 4 H) 3.87-4.13 (m, 2 H) 3.72 (dd, J=29.76, 5.95 Hz, 2 H) 3.26-3.52 (m, 2 H) 2.78-2.93 (m, 1 H) 2.14-2.26 (m, 1 H) 1.86-2.12 (m, 4 H) 1.31-1.84 (m, 9 H) 1.12-1.32 (m, 1 H); MS m/z 538(M-H)$^-$.

EXAMPLE 22

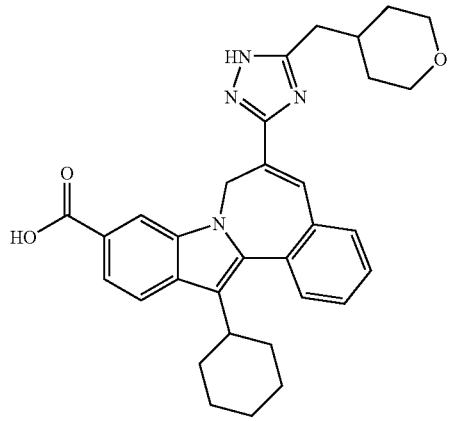

13-cyclohexyl-6-[3-[(tetrahydro-2H-pyran-4-yl)methyl]-1H-1,2,4-triazol-5-yl]-7H-indolo[2,1-a][2]benzazepine-10-carboxylic acid. The synthesis 7H-indolo[2,1-a][2]benzazepine-10-carboxylic acid, 13-cyclohexyl-6-[3-[(tetrahydro-2H-pyran-4-yl)methyl]-1H-1,2,4-triazol-5-yl]- was preformed using the literature procedure: Kap-Sun Yeung, Michelle E. Farkas, John F. Kadow and Nicholas A. Meanwell; Tetrahedron Letters, 46 (2005 H 3429-3432. In a 2 ml microwave reaction tube the following reagents were combined in 0.47 ml of n-butanol: 7H-indolo[2,1-a][2]benzazepine-6,10-dicarboxylic acid, 13-cyclohexyl-, 10-methyl ester, 6-hydrazide (100 mg, 0.23 mMol), 4-cyanomethyltetrahydropyran (88.3 mg, 0.71 mMol), potassium carbonate (16.6 mg, 0.12 mMol). The reaction was heated in a microwave at 150 C for 7 hours. The intermediate n-butyl ester was identified by LC/MS m/z 579(MH$^+$) Volatiles from the reaction were removed in vacuuo and crude reaction mixture subject to hydrolysis conditions of 10 ml acetic acid, 5 ml 48% aqueous hydrobromic acid at 80 to 100 C for 4 hours to yield the final product. Volatiles from the reaction mixture were removed in vacuuo and the residue dissolved in DMF/methanol for isolation by preparative HPLC using the following conditions: two 2 ml injections on: Shimadzu prep. HPLC using Discovery VP software: % A=10% methanol, 90% water, 0.1% TFA; % B=90% methanol, 10% water, 0.1% TFA; Initial % B=35; Final % B=100; Gradient=30 min; Runtime=40 min; Flow rate=20 ml/min; Column=YMC Pro Pack 20 mm×150 mm S5. Product peaks identified by LC/MS-MS m/z 442(MH+) and combined to yield 25.2 mg. $^1$H NMR (500 MHz, CHLOROFORM-D, MeOD) δ ppm 8.35 (s, 1 H) 7.78 (d, J=8.55 Hz, 3 H) 7.59-7.67 (m, 2 H) 7.53 (dd, J=5.65, 3.51 Hz, 1 H) 7.44-7.49 (m, 1 H) 7.35-7.43 (m, 2 H) 5.89 (d, J=15.26 Hz, 1 H) 4.29 (d, J=14.34 Hz, 1 H) 3.84 (dd, J=11.90, 3.05 Hz, 2 H) 2.80 (t, J=11.44 Hz, 1 H) 2.63 (d, J=7.32 Hz, 2 H) 1.60-2.18(m, 8 H) 1.48-1.60(m, 2 H) 1.08-1.41 (m, 6 H).

EXAMPLE 23

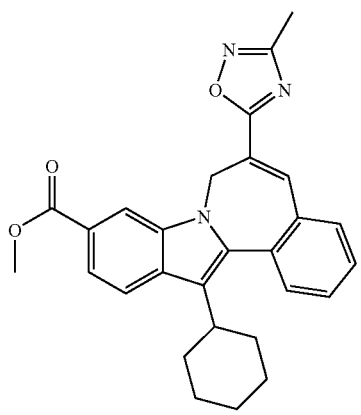

13-cyclohexyl-6-(3-methyl-1,2,4-oxadiazol-5-yl)-7H-indolo[2,1-a][2]benzazepine-10-carboxylic acid, methyl ester. The 1,2,4-oxadiazole ring structure can be synthesized according to the literature procedure of Ying Wang and Regan L. Miller et. al. Organic Letters 7 (5 H 2005 p. 925-928.7H-indolo[2,1-a][2]benzazepine-10-carboxylic acid, 6-(chlorocarbonyl)-13-cyclohexyl-, methyl ester 250 mg, 0.58 mMol) was taken dissolved in 4.4 ml of anhydrous THF. Acetamide oxime (48 mg, 0.65 mMol) and Diisopropylethyl Amine (0.2 mL, 1.15 mMol) was added to the reaction in a 5 ml microwave reactor tube. The reaction was capped under nitrogen and heated in a microwave at 150 C for 15 minutes. Additional Acetamide oxime (12.8 mg, 0.17 mMol) was added to the reaction and heated at 150 C for 10 minutes. The reaction was partitioned between ethyl acetate and 1 N hydrochloric acid. The organic phase was then washed with 1N hydrochloric acid, brine and dried over magnesium sulfate to yield 244 mg of crude product. Pure product (105 mg, 40%) was isolated from silica gel chromatography eluting with dichlormethane. 1H NMR (500 MHz, CHLOROFORM-D) δ ppm 8.36 (s, 1 H) 7.92 (s, 1 H) 7.88 (d, J=8.24 Hz, 1 H) 7.75 (d, J=8.55 Hz, 1 H) 7.60-7.66 (m, 1 H) 7.47-7.59 (m, 3 H) 5.85 (s, 1 H) 4.48 (s, 1 H) 3.96 (s, 3 H) 2.85 (t, J=11.75 Hz, 1 H) 2.44 (s, 3 H) 1.84-2.21 (m, 4 H) 1.77 (d, J=7.93 Hz, 2 H) 1.31-1.48 (m, 3H) 1.15-1.29 (m, 1 H); MS m/z 454(MH+).

EXAMPLE 24

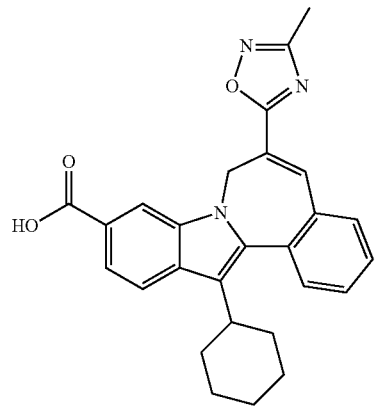

13-cyclohexyl-6-(3-methyl-1,2,4-oxadiazol-5-yl)-7H-indolo[2,1-a][2]benzazepine-10-carboxylic acid. 7H-indolo[2,1-a][2]benzazepine-10-carboxylic acid, 13-cyclohexyl-6-(3-methyl-1,2,4-oxadiazol-5-yl)-, methyl ester (97 mg, 0.21 mMol) was dissolved in 2.5 ml of pyridine along with lithium iodide (91 mg, 0.68 mMol). The reaction was heated to 180 C for 2 hrs in a microwave. Reaction volatiles were then removed in vacuuo and the residue partitioned between ethyl acetate and 1 N hydrochloric acid. The organic phase was washed with 1N hydrochloric acid, Brine and dried over magnesium sulfate. Pure product (42 mg, 45%) was isolated by silica gel chromatography by elution with 5% methanol in dichloromethane. 1H NMR (500 MHz, CHLOROFORM-D) δ ppm 8.46 (s, 1 H) 7.88-8.02 (m, 2 H) 7.83 (d, J=7.32 Hz, 1 H) 7.61-7.70 (m, 1 H) 7.48-7.61 (m, 3 H) 5.89 (s, 1 H) 4.49 (s, 1 H) 2.86 (t, J=11.44 Hz, 1 H) 2.47 (s, 3 H) 1.86-2.29 (m, 4 H) 1.78(d, J=7.63 Hz, 2 H) 1.31-1.51 (m, 2 H) 1.13-1.32(m, 2 H); MS m/z 440(MH+); MS m/z 438(M-H)−.

EXAMPLE 25

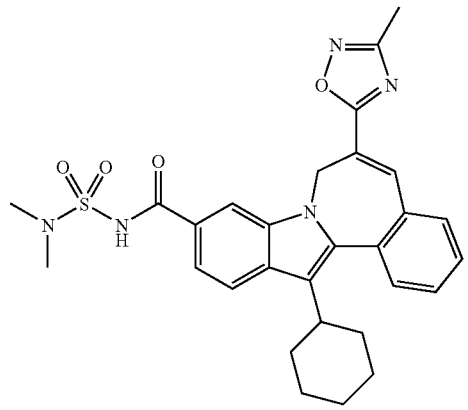

13-cyclohexyl-N-[(dimethylamino)sulfonyl]-6-(3-methyl-1,2,4-oxadiazol-5-yl)-7H-indolo[2,1-a][2]benzazepine-10-carboxamide. 7H-indolo[2,1-a][2]benzazepine-10-carboxylic acid, 13-cyclohexyl-6-(3-methyl-1,2,4-oxadiazol-5-yl)- (38 mg, 0.086 mMol) was placed in a 25 ml round bottom flask and 2 ml of 2.0M oxalyl chloride in dichloromethane added, followed by 1 drop of DMF. The reaction was briefly heated to reflux then stirred at room temperature for 2 hrs. Volatiles were removed in vacuuo and the residue acid chloride was dissolved in 1 ml of anhydrous THF and added dropwise over 7 minutes to the preformed anion of N,N-dimethylsulfamide prepared as follows: N,N-dimethylsulfamide (35.9 mg, 0.289 mMol) was dissolved in 0.4 ml of anhydrous THF and 2-tert-butylimino-2-diethylamino-1,3-dimethylperhydro-1,3,2-diazaphosphorine (62 uL, 0.214 mMol) was added and the reaction stirred for 10 minutes at room temperature under nitrogen. The reaction was allow to proceed at room temperature under inert atmosphere for 1 hour. The reaction mixture was partitioned between 0.1N hydrochloric acid and 30 mL of ethyl acetate. The organic phase washed with 0.1N hydrochloric acid, brine and dried over magnesium sulfate. Volatiles removed in vacuuo and the residue dissolved in acetonitrile and purified by preparative HPLC using the following conditions to yield 26.8 mg (57%) of pure product as a yellow solid. Shimadzu prep. HPLC using Discovery VP software: % A=10% acetonitrile, 90% water, 0.1% TFA % B=90% acetonitrile, 10% water, 0.1% TFA; Initial % B=30; Final % B=100; Gradient=15 min; Runtime=25 min; Flow rate=25 ml/min; Wavelength=220 nm; Column=Phenonenex Luna 21.2 mm×100 mm s10. 1H NMR (500 MHz, CHLOROFORM-D) δ ppm 8.60 (s, 1 H) 8.19 (s, 1 H) 7.89-7.95 (m, 2 H) 7.61-7.66 (m, 1 H) 7.50-7.61 (m, 3 H) 7.47 (dd, J=8.55, 1.53 Hz, 1 H) 5.81 (s, 1 H) 4.50 (s, 1 H) 3.08 (s, 6 H) 2.80-2.91 (m, 1 H) 2.45 (s, 3 H) 1.84-2.18 (m, 4 H) 1.77 (d, J=10.68 Hz, 2 H) 1.10-1.62 (m, 5 H); MS m/z 546(MH+).)

EXAMPLE 26

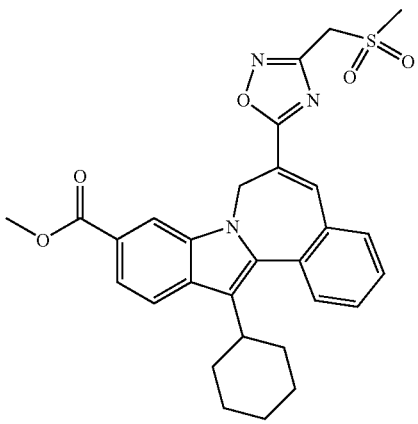

13-cyclohexyl-6-[3-[(methylsulfonyl)methyl]-1,2,4-oxadiazol-5-yl-]7H-indolo[2,1-a][2]benzazepine-10-carboxylic acid, methyl ester. 7H-indolo[2,1-a][2]benzazepine-10-carboxylic acid, 6-(chlorocarbonyl)-13-cyclohexyl-, methyl ester (776 mg, 1.79 mMol) was dissolved in 13 ml of anhydrous THF in a 20 ml microwave vessel. N-hydroxy-2-(methylsulfonyl)ethanimidamide (308 mg, 2.02 mMol) was added to the reaction along with diisopropylethyl amine (0.64 ml, 3.67 mMol). The reaction was stirred for 5 minutes at room temperature then heated in the microwave at 150 C for 15 minutes. The reaction was partitioned between 0.1N hydrochloric acid and ethyl acetate, washed with brine and dried over magnesium sulfate. The residue was chromatographed on silica gel and the product eluted with 2% ethyl acetate in dichloromethane to yield 287 mg (30%). 1H NMR (500 MHz, CHLOROFORM-D) δ ppm 1.13-1.23 (m, 1 H) 1.29-1.64 (m, 5 H) 1.77 (d, J=9.77 Hz, 2 H) 1.87-2.00 (m, 1 H) 2.04-2.17 (m, 2 H) 2.79-2.90 (m, 1 H) 3.23 (s, 3 H) 3.94 (s, 3 H) 4.47 (s, 2 H) 4.51 (d, J=14.04 Hz, 1 H) 5.84 (d, J=11.29 Hz, 1 H) 7.51-7.62 (m, 3 H) 7.62-7.67 (m, 1 H) 7.70-7.78 (m, 1 H) 7.88 (d, J=8.24 Hz, 1 H) 7.99 (s, 1 H) 8.30 (s, 1 H); MS m/z 532(MH+).

EXAMPLE 27

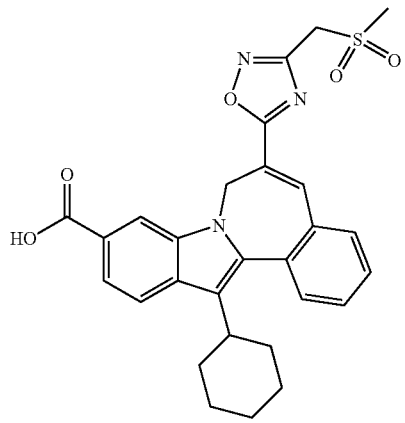

13-cyclohexyl-6-[3-[(methylsulfonyl)methyl]-1,2,4-oxadiazol-5-yl]-7H-indolo[2,1-a][2]benzazepine-10-carboxylic acid. 7H-indolo[2,1-a][2]benzazepine-10-carboxylic acid, 13-cyclohexyl-6-[3-[(methylsulfonyl)methyl]-1,2,4-oxadiazol-5-yl]-, methyl ester (193 mg, 0.36 mMol) was dissolved in 3.6 ml of pyridine in microwave tube. Lithium iodide (166 mg, 1.24 mMol) was added and the reaction was placed under nitrogen and heated to 180 C in a microwave for 1 hr. The reaction was partitioned between ethyl acetate and 0.1N hydrochloric acid and brine was added to aid in phase separation. The organic layer was washed with 0.1N hydrochloric acid/brine mixture, dried over magnesium sulfate and volatiles removed in vacuuo to yield 180 mg of a brown solid. The crude reaction product was combined with 73 mg of crude reaction product from a previous trial experiment and purified by silica gel chromatography eluting with 5% methanol in dichloromethane to yield 75 mg (29%) of product. A separate less pure fraction (13.6 mg) was further purified by Prep HPLC under the following conditions: Shimadzu prep. HPLC using Discovery VP software: % A=10% acetonitrile, 90% water, 0.1% TFA; % B=90% acetonitrile, 10% water, 0.1% TFA; Initial % B=30; Final % B=100; Gradient=15 min Runtime=20 min; Flow rate=25 ml/min; Wavelength=220 nm; Column=Phenonenex Luna 21.2 mm×100 mm s10. Product retention time=13.0 min, 5.9 mg product recovered. 1H NMR (500 MHz, CHLOROFORM-D) δ ppm 1.13-1.52 (m, 4 H) 1.53-1.85 (m, 3 H) 1.86-2.23 (m, 4 H) 2.82-2.91 (m, 1 H) 3.29 (s, 3 H) 4.44-4.65 (m, 3 H) 5.89 (d, J=12.21 Hz, 1 H) 7.52-7.65 (m, 3 H) 7.64-7.70 (m, 1 H) 7.83 (d, J=8.55 Hz, 1 H) 7.94 (d, J=8.55 Hz, 1 H) 8.00 (s, 1 H) 8.39 (s, 1 H); MS m/z 518(MH+).

EXAMPLE 28

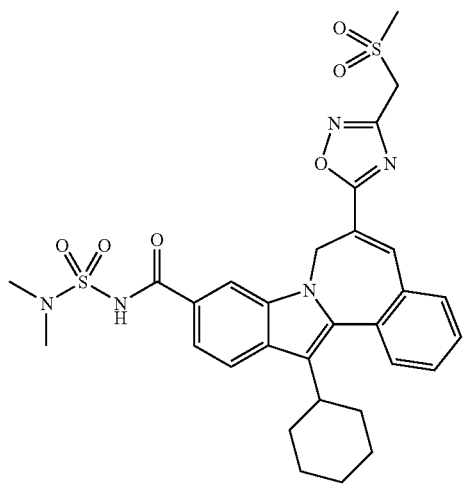

13-cyclohexyl-N-[(dimethylamino)sulfonyl]-6-[3-[(methylsulfonyl)methyl]-1,2,4-oxadiazol-5-yl]-7H-indolo[2,1-a][2]benzazepine-10-carboxamide. 7H-indolo[2,1-a][2]benzazepine-10-carboxylic acid, 13-cyclohexyl-6-[3-[(methylsulfonyl)methyl]-1,2,4-oxadiazol-5-yl]- (75 mg, 0.13 mMol) was dissolved in 1.5 ml of THF, and carbonyldiimidazole (27.7 mg, 0.17 mMol) was added. The reaction was stirred for 40 minutes at room temperature under a nitrogen atmosphere then heated to reflux for 40 minutes. The reaction was cooled to room temperature under nitrogen and N,N-dimethylsulfamide (84 mg, 0.68 mMol) added along with 22 uL (0.15 mMol) of DBU. The reaction was stirred overnight (~16 hr) at room temperature, then partitioned between ethyl acetate and 0.1N hydrochloric acid, washed with 0.1N hydrochloric acid, brine, and dried over magnesium sulfate. Volatiles were removed in vacuuo and the residue purified by Prep. HPLC under the following conditions: Shimadzu prep. HPLC using Discovery VP software: % A=10% acetonitrile, 90% water, 0.1% TFA; % B=90% acetonitrile, 10% water, 0.1% TFA; Initial % B=30; Final % B=100; Gradient=15 min; Runtime=20 min Flow rate=40 ml/min; Wavelength=220 nm; Column=Waters Sunfire 30 mm×100 mm S5. Product retention time=13.3 min, 45.3 mg (51%) product recovered. 1H NMR (500 MHz, CHLOROFORM-D) δ ppm 1.10-1.50 (m, 3 H) 1.50-1.65 (m, 1 H) 1.69-1.83 (m, 2 H) 1.85-2.16 (m, 7 H) 2.79-2.92 (m, 1 H) 3.07 (s, 6 H) 3.22 (s, 3 H) 4.51 (s, 3 H) 5.84 (d, J=11.60 Hz, 1 H) 7.47 (d, J=8.24 Hz, 1 H) 7.52-7.64 (m, 3 H) 7.63-7.69 (m, 1 H) 7.91 (d, J=8.55 Hz, 1 H) 7.95 (s, 1 H) 8.13 (s, 1 H) 8.83 (s, 1 H); MS m/z 624(MH+).

EXAMPLE 29

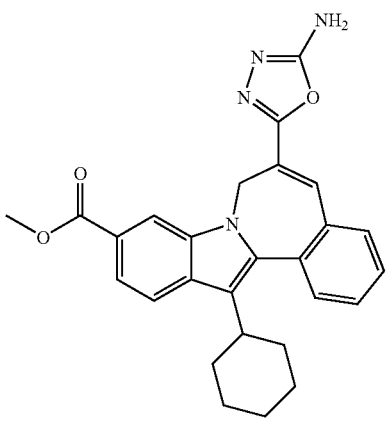

6-(5-amino-1,3,4-oxadiazol-2-yl)-13-cyclohexyl-7H-indolo[2,1-a][2]benzazepine-10-carboxylic acid, methyl ester. To a suspension of 7H-indolo[2,1-a][2]benzazepine-6,10-dicarboxylic acid, 13-cyclohexyl-, 10-methyl ester, 6-hydrazide (1.01 g, 2.35 mMol) in 20 ml of 1,4-dioxane was added sodium bicarbonate (203 mg, 2,42 mMol) in 5.3 ml of water. The reaction was stirred for 20 minutes at room temperature then cyanogen bromide (256 mg, 2.42 mMol) added to the reaction. The reaction was capped and stirred for 18 hrs at room temperature after which cyanogen bromide (35 mg, 0.33 mMol) was added. The reaction was stirred for an additional 6 hours at room temperature. The reaction was filtered and rinsed with water and the precipitate dried in vacuuo to yield 880 mg (82%) of product. 1H NMR (500 MHz, DMSO-D6) δ ppm 8.21 (s, 1 H) 7.93 (d, J=8.55 Hz, 1 H) 7.63-7.69 (m, 2 H) 7.53-7.62 (m, 3 H) 5.74 (d, J=13.43 Hz, 1 H) 4.39 (d, J=14.95 Hz, 1H) 3.89 (s, 3 H) 2.73-2.87 (m, 1 H) 1.94-2.12 (m, 3 H) 1.84-1.94 (m, 1 H) 1.70 (d, J=6.71 Hz, 2 H) 1.32-1.48 (m, 3 H) 1.06-1.18 (m, 1 H); MS m/z 455(MH+), MS m/z 453(M-H)−.

EXAMPLE 30

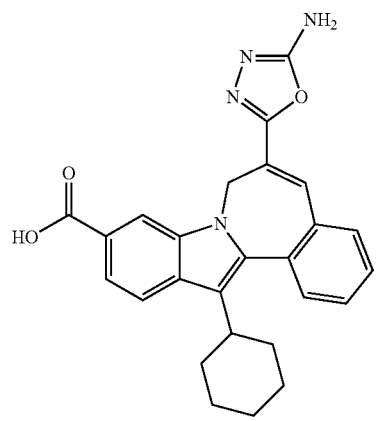

6-(5-amino-1,3,4-oxadiazol-2-yl)-13-cyclohexyl-7H-indolo[2,1-a][2]benzazepine-10-carboxylic acid. 7H-indolo[2,1-a][2]benzazepine-10-carboxylic acid, 6-(5-amino-1,3,4-oxadiazol-2-yl)-13-cyclohexyl-, methyl ester (27.7 mg, 0.061 mMol) was suspended in 0.6 ml of THF, and 0.2 ml of 1.0M tetrabutylammonium hydroxide in methanol was added to the reaction. Upon addition of the tetrabutylammonium hydroxide solution the reaction became homogenous. The reaction was stirred at room temperature for 16 hours resulting on only partial conversion to product. The reaction was heated to 60 C for 2 hours then cooled and 1N hydrochloric acid and DMF added. The solution was injected on a prep HPLC to isolate 7.4 mg of product using the following conditions: Shimadzu prep. HPLC using Discovery VP software: % A=10% methanol, 90% water, 0.1% TFA; % B=90% methanol, 10% water, 0.1% TFA; Initial % B=35; Final % B=100; Gradient=30 min; Runtime=50 min; Flow rate=20 ml/min; Column=YMC Pro Pack 20 mm×150 mm S5. 1H NMR (500 MHz, DMF) δ ppm 12.90 (s, 1 H) 8.38-8.41 (m, 1 H) 7.70-7.78 (m, 3 H) 7.63-7.69 (m, 1 H) 7.59-7.63 (m, 1 H) 7.45 (s, 2 H) 7.40 (s, 1 H) 5.91 (d, J=17.09 Hz, 1 H) 4.51 (d, J=12.82 Hz, 1 H) 2.03-2.22 (m, 3 H) 1.92 (t, J=10.68 Hz, 1 H) 1.73 (d, J=7.02 Hz, 2 H) 1.39-1.52 (m, 3 H) 1.18 (d, J=12.82 Hz, 1 H) 0.84-0.91 (m, 1 H).

EXAMPLE 31

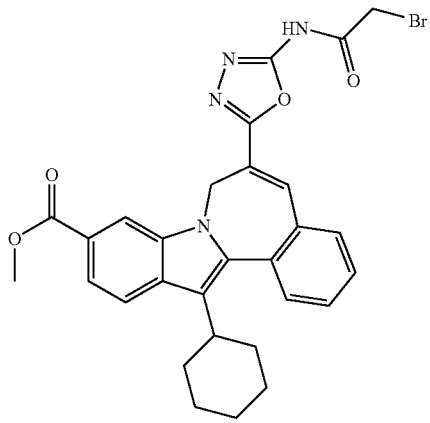

6-[5-[(bromoacetyl)amino]-1,3,4-oxadiazol-2-yl]-13-cyclohexyl-7H-indolo[2,1-a][2]benzazepine-10-carboxylic acid, methyl ester. 7H-indolo[2,1-a][2]benzazepine-10-carboxylic acid, 6-(5-amino-1,3,4-oxadiazol-2-yl)-13-cyclohexyl-, methyl ester (50.7 mg, 0.125 mMol) was suspended in 1.0 ml of THF, and pyridine (12 uL, 0.148 mMol) added. The reaction was cooled to 0 C under nitrogen then bromoacetyl bromide (13 uL, 0.15 mMol) added. The reaction was stirred at 0 C for 1 hr and warmed to room temperature over 30 minutes. The reaction was partitioned between water and organic consisting of ethyl acetate, THF and dichloromethane. The organic phase was washed with 0.1N hydrochloric acid, brine and dried over magnesium sulfate to yield 65 mg (90%) of product. 1H NMR (500 MHz, DMSO-D6) δ ppm 12.28 (s, 1 H) 8.25 (s, 1 H) 7.94 (d, J=8.55 Hz, 1 H) 7.74 (d, J=7.63 Hz, 1 H) 7.57-7.70 (m, 5 H) 5.80 (d, J=14.04 Hz, 1 H) 4.49 (d, J=11.90 Hz, 1 H) 4.17 (s, 2 H) 3.90 (s, 3 H) 2.74-2.86 (m, 1 H) 1.94-2.12 (m, 3 H) 1.82-1.95 (m, 1 H) 1.70 (d, J=7.32 Hz, 2 H) 1.36-1.50 (m, 3 H) 1.08-1.20 (m, 1 H); MS m/z 575(MH+); MS m/z 573(M-H)−.

EXAMPLE 32

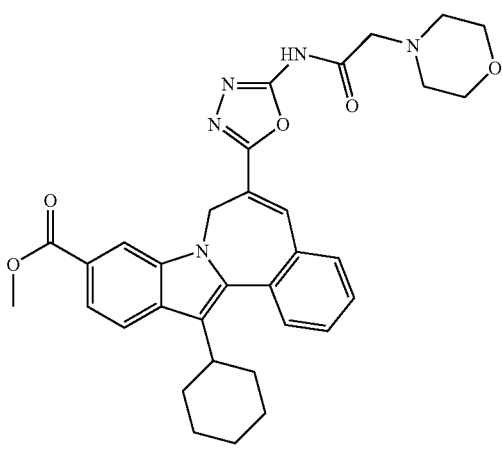

13-cyclohexyl-6-[5-[(4-morpholinylacetyl)amino]-1,3,4-oxadiazol-2-yl]-7H-indolo[2,1-a][2]benzazepine-10-carboxylic acid, methyl ester. 7H-indolo[2,1-a][2]benzazepine-10-carboxylic acid, 6-[5-[(bromoacetyl)amino]-1,3,4-oxadiazol-2-yl]-13-cyclohexyl-, methyl ester (62 mg, 0.11 mMol) was stirred in 1 ml of DMF and morpholine (28 uL, 0.32 mMol) added to the reaction. A small pea of sodium iodide was added to the reaction and the reaction capped, stirred at room temperature for 16 hrs. The reaction was partitioned between dichloromethane and saturated aqueous sodium bicarbonate. The organic layer dried over magnesium sulfate and volatiles removed to yield 67 mg of product. 1H NMR (500 MHz, CHLOROFORM-D) δ ppm 8.35 (s, 1 H) 7.86 (d, J=8.55 Hz, 1 H) 7.74 (d, J=8.54 Hz, 1 H) 7.58-7.66 (m, 2 H) 7.44-7.56 (m, 3 H) 5.81-5.98 (m, 1 H) 4.37-4.53 (m, 1 H) 3.94 (s, 3 H) 3.83 (s, 4 H) 2.69-2.87 (m, 5 H) 1.85-2.20 (m, 6 H) 1.34-1.86 (m, 14 H) 1.12-1.37 (m, 17 H) 0.74-0.94 (m, 9 H) Aliphatic region of NMR contains hydrocarbon (grease) contaminates not observed by HPLC; MS m/z 582 (MH+); MS m/z 580(M-H)−.

EXAMPLE 33

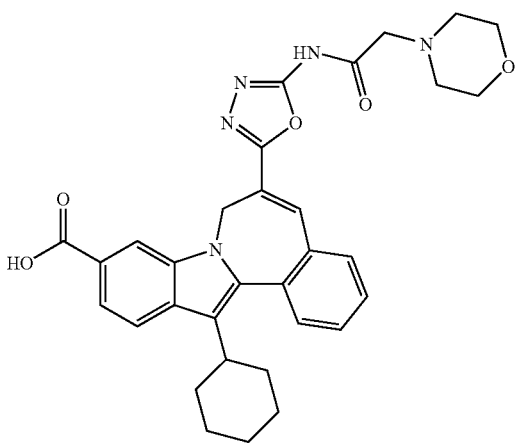

13-cyclohexyl-6-[5-[(4-morpholinylacetyl)amino]-1,3,4-oxadiazol-2-yl]-7H-indolo[2,1-a][2]benzazepine-10-carboxylic acid. 7H-indolo[2,1- ][2]benzazepine-10-carboxylic acid, 13-cyclohexyl-6-[5-[(4-morpholinylacetyl)amino]-1,3,4-oxadiazol-2-yl]-, methyl ester (60 mg, 0.10 mMol) was dissolved in 1 ml of anhydrous THF and potassium trimethylsilanoate (78 mg, 0.61 mMol) added. The reaction was capped and stirred at room temperature for 2.5 hours. Hydrochloric acid (6 ml of 0.1M) was added to the reaction and the product extracted into ethyl acetate. The organic layer was washed with brine and dried over magnesium sulfate. The residue was triturated with hot diethyl ether to yield 18.7 mg (32%) of product as a yellow solid. 1H NMR (500 MHz, DMSO-D6) δ ppm 12.64 (s, 1 H) 11.55 (s, 1 H) 8.23 (s, 1H) 7.91 (d, J=8.55 Hz, 1 H) 7.72 (d, J=7.63 Hz, 1 H) 7.51-7.69 (m, 5 H) 5.79 (d, J=13.12 Hz, 1 H) 4.48 (d, J=12.21 Hz, 1 H) 3.55 (s, 4 H) 2.72-2.91 (m, 1 H) 1.80-2.17 (m, 4 H) 1.61-1.81 (m, 2 H) 1.29-1.56 (m, 3 H) 1.03-1.22 (m, 1 H); MS m/z 568(MH+); MS m/z 566 (M-H)−.

EXAMPLE 34

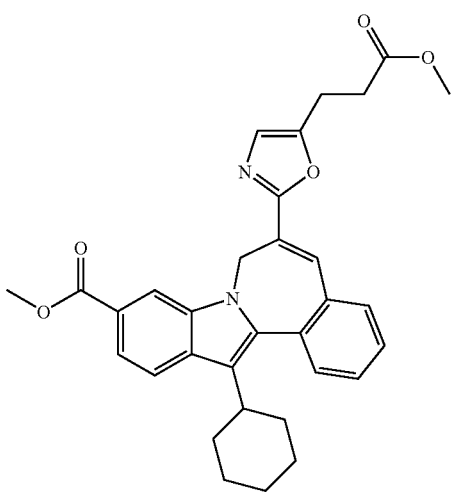

13-cyclohexyl-6-[5-(3-methoxy-3-oxopropyl)-2-oxazolyl]-7H-indolo[2,1-a][2]benzazepine-10-carboxylic acid, methyl ester. 7H-indolo[2,1-a][2]benzazepine-10-carboxylic acid, 13-cyclohexyl-6-[[(5-methoxy-2,5-dioxopentyl)amino]carbonyl]-, methyl ester, (0.25 g, 0.46 mMol) was dissolved in 4.6 ml of toluene and 93 uL phosphorous oxychloride added. The reaction was heated at reflux for approximately 1.5 hours. The reaction was cooled and poured into an ice cold solution of saturated sodium bicarbonate and extracted with ethyl acetate. The organic layer was washed with brine, dried over magnesium sulfate and evaporated to yield 221 mg (92%) of product. 1H NMR (500 MHz, CHLOROFORM-D) δ ppm 8.38 (s, 1 H) 7.86 (d, J=8.55 Hz, 1 H) 7.73 (d, J=8.55 Hz, 1 H) 7.56-7.62 (m, 2 H) 7.42-7.54 (m, 3 H) 6.90 (s, 1 H) 5.93 (d, J=12.51 Hz, 1 H) 4.36 (d, J=11.29 Hz, 1 H) 3.95 (s, 3 H) 3.69 (s, 3 H) 3.03 (t, J=7.48 Hz, 2 H) 1.82-2.92 (m, 1 H) 2.69 (t, J=7.48 Hz, 2 H) 1.68-2.19 (m, 8 H) 1.49-1.61 (m, 1 H) 1.31-1.49 (m, 2 H) 1.14-1.31 (m, 2 H); MS m/z 525(MH$^+$).

EXAMPLE 35

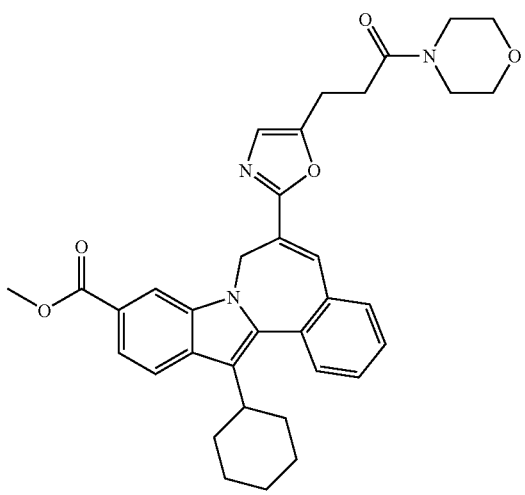

13-cyclohexyl-6-[5-[3-(4-morpholinyl)-3-oxopropyl)]-2-oxazolyl]-7H-indolo[2,1-a][2]benzazepine-10-carboxylic acid, methyl ester. 7H-indolo[2,1-a][2]benzazepine-10-carboxylic acid, 13-cyclohexyl-6-[5-(3-methoxy-3-oxopropyl)-2-oxazolyl]-, methyl ester (281 mg, 0.53 mMol) was dissolved in 3.5 ml of THF and 0.8 ml of 1.0M tetrabutylammonium hydroxide in methanol was added to the reaction. The reaction was stirred at room temperature for 3.5 hours and quenched by partitioning between 0.1N hydrochloric acid and ethyl acetate. The organic phase was washed with brine and dried over magnesium sulfate. Volatiles were removed and the sample dried in vacuuo to yield 232 mg (86%) of a yellow solid which was carried on without further purification. The yellow solid was suspended in 3 ml of dichloromethane and 2 ml of 2.0M oxalyl chloride in dichloromethane added to the reaction followed by 1 drop of DMF. The reaction was stirred at room temperature under nitrogen for 3 hrs 20 min. Volatiles from the reaction were removed in vacuuo and the sample dried in vacuuo at room temperature for 2 hr 45 min then dissolved in 5 ml of dichloromethane and 0.15 ml (1.72 mMol) of morpholine added. The reaction was stirred under a nitrogen atmosphere at room temperature for 2 days. The reaction was partitioned between ethyl acetate and 0.1N hydrochloric acid, washed with brine, dried over magnesium sulfate to yield 282 mg of residue. The reaction product was purified by silica column chromatography using a gradient elution of 5% ethyl acetate/dichloromethane to 30% ethyl acetate/dichloromethane to yield 157 mg (60%) of a yellow amorphous solid. 1H NMR (500 MHz, CHLOROFORM-D) δ ppm 8.38 (s, 1 H) 7.86 (d, J=8.55 Hz, 1 H) 7.73 (d, J=8.55 Hz, 1 H) 7.57-7.63 (m, 2H) 7.45-7.53 (m, 3 H) 6.92 (s, 1 H) 5.92 (d, J=13.43 Hz, 1 H) 4.37 (d, J=14.04 Hz, 1 H) 3.95 (s, 3 H) 3.47-3.76 (m, 6 H) 3.38 (d, J=4.27 Hz, 2 H) 3.07 (t, J=7.48 Hz, 2H) 2.80-2.92(m, 1 H) 2.65 (t, J=7.48 Hz, 2 H) 1.87-2.19(m, 5 H) 1.66-1.86(m, 4 H) 1.50-1.66 (m, 2 H) 1.15-1.50 (m, 5 H); MS m/z 580(MH$^+$).

EXAMPLE 36

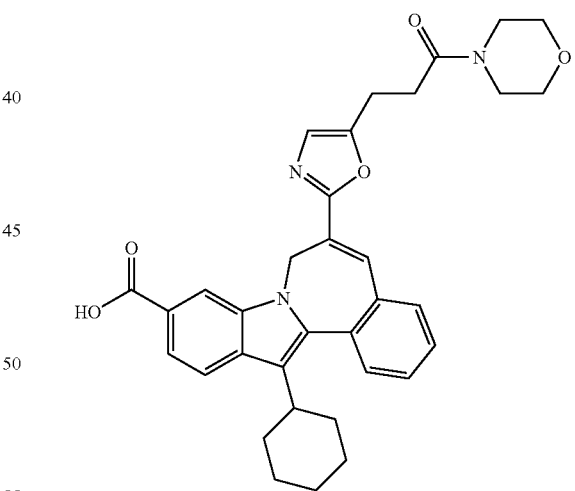

13-cyclohexyl-6-[5-[3-(4-morpholinyl)-3-oxopropyl]-2-oxazolyl]-7H-indolo[2,1-a][2]benzazepine-10-carboxylic acid. 7H-indolo[2,1-a][2]benzazepine-10-carboxylic acid, 13-cyclohexyl-6-[5-[3-(4-morpholinyl)-3-oxopropyl]-2-oxazolyl]-, methyl ester (22.4 mg, 0.039 mMol) and potassium trimethyl silanolate (75 mg, 0.19 mMol) was placed in a 1 dram vial with a magnetic stir bar and 0.4 ml of anhydrous THF added. The reaction was capped under nitrogen and stirred at room temperature for 22 hours. The reaction was acidified by the addition of acetic acid, diluted with acetonitrile and purified by PREP HPLC using the following conditions to yield 12.7 mg (57%) of product: % A=10% acetonitrile, 90% water, 0.1% TFA; % B=90% acetonitrile, 10% water, 0.1% TFA; Initial % B=30; Final % B=100; Gradient=15 min; Runtime=20 min; Flow rate=25 ml/min; Column=Phenomenex Luna 21.2 mm×100 mm s10; 1H NMR (500 MHz, CHLOROFORM-D) δ ppm 8.52 (s, 1 H) 7.90 (d, J=8.55 Hz, 1 H) 7.80 (dd, J=8.55, 1.22 Hz, 1 H) 7.65 (s, 1 H) 7.59-7.64 (m, 1 H) 7.44-7.56 (m, 3 H) 7.01 (s, 1 H) 5.88 (d, J=13.43 Hz, 1 H) 5.46 (s, 4H, $H_2O/H^+$peak) 4.40 (d, J=13.12 Hz, 1 H) 3.51-3.69 (m, 6 H) 3.34-3.45 (m, 2 H) 3.10 (t, J=7.32 Hz, 2 H) 2.82-2.91 (m, 1 H) 2.66-2.73 (m, 2 H) 1.98-2.19 (m, 3 H) 1.87-1.99 (m, 1 H) 1.70-1.85 (m, 2 H) 1.34-1.65 (m, 3 H) 1.15-1.34 (m, 3 H); MS m/z 566($MH^+$).

EXAMPLE 37

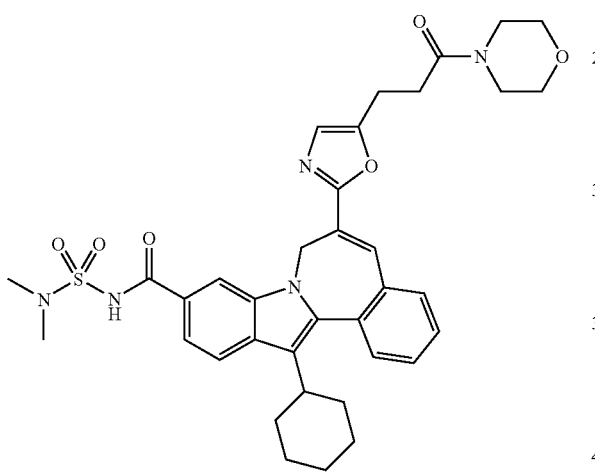

13-cyclohexyl-N-[(dimethylamino)sulfonyl]-6-[5-[3-(4-morpholinyl)-3-oxopropyl]-2-oxazolyl-]7H-indolo[2,1-a][2]benzazepine-10-carboxamide. 7H-indolo[2,1-a][2]benzazepine-10-carboxylic acid, 13-cyclohexyl-6-[5-[3-(4-morpholinyl)-3-oxopropyl]-2-oxazolyl]- (75 mg, 0.13 mMol) was dissolved in 1.5 ml of THF. Carbonyldiimidazole (28 mg, 0.17 mMol) was added to the reaction and the reaction was stirred under nitrogen at room temperature for 40 minutes then heated to reflux for 40 minutes. The reaction was cooled under nitrogen and N,N-dimethylsulfamide (84 mg, 0.68 mMol) added to the reaction followed by DBU (22 uL, 0.15 mMol). The reaction was stirred overnight at room temperature. The reaction was partitioned be 0.1N hydrochloric acid and ethyl acetate. The organic phase was washed with 0.1N hydrochloric acid, brine and dried over magnesium sulfate. Volatiles were removed in vacuuo and the residue was purified by Prep HPLC under the following conditions: Shimadzu prep. HPLC using Discovery VP software; % A=10% acetonitrile, 90% water, 0.1% TFA; % B=90% acetonitrile, 10% water, 0.1% TFA; Initial % B=30; Final % B=100; Gradient=12 min; Runtime=22 min; Flow rate=25 ml/min; Column=Waters Sunfire 19×100 mm S5; Collected 49.6 mg (55%) of product as an orange solid with retention time=10.6 min; 1H NMR (500 MHz, CHLOROFORM-D) δ ppm 1.09-1.32 (m, 1 H) 1.32-1.61 (m, 3 H) 1.68-1.87 (m, 2 H) 1.91-2.18 (m, 4 H) 2.69-2.79 (m, 2 H) 2.82-2.93 (m, 1 H) 3.05 (s, 6 H) 3.07-3.11 (m, 1 H) 3.14 (s, 1 H) 3.44 (d, J=4.58 Hz, 2 H) 3.53-3.75 (m, 6 H) 4.40 (d, J=9.16 Hz, 1 H) 5.76 (d, J=14.04 Hz, 1 H) 6.97 (s, 1 H) 7.49-7.57 (m, 3 H) 7.62 (d, J=7.32 Hz, 1 H) 7.68 (d, J=8.55 Hz, 1 H) 7.71 (s, 1 H) 7.92 (d, J=8.55 Hz, 1 H) 8.49 (s, 1 H) 9.99 (s, 1 H); MS m/z 672($MH^+$); MS m/z 670$(M-H)^-$.

EXAMPLE 38

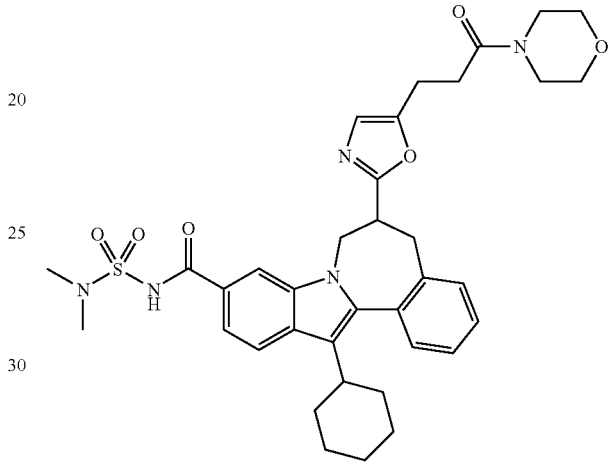

13-cyclohexyl-N-[(dimethylamino)sulfonyl]-6,7-dihydro-6-[5-[3-(4-morpholinyl)-3-oxopropyl]-2-oxazolyl]-5H-indolo[2,1-a][2]benzazepine-10-carboxamide. 7H-indolo[2,1-a][2]benzazepine-10-carboxamide, 13-cyclohexyl-N-[(dimethylamino)sulfonyl]-6-[5-[3-(4-morpholinyl)-3-oxopropyl]-2-oxazolyl]-(18 mg, 0.027 mMol) was dissolved in a mixture 1.0 ml of THF, 0.5 ml of methanol and 10% palladium on carbon (7 mg) was added. The reaction was placed under hydrogen (balloon atmosphere) and stirred at room temperature for 22 hours. The reaction was filtered through a celite plug, and the celite rinsed with methanol and THF. Volatiles from the filtrate were removed in vacuuo and the residue was dissolved in methanol and purified by Prep HPLC under the following conditions: Shimadzu prep. HPLC using Discovery VP software; % A=10% methanol, 90% water, 0.1% TFA; % B=90% methanol, 10% water, 0.1% TFA; Initial % B=35; Final % B=100; Gradient=30 min; Runtime=50 min; Flow rate=20 ml/min; Column=YMC Pro Pack 20 mm×150 mm S5; Product Retention time=29.4 min.; 1H NMR (500 MHz, CHLOROFORM-D) δ ppm 1.19-1.32 (m, 1 H) 1.31-1.53 (m, 2 H) 1.68 (d, J=12.21 Hz, 1 H) 1.78 (d, J=9.46 Hz, 2 H) 1.93 (d, J=11.90 Hz, 1 H) 1.97-2.11 (m, 3 H) 2.55-2.75 (m, 2 H) 2.80-2.89 (m, 1 H) 2.89-3.14 (m, 10 H) 3.16-3.24 (m, 1 H) 3.33-3.61 (m, 3 H) 3.62-3.74 (m, 5 H) 3.84 (dd, 1 H) 4.06 (dd, J=15.11, 5.95 Hz, 1 H) 4.80 (d, J=15.26 Hz, 1 H) 6.89-6.95 (m, 1 H) 7.45 (d, J=5.19 Hz, 4 H) 7.62 (d, J=7.63 Hz, 1 H) 7.90 (d, J=8.54 Hz, 1 H) 8.05 (s, 1 H) 9.68 (s, 1 H); MS m/z 674($MH^+$).

EXAMPLE 39

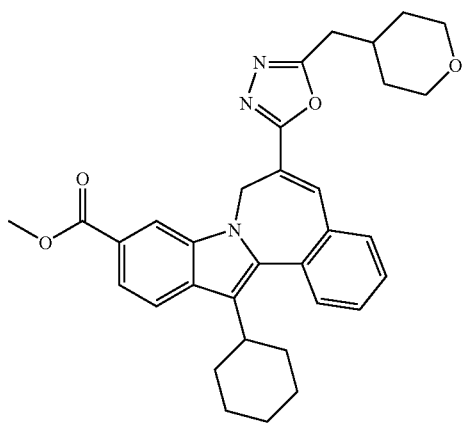

13-cyclohexyl-6-[5-[(tetrahydro-2H-pyran-4-yl)methyl]-1,3,4-oxadiazol-2-yl]-7H-indolo[2,1-a][2]benzazepine-10-carboxylic acid, methyl ester. 7H-indolo[2,1-a][2]benzazepine-6,10-dicarboxylic acid, 13-cyclohexyl-, 10-methyl ester, 6-hydrazide (720 mg, 1.68 mMol) and Ethyl 2-(tetrahydro-2H-pyran-4-yl)acetimidate hydrochloride (422 mg, 2.05 mMol) was suspended in 5.2 mL of isopropanol and diisopropylethyl amine (DIEA) (4.4 ml, 25.3 mMol) added to the reaction. The reaction was stirred for 10 minutes and heated to approximately 70 C under nitrogen for 2 hours before increasing the reaction temperature to 80 C. After 21 hours of heating, HPLC analysis of the reaction showed approximately 27% conversion to cyclized triazole with approximately 72% as uncyclized intermediate. The reaction was transferred to a 20 mL microwave vessel and an additional 5 mL of isopropanol added to the reaction. The reaction was heated in a microwave to 150 C for 1 hour. Reaction volatiles were removed in vacuuo and the residue shaken in a separatory funnel with ethyl acetate and 1 N hydrochloric acid. The reaction residue failed to adequately dissolve in the organic phase, therefore most of the aqueous phase was drained off and dichloromethane added. The pH of the organic phase was raised by washing with saturated sodium bicarbonate. This step appeared to aid in solids dissolution. The organic phases were washed with brine and dried over magnesium sulfate to yield 905 mg of a yellow-orange solid. The oxadiazole product ($R_f$=0.55 in 25% ethyl acetate in dichloromethane) was isolated using silica gel column chromatography eluting with a gradient of 10% ethyl acetate in dichloromethane to 30% ethyl acetate in dichloromethane. Weight of product=182 mg as a yellow solid. An analytically pure sample (164.6 mg) was obtained by trituration with hot methanol (2 ml) and rinsing with 2 ml of methanol at room temperature. 1H NMR (500 MHz, CHLOROFORM-D) δ ppm 7.88 (d, J=8.24 Hz, 1 H) 7.63 (t, J=3.36 Hz, 2 H) 7.46-7.58 (m, 3 H) 5.94 (d, J=7.32 Hz, 1 H) 4.46 (d, J=11.29 Hz, 1 H) 3.86-4.01 (m, 5 H) 3.38 (t, J=11.60 Hz, 2 H) 2.75-2.95 (m, 3 H) 2.00-2.23 (m, 4 H) 1.88-2.00 (m, 1H) 1.66-1.85 (m, 5 H) 1.51-1.66 (m, 2 H) 1.33-1.50 (m, 4 H) 1.13-1.31 (m, 1 H); MS m/z 538(MH⁺).

EXAMPLE 40

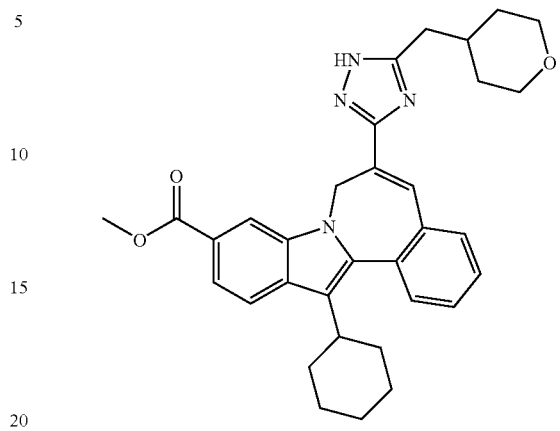

13-cyclohexyl-6-[5-[(tetrahydro-2H-pyran-4-yl)methyl]-1H-1,2,4-triazol-3-yl]-7H-indolo[2,1-a][2]benzazepine-10-carboxylic acid, methyl ester. From the reaction mixture describing the preparation of 7H-indolo[2,1-a][2]benzazepine-10-carboxylic acid, 13-cyclohexyl-6-[5-[(tetrahydro-2H-pyran-4-yl)methyl]-1,3,4-oxadiazol-2-yl]-, methyl ester, the titled compound was isolated ($R_f$=0.17 in 25% ethyl acetate in dichloromethane) from the above silica gel column chromatography to yield 476 mg (53%) as a yellow solid. 1H NMR (500 MHz, CHLOROFORM-D) δ ppm 8.38 (s, 1 H) 7.75-7.90 (m, 2 H) 7.68 (d, J=8.24 Hz, 1 H) 7.56-7.63 (m, 1 H) 7.50-7.56 (m, 1 H) 7.41-7.50 (m, 2 H) 5.91 (d, J=12.21 Hz, 1 H) 4.26 (d, J=11.90 Hz, 1 H) 3.87-4.02 (m, 5 H) 3.33 (t, J=11.29 Hz, 2 H) 2.87 (s, 1 H) 2.76 (s, 2 H) 1.84-2.17(m, 6 H) 1.68-1.82(m, 2 H) 1.30-1.66(m, 8 H) 1.13-1.29(m, 2 H); MS m/z 537(MH⁺).

EXAMPLE 41

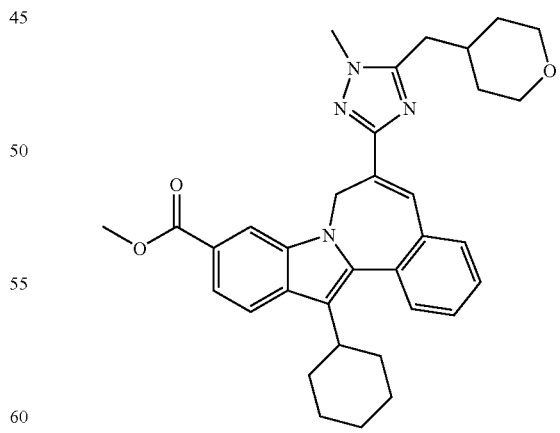

13-cyclohexyl-6-[1-methyl-5-[(tetrahydro-2H-pyran-4-yl)methyl]-1H-1,2,4-triazol-3-yl]-7H-indolo[2,1-a][2]benzazepine-10-carboxylic acid, methyl ester. 7H-indolo[2,1-a][2]benzazepine-10-carboxylic acid, 13-cyclohexyl-6-[5-[(tetrahydro-2H-pyran-4-yl)methyl]-1H-1,2,4-triazol-3-yl]-, methyl ester (167 mg, 0.31 mMol) was dissolved in 3 ml of DMF. Iodomethane (39 uL, 0.62 mMol) was added to the reaction followed by sodium hydride (60% in mineral oil, 0.47 mMol). The reaction was capped under nitrogen and stirred at room temperature for 16 hrs. Volatiles were removed in vacuuo and the reaction partitioned between ethyl acetate and saturated aqueous ammonium chloride. Extract aqueous with ethyl acetate. Combine organic fractions and wash with saturated ammonium chloride, brine, dry over magnesium sulfate to obtain 174 mg of a yellow-brown solid. Chromatograph residue on silica gel using 10% ethyl acetate in dichloromethane to obtain 100 mg (58%) of product.

1H NMR (500 MHz, CHLOROFORM-D) δ ppm 8.47 (s, 1 H) 7.85 (d, J=8.55 Hz, 1 H) 7.67-7.76 (m, 2 H) 7.60 (dd, J=5.19, 3.66 Hz, 1 H) 7.49-7.56 (m, 1 H) 7.41-7.49 (m, 2 H) 5.97 (d, J=13.12 Hz, 1 H) 4.35 (d, J=14.04 Hz, 1 H) 3.90-3.98 (m, 5 H) 3.87 (s, 3 H) 3.37 (t, J=11.44 Hz, 2 H) 2.84-2.93 (m, 1 H) 2.68 (d, J=7.02 Hz, 4H) 2.68 (d, J=7.02 Hz, 2 H) 1.89-2.18 (m, 6 H) 1.67-1.83 (m, 2 H) 1.64 (d, J=12.82 Hz, 2 H) 1.49-1.61 (m, 3 H) 1.32-1.48 (m, 5 H) 1.14-1.31 (m, 3 H)

EXAMPLE 42

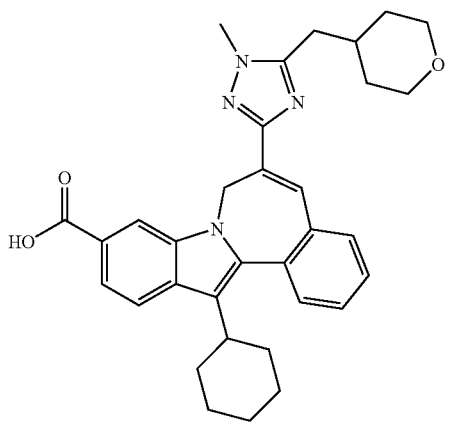

13-cyclohexyl-6-[1-methyl-5-[(tetrahydro-2H-pyran-4-yl)methyl]-1H-1,2,4-triazol-3-yl]-7H-indolo[2,1-a][2]benzazepine-10-carboxylic acid. 7H-indolo[2,1-a][2]benzazepine-10-carboxylic acid, 13-cyclohexyl-6-[1-methyl-5-[(tetrahydro-2H-pyran-4-yl)methyl]-1H-1,2,4-triazol-3-yl]-, methyl ester (94 mg, 0.17 mMol) was dissolved in 1.7 ml of anhydrous THF and potassium trimethylsilanolate (104 mg, 0.81 mMol) added to the reaction. The reaction was capped under nitrogen and stirred at room temperature for 22 hrs. The reaction was quenched with 1 N hydrochloric acid and the product extracted into ethyl acetate, washed with brine and dried over magnesium sulfate. Volatiles were removed in vacuuo to yield 89 mg of crude product. The product was purified by trituration with diethyl ether to yield 59 mg (64%). 1H NMR (500 MHz, CHLOROFORM-D) δ ppm 8.55 (s, 1 H) 7.89 (d, J=8.55 Hz, 1 H) 7.78 (d, J=8.55 Hz, 2 H) 7.61 (dd, J=5.34, 3.51 Hz, 1 H) 7.51-7.58 (m, 1 H) 7.46 (dd, J=5.49, 3.36 Hz, 2 H) 5.97 (d, J=14.04 Hz, 1 H) 4.36 (d, J=13.43 Hz, 1 H) 3.94 (dd, J=11.44, 3.51 Hz, 2 H) 3.88 (s, 3 H) 3.38 (t, J=11.29 Hz, 2 H) 2.83-2.96 (m, 1 H) 2.71 (d, J=6.41 Hz, 2 H) 1.88-2.25 (m, 6 H) 1.76 (d, J=11.60 Hz, 2 H) 1.65(d, J=11.90 Hz, 2 H) 1.30-1.59(m, 6 H) 1.16-1.27(m, 2 H); MS m/z 537(MH+).

EXAMPLE 43

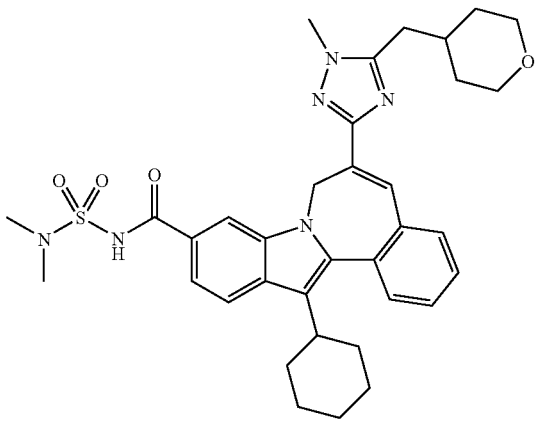

13-cyclohexyl-N-[(dimethylamino)sulfonyl]-6-[1-methyl-5-[(tetrahydro-2H-pyran-4-yl)methyl]-1H-1,2,4-triazol-3-yl]-7H-indolo[2,1-a][2]benzazepine-10-carboxamide. 7H-indolo[2,1-a][2]benzazepine-10-carboxylic acid, 13-cyclohexyl-6-[1-methyl-5-[(tetrahydro-2H-pyran-4-yl)methyl]-1H-1,2,4-triazol-3-yl]- (58 mg, 0.11 mMol) was dissolved in 2 ml of dichloromethane containing 2.0 M of oxalyl chloride. One drop of DMF was added to the reaction mixture and the reaction was stirred for 2.5 hrs under nitrogen. The volatiles were removed in vacuuo and the acid chloride stored under nitrogen until needed. N,N-dimethylsulfamide (45.7 mg, 0.37 mMol) was dissolved in 0.5 ml of THF and 2-tert-butylimino-2-diethylamino-1,3-dimethylperhydro-1,3,2-diazaphosphorine (68.8 uL, 0.238 mMol) added. The reaction was stirred at room temperature for approximately 15 minutes then the above acid chloride dissolved in 1 ml of THF was added dropwise via syringe. The reaction was capped under nitrogen and stirred for 2 hours at room temperature after which the reaction progress was monitored by HPLC. Additional N,N-dimethylsulfamide (20 mg, 0.16 mMol) and 2-tert-butylimino-2-diethylamino-1,3-dimethylperhydro-1,3,2-diazaphosphorine (46 ul, Mmol) in 0.3 mL of THF was added to the reaction. The reaction was stirred for an additional 15.5 hrs under nitrogen. The reaction was partitioned between ethyl acetate and 0.1 M citric acid, washed with 0.1M citric acid. The organic phase was washed with brine, dried over magnesium sulfate and the volatiles removed in vacuuo to yield 125 mg of a brown oil. The product (4.3 mg, 6%) was isolated by Prep HPLC under the following conditions: Shimadzu prep. HPLC using Discovery VP software; % A=10% methanol, 90% water, 0.1% TFA; % B=90% methanol, 10% water, 0.1% TFA; Initial % B=35; Final % B=100; Gradient=30 min; Runtime=50 min; Flow rate=20 ml/min; Wavelength=220 nm; Column=YMC Pro Pack 20 mm×150 mm S5. 1H NMR (500 MHz, CHLOROFORM-D) δ ppm 8.73 (s, 1 H) 8.27 (s, 1 H) 7.91 (d, J=8.55 Hz, 1 H) 7.77-7.88 (m, 2 H) 7.58-7.65 (m, 1 H) 7.44-7.57 (m, 5 H) 5.81 (d, J=14.34 Hz, 1 H) 4.41 (d, J=13.12 Hz, 1 H) 3.91-4.04 (m, 7 H) 3.32-3.44 (m, 2 H) 3.13-3.23 (m, 1 H) 3.07 (s, 6 H) 2.81-2.95 (m, 4 H) 1.85-2.16 (m, 7 H) 1.67-1.83 (m, 3 H) 1.50-1.65 (m, 4 H) 1.15-1.51 (m, 8 H); MS m/z 643(MH+).

EXAMPLE 44

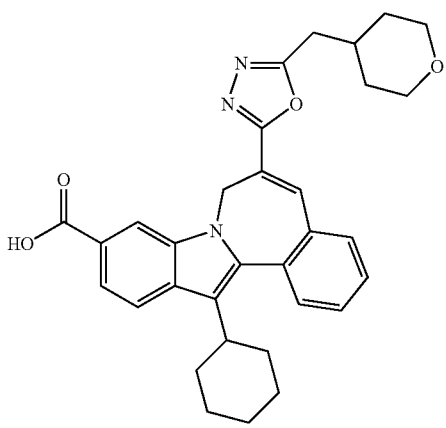

13-cyclohexyl-6-[5-[(tetrahydro-2H-pyran-4-yl)methyl]-1,3,4-oxadiazol-2-yl]-7H-indolo[2,1-a][2]benzazepine-10-carboxylic acid. 7H-indolo[2,1-a][2]benzazepine-10-carboxylic acid, 13-cyclohexyl-6-[5-[(tetrahydro-2H-pyran-4-yl)methyl]-1,3,4-oxadiazol-2-yl]-, methyl ester (156 mg, 0.29 mMol) was dissolved in anhydrous THF and potassium trimethylsilanolate (198 mg, 1.54 mMol) was added to the reaction. The reaction was capped under nitrogen and stirred at room temperature for 19 hours. The reaction was partitioned between ethyl acetate and 0.1N hydrochloric acid. The reaction was extracted with ethyl acetate and the organic phases combined and washed with brine, dried over magnesium sulfate and volatiles removed in vacuuo to yield 166 mg of crude material. Approximate 87 mg of the crude reaction was dissolved in a mixture of methanol/acetonitrile/DMF and subjected to HPLC purification using the following conditions: % A=10% acetonitrile, 90% water, 0.1% TFA; % B=90% acetonitrile, 10% water, 0.1% TFA; Initial % B=30; Final % B=100; Gradient=10 min; Runtime=15 min; Flow rate=25 ml/min; Column=Phenomenex Luna 21.2 mm×100 mm s 10; Retention Time of 7H-indolo[2,1-a][2]benzazepine-10-carboxylic acid, 13-cyclohexyl-6-[5-[(tetrahydro-2H-pyran-4-yl)methyl]-1,3,4-oxadiazol-2-yl]- was 9.9 minutes. 1H NMR (500 MHz, CHLOROFORM-D) δ ppm 8.48 (s, 1 H) 7.91 (d, J=8.55 Hz, 1 H) 7.80 (dd, J=8.55, 1.53 Hz, 1 H) 7.61-7.68 (m, 2 H) 7.49-7.58 (m, 3 H) 5.96 (d, J=13.12 Hz, 1 H) 4.48 (d, J=8.24 Hz, 1 H) 3.96 (dd, J=11.44, 3.20 Hz, 2 H) 3.33-3.44 (m, 3 H) 2.81-2.92 (m, 3 H) 2.01-2.20 (m, 4 H) 1.90-2.01 (m, 1 H) 1.65-1.84 (m, 4 H) 1.51-1.62 (m, 1 H) 1.32-1.52 (m, 5 H) 1.16-1.29 (m, 1 H); MS m/z 524(MH$^+$); MS m/z 522 (M-H)$^-$.

EXAMPLE 45

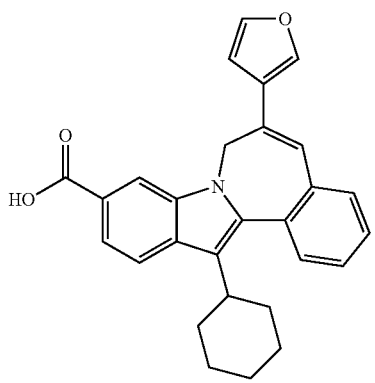

13-Cyclohexyl-6-(furan-3-yl)-7H-indolo{2,1-a][2]benzazepine-10-carboxylic Acid. Step 1: Sodium hydride (44 mg of 95%, 1.74 mmol) was added to an ice cold solution of methyl 3-cyclohexyl-2-(2-vinylphenyl) 1H-indole-6-carboxylate (0.500 mg, 1.34 mmol) in THF (6 mL). When the evolution of hydrogen subsided, 2,3-dibromoprop-1-ene (402 mg, 2.01 mmol) was added in a single portion. Stirring was continued at 0° C. for 2 hr and then at 22° C. for 24 hr. The solution was concentrated and the residue chromatographed on SiO2 with petroleum ether-ethyl acetate (10:1 H using the flash technique to afford methyl 1-(2-bromoallyl)-3-cyclohexyl-2-(2-vinylphenyl)-1H-indole-6-carboxylate (285 mg, 44.5%) as a gummy solid. MS m/z 479 (MH$^+$). Step 2: Tetrakis(triphenylphosphine)palladium(0 H (38 mg, 0.033 mmol) was added to a stirred and degassed mixture of methyl 1-(2-bromoallyl)-3-cyclohexyl-2-(2-vinylphenyl)-1H-indole-6-carboxylate (157 mg, 0.33 mmol), 3-furylboronic acid (54.5 mg, 0.49 mmol), LiCl (55 mg, 0.66 mmol) in ethanol (2 mL) and toluene (2 mL) containing 1M aqueous sodium carbonate (0.82 mL, 0.82 mmol). The mixture was heated under reflux for 1 hr, cooled and partitioned between ethyl acetate and water. The organic layer was washed (water, brine), dried over sopdium sulfate and concentrated. The crude product was purified on a silicic acid thick layer plate. The plate was eluted with hexanes-ethyl acetate (10:1 H to provide methyl 3-cyclohexyl-1-(furan-3-yl)-2-(2-vinylphenyl)-1H-indole-6-carboxylate as a gum (57 mg, 37%). MS m/z 466 (MH$^+$); 1H NMR (500 MHz, CHLOROFORM-D) δ ppm 1.15-1.89 (m, 10 H) 2.42-2.53 (m, 1 H) 3.91 (s, 3 H) 4.25 (s, 1 H) 4.48 (d, J=17.40 Hz, 1 H) 4.82 (d, J=17.40 Hz, 1 H) 4.82 (d, J=17.40 Hz, 1 H). 5.09-5.17 (m, 2 H) 5.69 (d, J=17.70 Hz, 1 H) 6.34-6.47 (m, 2 H) 7.18-7.23 (m, 2 H) 7.28 (t, J=7.93 Hz, 1 H) 7.32 (t, J=1.68 Hz, 1 H) 7.42 (t, J=7.63 Hz, 1 H) 7.69 (d, J=7.63 Hz, 1 H) 7.79-7.85 (m, 2 H) 8.00 (s, 1 H). Step 3: Grubb's second generation catalyst (10 mg) was added to a solution of methyl 3-cyclohexyl-1-(furan-3-yl)-2-(2-vinylphenyl)-1H-indole-6-carboxylate (47 mg) in methylene chloride (8 mL). The solution was stirred under reflux for 18 hr and concentrated to dryness The residue was purified on a silicic acid preparative plate. The plate was eluted with hexanes-ethyl acetate (10:1 H. The product containing band was extracted and the extract was concentrated. Purification on a second thick layer plate afforded 13-cyclohexyl-6-(furan-3-yl)-7H-indolo{2,1-a][2]benzazepine-10-carboxylate as a golden solid (17 mg, 39%). MS m/z 438 (MH$^+$); 1H NMR (300 MHz, CHLOROFORM-D) δ ppm 1.11-2.16 (m, 10H) 2.78-2.95 (m, 1 H) 3.94 (s, 3 H) 4.34-4.49 (m, 1 H) 5.00-5.15 (m, 1 H) 6.60 (s, 1 H) 6.93 (s, 1 H) 7.38-7.45 (m, 4 H) 7.55 (d, J=8.42 Hz, 1 H) 7.70 (dd, J=8.42, 1.46 Hz, 1 H) 7.81-7.88 (m, 2 H) 8.17 (s, 1 H). Step 4: A mixture of the preceding ester (17 mg) in THF (250 µL), methanol (250 µL), and 1.0 N NaOH (200 µL) was heated at 100° C. on a microwave apparatus for 15 min. The resulting solution was cooled and acidified with dilute HCl to precipitate the titled acid as a golden solid. MS m/z 424 (MH$^+$).

EXAMPLE 46

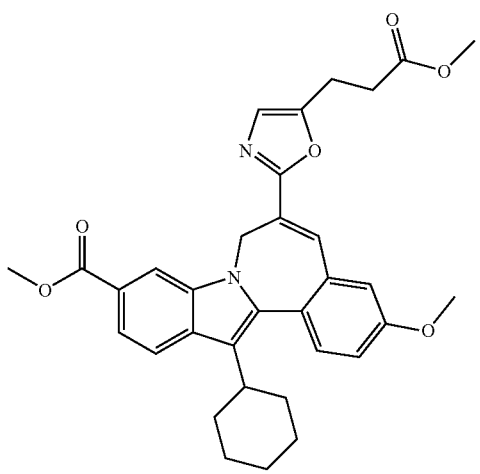

Methyl 13-cyclohexyl-3-methoxy-6-(5-(3-methoxy-3-oxopropyl)-1,3-oxazol-2-yl)-7H-indolo[2,1-a][2]benzazepine-10-carboxylate. Methyl 13-cyclohexyl-3-(methyloxy)-6-(((5-(methyloxy)-2,5-dioxopentyl)amino)carbonyl)-7H-indolo[2,1-a][2]benzazepine-10-carboxylate (1.60 g, 2.79 mMol) was suspended in 38 ml of toluene along with phosphorus oxychloride (0.58 mL, 6.34 mMol). The mixture was heated to reflux under nitrogen for 3 hrs, cooled and poured into a sepratory funnel containing ice and saturated aqueous sodium bicarbonate solution. The aqueous mixture was extracted with ethyl acetate. The organic layer was washed sequentially with aqueous saturated bicarbonate, brine and dried over magnesium sulfate. Removal of volatiles and drying in vacuuo produced the title product in quantitative yield (1.55 g). 1H NMR (500 MHz, CHLOROFORM-d) δ ppm 1.27 (1 H, br. s.), 1.36-1.45 (2 H, m), 1.59 (2 H, br. s.), 1.78 (2 H, d, J=9.77 Hz), 1.96 (1 H, br. s.), 2.06 (2 H, br. s.), 2.71 (2 H, t, J=7.48 Hz), 2.81-2.90 (1 H, m), 3.04 (2 H, t, J=7.32 Hz), 3.70 (3 H, s), 3.95 (3 H, s), 3.98 (3 H, s), 4.37 (1 H, d, J=11.60 Hz), 5.93 (1 H, d, J=12.51 Hz), 6.91 (1 H, s), 7.02 (1 H, d, J=2.75 Hz), 7.07 (1 H, dd, J=8.70, 2.59 Hz), 7.53 (2 H, s), 7.74 (1 H, d, J=8.55 Hz), 7.85 (1 H, d, J=8.55 Hz), 8.38 (1 H, s). HPLC analysis: Shimadzu Analytical HPLC using Discovery VP software: % A=10% methanol, 90% water, 0.1% trifluoroacetic acid; % B=90% methanol, 10% water, 0.1% trifluoroacetic acid; Initial % B=50; Final % B=100; Gradient=5 min; Runtime=6 min; Flow rate=5 ml/min; Wavelength=220 nm; Column=Phenomenex Luna 3.0 mm×50 mm S10; Retention Time=4.48 min, purity 96%. Flow injection Mass Spectrometry: MS m/z 555(MH$^+$).

EXAMPLE 47

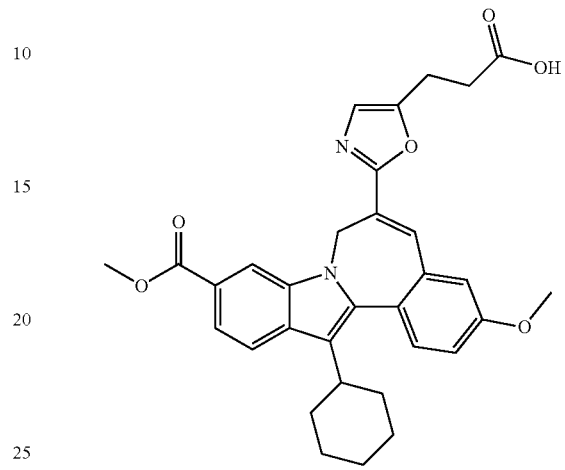

3-(2-(13-Cyclohexyl-3-methoxy-10-(methoxycarbonyl)-7H-indolo[2,1-a][2]benzazepin-6-yl)-1,3-oxazol-5-yl)propanoic acid. Methyl 13-cyclohexyl-3-methoxy-6-(5-(3-methoxy-3-oxopropyl)-1,3-oxazol-2-yl)-7H-indolo[2,1-a][2]benzazepine-10-carboxylate (1.53 g, 2.92 mMol) was dissolved in 20 mL of THF and 5.8 mL of 1.0M solution of tetrabutylammonium hydroxide in methanol was added. The reaction was stirred under nitrogen atmosphere for 2 hrs to completion. The reaction was partitioned between ethyl acetate and 1N aqueous hydrochloric acid. The ethyl acetate layer was washed with 1N hydrochloric acid then the aqueous layers combined and back extracted with ethyl acetate. The organic layers were combined, and washed sequentially with 1N hydrochloric acid, brine and dried over magnesium sulfate. Volatiles were removed in vacuuo to yield a amorphous yellow solid/foam (1.54 g). 1H NMR (500 MHz, CHLOROFORM-d) δ ppm 1.21-1.31 (2 H, m), 1.32-1.50 (2 H, m), 1.56 (1 H, br. s.), 1.72-1.82 (2 H, m), 2.01 (1 H, br. s.), 2.03-2.13 (3 H, m), 2.76 (2 H, d, J=6.41 Hz), 2.80-2.89 (1 H, m), 3.13 (2 H, t, J=6.26 Hz), 3.92 (3 H, s), 4.00 (3 H, s), 4.40 (1 H, d, J=12.82 Hz), 5.81 (1 H, d, J=16.17 Hz), 6.92 (1 H, s), 7.01-7.09 (1 H, m), 7.03 (1 H, d), 7.07 (1 H, dd), 7.53 (1 H, d, J=8.55 Hz), 7.73 (2 H, s), 7.86 (1 H, d, J=8.55 Hz), 8.40 (1 H, s). HPLC analysis: Shimadzu Analytical HPLC using Discovery VP software: % A=10% methanol, 90% water, 0.1% trifluoroacetic acid; % B=90% methanol, 10% water, 0.1% trifluoroacetic acid; Initial % B=50; Final % B=100; Gradient=5 min; Runtime=6 min; Flow rate=5 ml/min; Wavelength=220 nm; Column=Phenomenex Luna 3.0 mm×50 mm S10. Retention Time=4.11 min, purity 97%. Flow injection Mass Spectrometry: MS m/z 541(MH$^+$), m/z 539(MH$^-$).

EXAMPLE 48

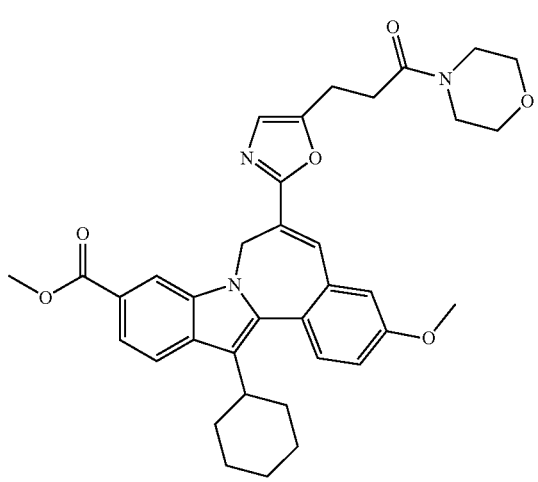

Methyl 13-cyclohexyl-3-methoxy-6-(5-(3-(4-morpholinyl)-3-oxopropyl)-1,3-oxazol-2-yl)-7H-indolo[2,1-a][2]benzazepine-10-carboxylate. 3-(2-(13-Cyclohexyl-3-methoxy-10-(methoxycarbonyl)-7H-indolo[2,1-a][2]benzazepin-6-yl)-1,3-oxazol-5-yl)propanoic acid (1.522 g, 2.82 mMol) was dissolved in 28 mL of THF and carbonyldiimidazole (548 mg, 3.38 mMol) added to the reaction. The reaction was stirred for 1 hr at room temperature under nitrogen then heated to reflux under nitrogen for 1 hr. The reaction was cooled and morpholine (0.3 mL, 3.44 mMol) added, the reaction was stirred under nitrogen for 2 hrs. Volatiles from the reaction were removed in vacuuo and the residue partitioned between ethyl acetate and 1N aqueous hydrochloric acid. The aqueous was extracted with ethyl acetate and the organic layers combined and washed sequentially with 1N hydrochloric acid and brine, dried over magnesium sulfate to yield 1.62 g of crude product. The title compound was purified by silica gel chromatography eluting with a gradient of 50% ethyl acetate in dichloromethane to 65% ethyl acetate in dichloromethane to yield 1.28 g (74%) of product as a amorphous yellow solid. 1H NMR (500 MHz, CHLOROFORM-d) δ ppm 1.27 (2 H, t, J=7.17 Hz), 1.40 (1 H, t, J=7.63 Hz), 1.53-1.62 (2 H, m), 1.78 (2 H, d, J=10.99 Hz), 1.95 (1 H, br. s.), 2.05 (2 H, br. s.), 2.66 (2 H, t, J=7.48 Hz), 2.86 (1 H, td, J=11.83, 3.51 Hz), 3.09 (2 H, t, J=7.48 Hz), 3.36-3.44 (2 H, m), 3.56 (2 H, d, J=4.27 Hz), 3.62 (2 H, br. s.), 3.64 (2 H, d, J=2.75 Hz), 3.93 (3 H, s), 3.96 (3 H, s), 4.38 (1 H, d, J=12.21 Hz), 5.92 (1 H, d, J=14.65 Hz), 6.92 (1 H, s), 7.02 (1 H, d, J=2.75 Hz), 7.07 (1 H, dd, J=8.85, 2.75 Hz), 7.55 (2 H, t, J=4.27 Hz), 7.73 (1 H, d, J=8.55 Hz), 7.85 (1 H, d, J=8.24 Hz), 8.38 (1H, s). LC-MS: Shimadzu Analytical HPLC using Discovery VP software: % A=10% methanol, 90% water, 0.1% trifluoroacetic acid; % B=90% methanol, 10% water, 0.1% trifluoroacetic acid; Initial % B=0; Final % B=100; Gradient=2 min; Runtime=4 min; Flow rate=5 ml/min; Wavelength=220 nm; Column=Phenomenex Luna 3.0 mm×50 mm S10. Retention Time=2.93 min, MS m/z 610(MH+).

EXAMPLE 49

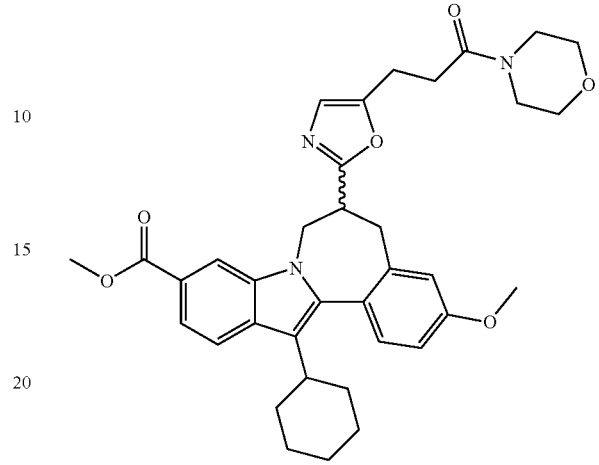

Methyl 13-cyclohexyl-3-methoxy-6-(5-(3-(4-morpholinyl)-3-oxopropyl)-1,3-oxazol-2-yl)-6,7-dihydro-5H-indolo[2,1-a][2]benzazepine-10-carboxylate. Methyl 13-cyclohexyl-3-methoxy-6-(5-(3-(4-morpholinyl)-3-oxopropyl)-1,3-oxazol-2-yl)-7H-indolo[2,1-a][2]benzazepine-10-carboxylate (610 mg, 1.00 mMol)) was dissolved in 15 ml of THF and 5 ml of methanol. To this reaction was added 83 mg of 10% palladium on carbon. The reaction was placed under hydrogen atmosphere (1 atm, balloon pressure) and stirred at room temperature for 22 hrs. The reaction was filtered through a celite plug and rinsed with THF. Volatiles were removed from the filtrate in vacuuo to yield 569 mg (93%) of the title compound as a yellow solid. LC-MS: Shimadzu Analytical HPLC using Discovery VP software: % A=10% methanol, 90% water, 0.1% trifluoroacetic acid; % B=90% methanol, 10% water, 0.1% trifluoroacetic acid; Initial % B=50; Final % B=100; Gradient=3 min; Runtime=4 min; Flow rate=5 ml/min; Wavelength=220 nm; Column=Phenomenex Luna 3.0 mm×50 mm S10. Retention Time=2.55 min, MS m/z 612(MH+).

EXAMPLE 50

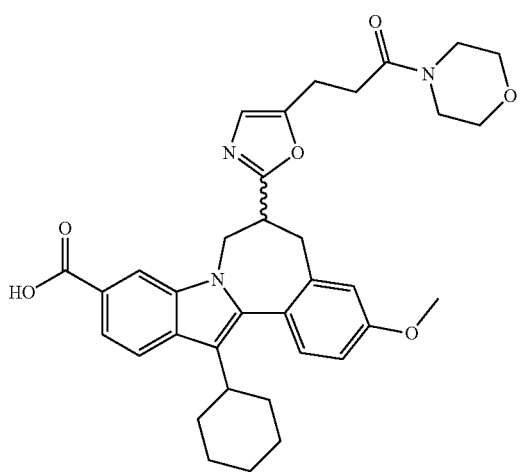

13-Cyclohexyl-3-methoxy-6-(5-(3-(4-morpholinyl)-3-oxopropyl)-1,3-oxazol-2-yl)-6,7-dihydro-5H-indolo[2,1-a][2]benzazepine-10-carboxylic acid. Methyl 13-cyclohexyl-3-methoxy-6-(5-(3-(4-morpholinyl)-3-oxopropyl)-1,3-oxazol-2-yl)-6,7-dihydro-5H-indolo[2,1-a][2]benzazepine-10-carboxylate (560 mg, 0.92 mMol) was dissolved in THF and potassium trimethylsilanolate (585 mg, 4.56 mMol) added. The reaction was stirred under nitrogen atmosphere at room temperature for 20 hrs. 1N aqueous hydrochloric acid was added to the reaction. The reaction was extracted with ethyl acetate. The organic phase washed with brine, dried over magnesium sulfate and volatiles removed in vacuuo to yield 585 mg of a yellow amorphous foam. LC-MS: Shimadzu Analytical HPLC using Discovery VP software: % A=10% methanol, 90% water, 0.1% trifluoroacetic acid; % B=90% methanol, 10% water, 0.1% trifluoroacetic acid; Initial % B=50; Final % B=100; Gradient=5 min; Runtime=6 min; Flow rate=5 ml/min; Wavelength=220 nm; Column=Phenomenex Luna 3.0 mm×50 mm S10. Retention Time=4.05 min, MS m/z 598(MH$^+$), 1195 (2M+H)$^+$.

Chiral Resolution of 13-cyclohexyl-3-methoxy-6-(5-(3-(4-morpholinyl)-3-oxopropyl)-1,3-oxazol-2-yl)-6,7-dihydro-5H-indolo[2,1-a][2]benzazepine-10-carboxylic acid. Conditions: Chiralpak AD-H analytical column, 4.6 mm×250 mm, 5 um; Mobile phase: 35% (0.1% TFA) methanol in carbon dioxide; Temperature=35° C.; Flow rate=2.0 ml/min for 16 min.; UV monitored @ 213 nm; Injection: 5 uL of approximately 1 mg/mL solution in ethanol. Retention time of Isomer A: 5.96 min; Retention time of Isomer B: 11.65 min. Prep. Chiral separation: ChiralPak AD-H, 30 mm×250 mm, 5 um; Mobile phase: 65% carbon dioxide, 35% methanol with 0.1% trifluoroacetic acid; Temperature: 35° C.; Pressure: 150 bar; Flow rate: 70 ml/min; UV: 213 nm; Peak 1 Isomer A: 7.20 min to 9.20 min; Peak 2 Isomer B: 12.4 min to 16.6 min. From 498 mg of racemate, 216 mg of Isomer A and 231 mg of Isomer B were obtained.

EXAMPLE 51

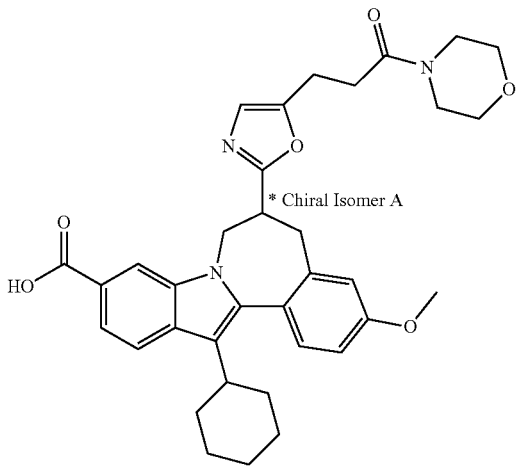

13-Cyclohexyl-3-methoxy-6-(5-(3-(4-morpholinyl)-3-oxopropyl)-1,3-oxazol-2-yl)-6,7-dihydro-5H-indolo[2,1-a][2]benzazepine-10-carboxylic acid. (Peak1-Chiral Isomer A). 1H NMR (500 MHz, CHLOROFORM-D) δ ppm 1.20-1.52 (m, 3.3 H) 1.68 (t, J=12.97 Hz, 1.1 H) 1.79 (d, J=8.55 Hz, 2 H) 1.88-2.12 (m, 4 H) 2.46 (t, J=7.32 Hz, 1.4 H) 2.71 (t, J=7.63 Hz, 0.5 H) 2.79-2.88 (m, 1 H) 2.88-3.11 (m, 3.5 H) 3.15 (dd, J=12.97, 5.95 Hz, 0.8 H) 3.19-3.31 (m, 1.4 H) 3.45-3.75 (m, 6.3 H) 3.84 (s, 0.7 H) 3.87-3.95 (m, 3 H) 3.94-4.03 (m, 0.5 H) 4.07 (dd, J=15.11, 5.34 Hz, 0.8 H) 4.81 (d, J=14.95 Hz, 0.9 H) 6.82-6.97 (m, 1.4 H) 6.97-7.04 (m, 1.5 H) 7.38 (t, J=7.63 Hz, 1 H) 7.72-7.84 (m, 1 H) 7.85-7.93 (m, 1 H) 7.98-8.08 (m, 0.7 H) 8.22 (s, 0.2 H). HPLC analysis: Shimadzu Analytical HPLC using Discovery VP software: % A=10% methanol, 90% water, 0.1% trifluoroacetic acid; % B=90% methanol, 10% water, 0.1% trifluoroacetic acid; Initial % B=50; Final % B=100; Gradient=5 min; Runtime=6 min; Flow rate=5 ml/min; Wavelength=220 nm; Column=Phenomenex Luna 3.0 mm×50 mm S10; Retention Time=3.16 min, purity 98%. Flow injection Mass Spectrometry: MS m/z 598(MH$^+$), m/z 596(MH$^-$.

EXAMPLE 52

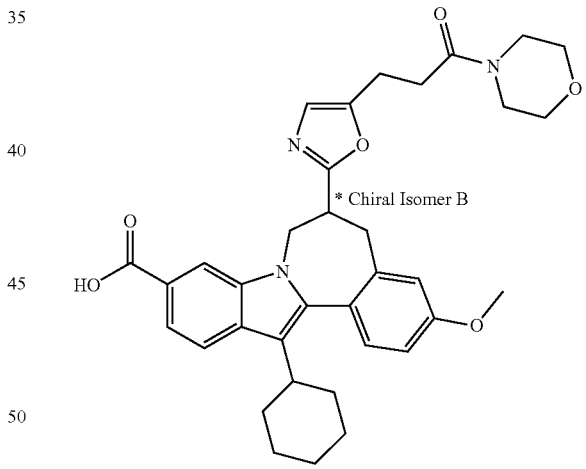

13-Cyclohexyl-3-methoxy-6-(5-(3-(4-morpholinyl)-3-oxopropyl)-1,3-oxazol-2-yl)-6,7-dihydro-5H-indolo[2,1-a][2]benzazepine-10-carboxylic acid (Peak2-Chiral Isomer B). HPLC analysis: Shimadzu Analytical HPLC using Discovery VP software: % A=10% methanol, 90% water, 0.1% trifluoroacetic acid; % B=90% methanol, 10% water, 0.1% trifluoroacetic acid; Initial % B=50; Final % B=100; Gradient=5 min; Runtime=6 min; Flow rate=5 ml/min; Wavelength=220 nm; Column=Phenomenex Luna 3.0 mm×50 mm S10. Retention Time=3.18 min, purity 99%. Flow injection Mass Spectrometry: MS m/z 598(MH$^+$), m/z 596(MH$^-$).

EXAMPLE 53

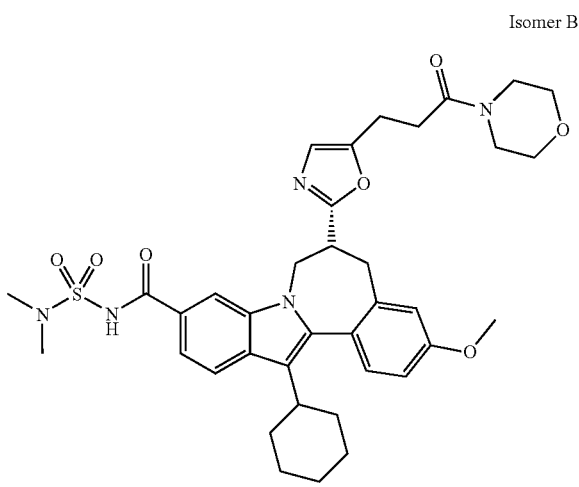

Isomer B

13-Cyclohexyl-N-((dimethylamino)sulfonyl)-3-methoxy-6-(5-(3-(4-morpholinyl)-3-oxopropyl)-1,3-oxazol-2-yl)-6,7-dihydro-5H-indolo[2,1-a][2]benzazepine-10-carboxamide (Isomer B). 13-Cyclohexyl-3-methoxy-6-(5-(3-(4-morpholinyl)-3-oxopropyl)-1,3-oxazol-2-yl)-6,7-dihydro-5H-indolo[2,1-a][2]benzazepine-10-carboxylic acid (Peak2-Chiral Isomer B) (100 mg, 0.17 mMol) was dissolved in 1.9 ml of anhydrous THF and carbonyldiimidazole (37.1 mg, 0.23 mMol) added. The reaction was stirred under a nitrogen atmosphere at room temperature for 1 hr and heated at reflux for 1 hr under nitrogen. The reaction was cooled under nitrogen and dimethyl sulfamide (145 mg, 1.17 mMol) and DBU (27.5 uL, 0.18 mMol) added to the reaction. The reaction was heated to 50 C under a nitrogen atmosphere for 4 hrs, then cooled to room temperature and analyzed by HPLC for progress. The reaction was heated for an additional 2.5 hrs at 50 C and again monitored by HPLC. Dimethyl sulfamide (100 mg) and DBU (27 uL) were added to the reaction and the reaction heated to reflux for 3 hrs under nitrogen. Heat was removed and the reaction cooled to room temperature and stirred overnight. The reaction was partitioned between ethyl acetate and 1N aqueous hydrochloric acid and the aqueous phase extracted with ethyl acetate. The organic phases were combined and washed sequentially with 1N aqueous hydrochloric acid, brine then dried over magnesium sulfate. Removal of volatiles in vacuuo left 209 mg of crude product which was purified by reverse phase HPLC under the following conditions: Shimadzu prep. HPLC using Discovery VP software: % A=10% methanol, 90% water, 0.1% TFA; % B=90% methanol, 10% water, 0.1% TFA; Initial % B=50; Final % B=100; Gradient=15 min; Runtime=15 min; Flow rate=45 ml/min; Column=Waters Sunfire 30 mm×100 mm; Peak collection 8.2 min to 9.1 min.; The title compound was isolated as a colorless solid, 71.2 mg (60%). 1H NMR (500 MHz, CHLOROFORM-D) δ ppm 1.25 (q, J=12.82 Hz, 1.2 H) 1.31-1.53 (m, 2.1 H) 1.58-1.85 (m, 3.2 H) 1.86-2.12 (m, 4.2 H) 2.54-2.76 (m, 2.1 H) 2.81-2.99 (m, 3.3 H) 2.99-3.12(m, 7.3 H) 3.14-3.24(m, 1 H) 3.34-3.61 (m, 3.1 H) 3.60-3.73 (m, 5.3H) 3.72-3.82 (m, 0.9 H) 3.84 (s, 0.6 H) 3.90 (s, 2.5 H) 4.02 (dd, J=14.95, 6.10 Hz, 0.9 H) 4.77-4.92 (m, 1.3 H) 6.78-6.87 (m, 1 H) 6.88-7.05 (m, 2 H) 7.30-7.51 (m, 1.2 H) 7.64 (dd, J=8.39, 1.37 Hz, 0.8 H) 7.81-7.95 (m, 1.0 H) 8.01-8.21 (m, 1 H) 8.67 (s, 0.2 H) 9.86 (s, 0.8 H). HPLC analysis: Shimadzu Analytical HPLC using Discovery VP software: % A=10% methanol, 90% water, 0.1% trifluoroacetic acid; % B=90% methanol, 10% water, 0.1% trifluoroacetic acid; Initial % B=50; Final % B=100; Gradient=5 min; Runtime=6 min; Flow rate=5 ml/min; Wavelength=220 nm; Column=Phenomenex Luna 3.0 mm×50 mm S10. Retention Time=3.03 min, purity 99%. Flow injection Mass Spectrometry: MS m/z 704(MH+), 726(M+Na)+, m/z 702(M-H)−. Chiral Purity: Column: Chiralacel OJ-H analytical column 4.6 mm×250 mm; Mobile Phase: 12% methanol in carbon dioxide; Temp: 35° C.; Flow rate: 2.0 ml/min for 40 min; UV monitoring=213 nm; Injection: 5 uL of approximately 1 mg/mL solution in ethanol; Retention time: 32.5 min, purity=100% EE=99.9%.

EXAMPLE 54

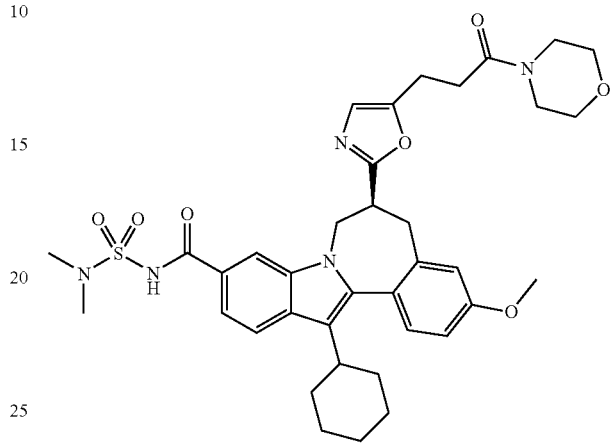

13-cyclohexyl-N-((dimethylamino)sulfonyl)-3-methoxy-6-(5-(3-(4-morpholinyl)-3-oxopropyl)-1,3-oxazol-2-yl)-6,7-dihydro-5H-indolo[2,1-a][2]benzazepine-10-carboxamide (Isomer A). Same procedure used for preparation of above enantiomer except 13-cyclohexyl-3-methoxy-6-(5-(3-(4-morpholinyl)-3-oxopropyl)-1,3-oxazol-2-yl)-6,7-dihydro-5H-indolo[2,1-a][2]benzazepine-10-carboxylic acid (Peak1-Chiral Isomer A) was used as starting material. HPLC analysis: Shimadzu Analytical HPLC using Discovery VP software: % A=10% methanol, 90% water, 0.1% trifluoroacetic acid; % B=90% methanol, 10% water, 0.1% trifluoroacetic acid; Initial % B=50; Final % B=100; Gradient=5 min; Runtime=6 min; Flow rate=5 ml/min; Wavelength=220 nm; Column=Phenomenex Luna 3.0 mm×50 mm S10. Retention Time=3.03 min, purity 99%; Flow injection Mass Spectrometry: MS m/z 704(MH+), 726(M+Na)+, m/z 702(M-H)−. Chiral Purity: Column: Chiralacel OJ-H analytical column 4.6 mm×250 mm; Mobile Phase: 12% methanol in carbon dioxide; Temp: 35° C.; Flow rate: 2.0 ml/min for 40 min; UV monitoring=213 nm; Injection: 5 uL of approximately 1 mg/mL solution in ethanol. Retention time: 27.1 min, purity=100% EE>99.9%.

EXAMPLE 55

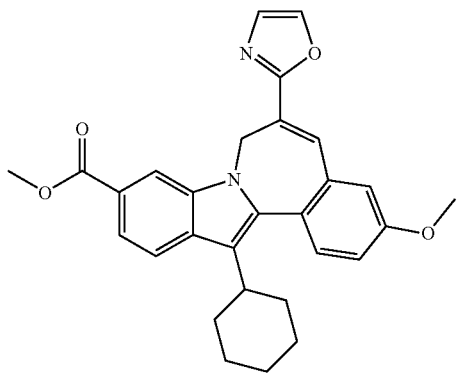

Methyl 13-cyclohexyl-3-methoxy-6-(1,3-oxazol-2-yl)-7H-indolo[2,1-a][2]benzazepine-10-carboxylate. Methyl 13-cyclohexyl-3-(methyloxy)-6-(((2-oxoethyl)amino)carbonyl)-7H-indolo[2,1-a][2]benzazepine-10-carboxylate (410 mg, 0.84 mMol) is dissolved in 10 mL of THF in a microwave reactor tube with stirbar. Burgess Reagent, (602 mg, 2.53 mMol) (methoxycarbonylsulfamoyl)triethylammonium hydroxide, inner salt was added to the reaction vessel. The reaction was placed under nitrogen atmosphere and heated in a microwave for 1 minute at 100 watts. The reaction was monitored by HPLC and additional Burgess Reagent (200 mg, 0.84 mMol) was added to the reaction. The reaction was further heated for minute at 100 watts power. The reaction was partitioned between ethyl acetate and 1N aqueous hydrochloric acid. The aqueous phase was extracted with ethyl acetate. The organic phases were combined and washed sequentially with 1N aqueous hydrochloric acid and brine, dried over magnesium sulfate and volatiles removed in vacuuo to obtain 0.71 g of crude product.

The title compound was purified by silica gel chromatography eluting with a gradient of 0% ethyl acetate in dichloromethane to 15% ethyl acetate in dichloromethane to give 150 mg (38%) as a yellow solid. 1H NMR (500 MHz, CHLOROFORM-d) δ ppm 1.27 (1 H, br. s.), 1.32-1.50 (2 H, m), 1.57 (1 H, br. s.), 1.78 (2 H, d, J=9.77 Hz), 1.95 (1 H, br. s.), 2.07 (3 H, br. s.), 2.71-2.98 (1 H, m), 3.94 (3 H, s), 3.97 (3 H, s), 4.43 (1 H, br. s.), 5.92 (1 H, br. s.), 7.03 (1 H, d, J=2.44 Hz), 7.09 (1 H, dd, J=8.70, 2.59 Hz), 7.29 (1 H, s), 7.55 (1 H, d, J=8.55 Hz), 7.68 (2 H, d, J=10.99 Hz), 7.74 (1 H, dd, J=8.55, 1.22 Hz), 7.86 (1 H, d, J=8.55 Hz), 8.38 (1 H, s). HPLC analysis: Shimadzu Analytical HPLC using Discovery VP software: % A=10% methanol, 90% water, 0.1% trifluoroacetic acid; % B=90% methanol, 10% water, 0.1% trifluoroacetic acid; Initial % B=50; Final % B=100; Gradient=5 min; Runtime=6 min; Flow rate=5 ml/min; Wavelength=220 nm; Column=Phenomenex Luna 3.0 mm×50 mm S10. Retention Time=4.43 min, purity 97%. Flow injection Mass Spectrometry: MS m/z 469(MH$^+$).

EXAMPLE 56

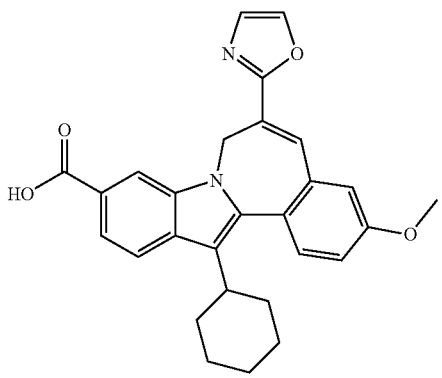

13-Cyclohexyl-3-methoxy-6-(1,3-oxazol-2-yl)-7H-indolo[2,1-a][2]benzazepine-10-carboxylic acid. Methyl 13-cyclohexyl-3-methoxy-6-(1,3-oxazol-2-yl)-7H-indolo[2,1-a][2]benzazepine-10-carboxylate (75.4 mg, 0.16 mMol) was dissolved in 2 mL of THF and potassium trimethylsilanolate (103 mg, 0.80 mMol) added to the reaction. The reaction was stirred at room temperature under a nitrogen atmosphere for 19 hrs. The reaction was partitioned between ethyl acetate and 1N aqueous hydrochloric acid. The organic phase was washed sequentially with 1N aqueous hydrochloric acid and brine, dried over magnesium sulfate and volatiles removed in vacuuo to yield 68 mg (93%) of the title product as a yellow solid. 1H NMR (500 MHz, CHLOROFORM-d) δ ppm 1.18-1.33 (1 H, m), 1.36-1.45 (2 H, m), 1.58 (1 H, br. s.), 1.79 (2 H, d, J=10.07 Hz), 1.96 (1 H, br. s.), 2.08 (3 H, br. s.), 2.88 (1 H, t, J=12.05 Hz), 3.94 (3 H, s), 4.44 (1 H, br. s.), 6.00 (1 H, br. s.), 7.04 (1 H, d, J=2.75 Hz), 7.09 (1 H, dd, J=8.70, 2.59 Hz), 7.31 (1 H, s), 7.56 (1 H, d, J=8.85 Hz), 7.65 (1 H, s), 7.68 (1 H, s), 7.82 (1 H, dd, J=8.55, 1.22 Hz), 7.90 (1 H, d, J=8.55 Hz), 8.54 (1 H, s). HPLC analysis: Shimadzu Analytical HPLC using Discovery VP software: % A=10% methanol, 90% water, 0.1% trifluoroacetic acid; % B=90% methanol, 10% water, 0.1% trifluoroacetic acid; Initial % B=50; Final % B=100; Gradient=5 min; Runtime=6 min; Flow rate=5 ml/min; Wavelength=220 nm; Column=Phenomenex Luna 3.0 mm×50 mm S10. Retention Time=3.83 min, purity 96%. Flow injection Mass Spectrometry: MS m/z 455(MH$^+$), m/z 453(M-H)$^-$.

EXAMPLE 57

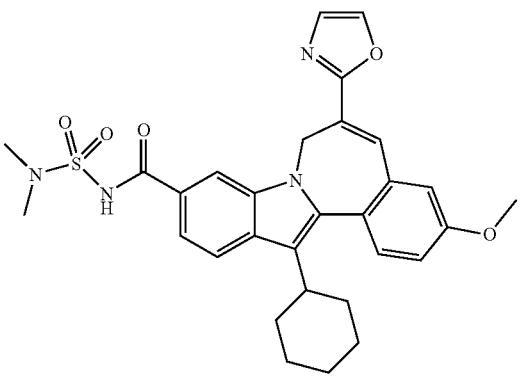

13-Cyclohexyl-N-((dimethylamino)sulfonyl)-3-methoxy-6-(1,3-oxazol-2-yl)-7H-indolo[2,1-a][2]benzazepine-10-carboxamide. 13-Cyclohexyl-3-methoxy-6-(1,3-oxazol-2-yl)-7H-indolo[2,1-a][2]benzazepine-10-carboxylic acid (63 mg, 0.14 mMol) was dissolved in 1.7 mL of THF and carbonyldiimidazole (31 mg, 0.19 mMol) added. The reaction was stirred under a nitrogen atmosphere at room temperature for 1 hr then heated to reflux for 1 hr. The reaction was cooled under nitrogen atmosphere and dimethylsulfamide (91 mg, 0.73 mMol) added followed by DBU (23 uL, 0.15 mMol). The reaction was heated to 50 C under a nitrogen atmosphere for 4 hrs, cooled under nitrogen and stirred at room temperature overnight. The reaction was partitioned between ethyl acetate and 1N aqueous hydrochloric acid. The organic phase washed with brine, dried over magnesium sulfate and volatiles removed in vacuuo to yield 103 mg of a crude product as an amorphous yellow film. The crude product was dissolved in methanol and purified by prep HPLC under the following conditions: Shimadzu prep. HPLC using Discovery VP software; % A=10% methanol, 90% water, 0.1% TFA; % B=90% methanol, 10% water, 0.1% TFA; Initial % B=50; Final % B=100; Gradient=15 min; Runtime=25 min; Flow rate=25 ml/min; Column=Waters Sunfire 19 mm×100 mm; Peak collection=12.16 min to 12.96 min. 1H NMR (500 MHz, CHLOROFORM-d) δ ppm 1.23 (1 H, br. s.), 1.36-1.45 (2 H, m), 1.56 (1 H, br. s.), 1.78 (2 H, d, J=10.07 Hz), 2.00 (2 H, br. s.), 2.07 (2 H, br. s.), 2.78-2.91 (1 H, m), 3.09 (6 H, s), 3.94 (3 H, s), 4.43 (1 H, br. s.), 5.91 (1 H, br. s.), 7.03 (1 H, d, J=2.44 Hz), 7.10 (1 H, dd, J=8.55, 2.75 Hz), 7.50 (1 H, d, J=1.53 Hz), 7.55 (1H, d, J=8.55 Hz), 7.65 (1 H, s), 7.69 (1 H, s), 7.89 (1 H, d, J=8.55 Hz), 8.24 (1 H, s), 8.81 (1 H, br. s.). HPLC analysis: Shimadzu Analytical HPLC using Discovery VP software: % A=10% methanol, 90% water, 0.1% trifluoroacetic acid; % B=90% methanol, 10% water, 0.1% trifluoroacetic acid; Initial % B=50; Final % B=100; Gradient=5 min; Runtime=6 min; Flow rate=5 ml/min; Wavelength=220 nm;

Column=Phenomenex Luna 3.0 mm×50 mm S10. Retention Time=3.65 min, purity 93%; Flow injection Mass Spectrometry: MS m/z 561(MH⁺), m/z 559(M-H)⁻.

EXAMPLE 58

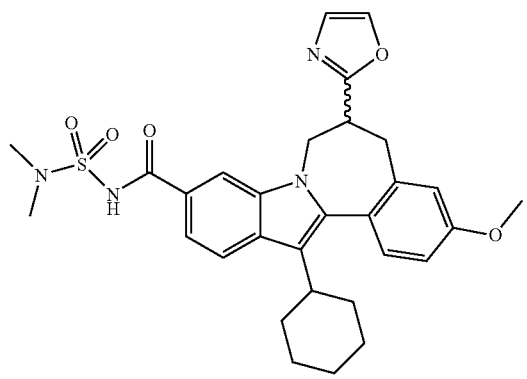

13-Cyclohexyl-N-((dimethylamino)sulfonyl)-3-methoxy-6-(1,3-oxazol-2-yl)-6,7-dihydro-5H-indolo[2,1-a][2]benzazepine-10-carboxamide. 13-Cyclohexyl-N-((dimethylamino)sulfonyl)-3-methoxy-6-(1,3-oxazol-2-yl)-7H-indolo[2,1-a][2]benzazepine-10-carboxamide (45 mg, 0.08 mMol) was dissolved in 3.8 mL of THF and 0.9 mL of methanol added. 10% palladium on carbon (13 mg) was added and the reaction placed under 1 atm (balloon) of hydrogen atmosphere and stirred at room temperature for 18 hrs. The reaction was filtered through a plug of celite and the celite rinsed using dichloromethane. Removal of volatiles from the filtrate in vacuuo yield 47 mg of material which was purified by prep. HPLC under the following conditions: Shimadzu prep. HPLC using Discovery VP software; % A=10% methanol, 90% water, 0.1% TFA; % B=90% methanol, 10% water, 0.1% TFA; Initial % B=50; Final % B=100; Gradient=15 min; Runtime=20 min; Flow rate=25 ml/min; Column=Waters Sunfire 19 mm×100 mm; Peak collection=10.09 min to 10.88 min. Obtained 33.7 mg (75%) of the title compound as a colorless solid. 1H NMR (500 MHz, CHLOROFORM-D) δ ppm 1.20-1.31 (m, 1.1 H) 1.31-1.52 (m, 2.1 H) 1.66 (d, J=13.12 Hz, 1.1 H) 1.78 (d, J=9.16 Hz, 2.0 H) 1.93 (d, J=13.12 Hz, 1.1 H) 1.96-2.09 (m, 2.9 H) 2.82-2.98 (m, 2.2 H) 3.03-3.08 (m, 6.0 H) 3.11-3.19 (m, 1.0 H) 3.73-3.81 (m, 1.0 H) 3.84 (s, 1.3 H) 3.90 (s, 1.8 H) 3.97-4.02 (m, 0.9 H) 4.05 (dd, J=14.95, 5.80 Hz, 0.7 H) 4.75-4.85 (m, 0.4 H) 4.90 (d, J=14.95 Hz, 0.6 H) 6.84 (d, J=2.44 Hz, 0.4 H) 6.94 (dd, J=8.55, 2.44 Hz, 0.5 H) 6.97-7.01 (m, 1.2 H) 7.09-7.17 (m, 1.0 H) 7.32-7.49 (m, 2.0 H) 7.64 (s, 0.6 H) 7.69 (s, 0.4 H) 7.78-7.87 (m, 1.2 H) 7.90 (d, J=8.55 Hz, 0.4 H) 8.02 (s, 0.4 H) 8.42 (s, 0.5 H) 8.59 (s, 0.4H). HPLC analysis: Shimadzu Analytical HPLC using Discovery VP software: % A=10% methanol, 90% water, 0.1% trifluoroacetic acid; % B=90% methanol, 10% water, 0.1% trifluoroacetic acid; Initial % B=50; Final % B=100; Gradient=5 min; Runtime=6 min; Flow rate=5 ml/min; Wavelength=220 nm; Column=Phenomenex Luna 3.0 mm×50 mm S10. Retention Time=3.02 min, purity 99%; Flow injection Mass Spectrometry: MS m/z 563(MH⁺), m/z 561(M-H)⁻.

We claim:
1. A compound of formula I

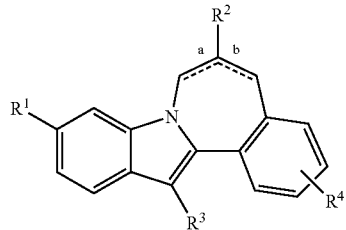

wherein:
R¹ is CO₂R⁵ or CONR⁶R⁷;
R² is furanyl, pyrrolyl, thienyl, pyrazolyl, oxazolyl, thiazolyl, isoxazolyl, isothiazolyl, oxadiazolyl, triazolyl, or tetrazolyl, and is substituted with 0-2 substituents selected from oxo, amino, alkylamino, dialkylamino, alkyl, (cycloalkyl)alkyl, hydroxyalkyl, (tetrahydrofuranyl)alkyl, (tetrahydropyranyl)alkyl, (CO₂R⁵)alkyl, (CON(R⁵)₂)alkyl, (COR⁹)alkyl, (alkylsulfonyl)alkyl, and ((R⁹)alkyl)CON(R⁵);
R³ is C₅₋₇cycloalkyl;
R⁴ is hydrogen, halo, hydroxy, alkyl, or alkoxy;
R⁵ is hydrogen, alkyl, or cycloalkyl;
R⁶ is hydrogen, alkyl, cycloalkyl, alkoxy, or SO₂R⁸;
R⁷ is hydrogen, alkyl, or cycloalkyl;
or NR⁶R⁷ taken together is pyrrolidinyl, piperidinyl, piperazinyl, N-alkylpiperazinyl, homomorpholinyl, homopiperidinyl, morpholinyl, or thiomorpholinyl;
R⁸ is alkyl, haloalkyl, cycloalkyl, amino, alkylamino, dialkylamino, or phenyl;
or R⁸ is pyrrolidinyl, piperidinyl, piperazinyl, N-alkylpiperazinyl, homomorpholinyl, homopiperidinyl, morpholinyl, or thiomorpholinyl;
R⁹ is pyrrolidinyl, piperidinyl, piperazinyl, N-alkylpiperazinyl, homomorpholinyl, homopiperidinyl, morpholinyl, or thiomorpholinyl; and
(a) is a single bond or a double bond, (b) is a single bond or a double bond, provided that at least one of (a) and (b) is a single bond;
or a pharmaceutically acceptable salt thereof.
2. A compound of claim 1 where R¹ is CONR⁶R⁷; R⁶ is SO₂R⁸; and R⁷ is hydrogen.
3. A compound of claim 1 where R³ is cyclohexyl.
4. A compound of claim 1 where R⁴ is hydrogen.
5. A compound of claim 1 where R⁴ is methoxy.
6. A compound of claim 1 selected from the group consisting of
13-cyclohexyl-6-(1H-tetrazol-5-yl)-7H-indolo[2,1-a][2]benzazepine-10-carboxylic acid, methyl ester;
13-cyclohexyl-6-(2-ethyl-2H-tetrazol-5-yl)-5H-indolo[2,1-a][2]benzazepine-10-carboxylic acid;
13-cyclohexyl-6-(2-ethyl-2H-tetrazol-5-yl)-7H-indolo[2,1-a][2]benzazepine-10-carboxylic acid;
13-cyclohexyl-N-[(dimethylamino)sulfonyl]-6-[-(2-ethyl-]-2H-tetrazol-5-yl-])-7H-indolo[2,1-a][2]benzazepine-10-carboxamide;
13-cyclohexyl-6-[2-(2-hydroxyethyl)-2H-tetrazol-5-yl]-7H-indolo[2,1-a][2]benzazepine-10-carboxylic acid;
13-cyclohexyl-6-[2-(cyclopropylmethyl)-2H-tetrazol-5-yl]-7H-indolo[2,1-a][2]benzazepine-10-carboxylic acid;

13-cyclohexyl-6-[2-(cyclopropylmethyl)-2H-tetrazol-5-yl]-5H-indolo[2,1-a][2]benzazepine-10-carboxylic acid;

13-cyclohexyl-6-[2-[(tetrahydro-2-furanyl)methyl]-2H-tetrazol-5-yl]-5H-indolo[2,1-a][2]benzazepine-10-carboxylic acid;

13-cyclohexyl-6-[2-[(tetrahydro-2-furanyl)methyl]-2H-tetrazol-5-yl]-7H-indolo[2,1-a][2]benzazepine-10-carboxylic acid;

13-cyclohexyl-6-[1-[(tetrahydro-2-furanyl)methyl]-1H-tetrazol-5-yl]-7H-indolo[2,1-a][2]benzazepine-10-carboxylic acid;

13-cyclohexyl-6-[2-[(tetrahydro-2H-pyran-4-yl)methyl]-2H-tetrazol-5-yl]-7H-indolo[2,1-a][2]benzazepine-10-carboxylic acid;

13-cyclohexyl-6-[2-[(tetrahydro-2H-pyran-4-yl)methyl]-2H-tetrazol-5-yl]-5H-indolo[2,1-a][2]benzazepine-10-carboxylic acid;

13-cyclohexyl-6-[1-[(tetrahydro-2H-pyran-4-yl)methyl]-1H-tetrazol-5-yl]-7H-indolo[2,1-a][2]benzazepine-10-carboxylic acid;

13-cyclohexyl-6-[1-[(tetrahydro-2H-pyran-4-yl)methyl]-1 H-tetrazol-5-yl]-5H-indolo[2,1-a][2]benzazepine-10-carboxylic acid;

13-cyclohexyl-N-[(dimethylamino)sulfonyl]-6-[2-[(tetrahydro-2H-pyran-4-yl)methyl]-2H-tetrazol-5-yl]-7H-indolo[2,1-a][2]benzazepine-10-carboxamide;

13-cyclohexyl-3-methoxy-6-[2-[(tetrahydro-2H-pyran-4-yl)methyl]-2H-tetrazol-5-yl]-7H-indolo[2,1-a][2]benzazepine-10-carboxylic acid;

13-cyclohexyl-N-[(dimethylamino)sulfonyl]-3-methoxy-6-[2-[(tetrahydro-2H-pyran-4-yl)methyl]-2H-tetrazol-5-yl]-7H-indolo[2,1-a][2]benzazepine-10-carboxamide;

13-cyclohexyl-6-(4,5-dihydro-5-oxo-1,3,4-oxadiazol-2-yl)-7H-indolo[2,1-a][2]benzazepine-10-carboxylic acid, methyl ester;

13-cyclohexyl-6-(4,5-dihydro-5-oxo-1,3,4-oxadiazol-2-yl)-7H-indolo[2,1-a][2]benzazepine-10-carboxylic acid;

13-cyclohexyl-6-[4,5-dihydro-5-oxo-4-[(tetrahydro-2H-pyran-4-yl)methyl]-1,3,4-oxadiazol-2-yl]-7H-indolo[2,1-a][2]benzazepine-10-carboxylic acid, methyl ester;

13-cyclohexyl-6-[4,5-dihydro-5-oxo-4-[(tetrahydro-2H-pyran-4-yl)methyl]-1,3,4-oxadiazol-2-yl]-7H-indolo[2,1-a][2]benzazepine-10-carboxylic acid;

13-cyclohexyl-6-[3-[(tetrahydro-2H-pyran-4-yl)methyl]-1H-1,2,4-triazol-5-yl]-7H-indolo[2,1-a][2]benzazepine-10-carboxylic acid;

13-cyclohexyl-6-(3-methyl-1,2,4-oxadiazol-5-yl)-7H-ndolo[2,1-a][2]benzazepine-10-carboxylic acid, methyl ester;

13-cyclohexyl-6-(3-methyl-1,2,4-oxadiazol-5-yl)-7H-indolo[2,1-a][2]benzazepine-10-carboxylic acid;

13-cyclohexyl-N-[(dimethylamino)sulfonyl]-6-(3-methyl-1,2,4-oxadiazol-5-yl)-7H-indolo[2,1-a][2]benzazepine-10-carboxamide;

13-cyclohexyl-6-[3-[(methylsulfonyl)methyl]-1,2,4-oxadiazol-5-yl]-7H-indolo[2,1-a][2]benzazepine-10-carboxylic acid, methyl ester;

13-cyclohexyl-6-[3-[(methylsulfonyl)methyl]-1,2,4-oxadiazol-5-yl]-7H-indolo[2,1-a][2]benzazepine-10-carboxylic acid;

13-cyclohexyl-N-[(dimethylamino)sulfonyl]-6-[3-[(methylsulfonyl)methyl]-1,2,4-oxadiazol-5-yl]-7H-indolo[2,1-a][2]benzazepine-10-carboxamide;

6-(5-amino-1,3,4-oxadiazol-2-yl)-13-cyclohexyl-7H-indolo[2,1-a][2]benzazepine-10-carboxylic acid, methyl ester;

6-(5-amino-1,3,4-oxadiazol-2-yl)-13-cyclohexyl-7H-indolo[2,1-a][2]benzazepine-10-carboxylic acid;

13-cyclohexyl-6-[5-[(4-morpholinylacetyl)amino]-1,3,4-oxadiazol-2-yl]-7H-indolo[2,1-a][2]benzazepine-10-carboxylic acid, methyl ester;

13-cyclohexyl-6-[5-[(4-morpholinylacetyl)amino]-1,3,4-oxadiazol-2-yl]-7H-indolo[2,1-a][2]benzazepine-10-carboxylic acid;

13-cyclohexyl-6-[5-(3-methoxy-3-oxopropyl)-2-oxazolyl]-7H-indolo[2,1-a][2]benzazepine-10-carboxylic acid, methyl ester;

13-cyclohexyl-6-[5-[3-(4-morpholinyl)-3-oxopropyl]-2-oxazolyl]-7H-indolo[2,1-a][2]benzazepine-10-carboxylic acid, methyl ester;

13-cyclohexyl-6-[5-[3-(4-morpholinyl)-3-oxopropyl]-2-oxazolyl]-7H-indolo[2,1-a][2]benzazepine-10-carboxylic acid;

13-cyclohexyl-N-[(dimethylamino)sulfonyl]-6-[5-[3-(4-morpholinyl)-3-oxopropyl]-2-oxazolyl]-7H-indolo[2,1-a][2]benzazepine-10-carboxamide;

13-cyclohexyl-N-[(dimethylamino)sulfonyl]-6,7-dihydro-6-[5-[3-(4-morpholinyl)-3-oxopropyl]-2-oxazolyl]-5H-indolo[2,1-a][2]benzazepine-10-carboxamide;

13-cyclohexyl-6-[5-[(tetrahydro-2H-pyran-4-yl)methyl]-1,3,4-oxadiazol-2-yl]-7H-indolo[2,1-a][2]benzazepine-10-carboxylic acid, methyl ester;

13-cyclohexyl-6-[5-[(tetrahydro-2H-pyran-4-yl)methyl]-1H-1,2,4-triazol-3-yl]-7H-indolo[2,1-a][2]benzazepine-10-carboxylic acid, methyl ester;

13-cyclohexyl-6-[1-methyl-5-[(tetrahydro-2H-pyran-4-yl)methyl]-1H-1,2,4-triazol-3-yl]-7H-indolo[2,1-a][2]benzazepine-10-carboxylic acid, methyl ester;

13-cyclohexyl-6-[1-methyl-5-[(tetrahydro-2H-pyran-4-yl)methyl]-1H-1,2,4-triazol-3-yl]-7H-indolo[2,1-a][2]benzazepine-10-carboxylic acid;

13-cyclohexyl-N-[(dimethylamino)sulfonyl]-6-[1-methyl-5-[(tetrahydro-2H-pyran-4-yl)methyl]-1H-1,2,4-triazol-3-yl]-7H-indolo[2,1-a][2]benzazepine-10-carboxamide;

13-cyclohexyl-6-[5-[(tetrahydro-2H-pyran-4-yl)methyl]-1,3,4-oxadiazol-2-yl]-7H-indolo[2,1-a][2]benzazepine-10-carboxylic acid;

13-Cyclohexyl-6-(furan-3-yl)-7H-indolo[2,1-a][2]benzazepine-10-carboxylic Acid;

Methyl 13-cyclohexyl-3-methoxy-6-(5-(3-methoxy-3-oxopropyl)-1,3-oxazol-2-yl)-7H-indolo[2,1-a][2]benzazepine-10-carboxylate;

3-(2-(13-Cyclohexyl-3-methoxy-10-(methoxycarbonyl)-7H-indolo[2,1-a][2]benzazepin-6-yl)-1,3-oxazol-5-yl)propanoic acid;

Methyl 13-cyclohexyl-3-methoxy-6-(5-(3-(4-morpholinyl)-3-oxopropyl)-1,3-oxazol-2-yl)-7H-indolo[2, 1-a][2]benzazepine-10-carboxylate;

Methyl 13-cyclohexyl-3-methoxy-6-(5-(3-(4-morpholinyl)-3-oxopropyl)-1,3-oxazol-2-yl)-6,7-dihydro-5H-indolo[2,1-a][2]benzazepine-10-carboxylate;

13-Cyclohexyl-3-methoxy-6-(5-(3-(4-morpholinyl)-3-oxopropyl)-1,3-oxazol-2-yl)-6,7-dihydro-5H-indolo[2,1-a][2]benzazepine-10-carboxylic acid;

13-Cyclohexyl-3-methoxy-6-(5-(3-(4-morpholinyl)-3-oxopropyl)-1,3-oxazol-2-yl)-6,7-dihydro-5H-indolo[2,1-a][2]benzazepine-10-carboxylic acid. (Isomer A);

13-Cyclohexyl-3-methoxy-6-(5-(3-(4-morpholinyl)-3-oxopropyl)-1,3-oxazol-2-yl)-6,7-dihydro-5H-indolo[2,1-a][2]benzazepine-10-carboxylic acid (Isomer B);

13-Cyclohexyl-N-((dimethylamino)sulfonyl)-3-methoxy-6-(5-(3-(4-morpholinyl)-3-oxopropyl)-1,3-oxazol-2-yl)-6,7-dihydro-5H-indolo[2,1-a][2]benzazepine-10-carboxamide (Isomer B);

13-cyclohexyl-N-((dimethylamino)sulfonyl)-3-methoxy-6-(5-(3-(4-morpholinyl)-3-oxopropyl)-1,3-oxazol-2-yl)-6,7-dihydro-5H-indolo[2,1-a][2]benzazepine-10-carboxamide (Isomer A);

Methyl 13-cyclohexyl-3-methoxy-6-(1,3-oxazol-2-yl)-7H-indolo[2,1-a][2]benzazepine-10-carboxylate;

13-Cyclohexyl-3-methoxy-6-(1,3-oxazol-2-yl)-7H-indolo[2,1-a][2]benzazepine-10-carboxylic acid;

13-Cyclohexyl-N-((dimethylamino)sulfonyl)-3-methoxy-6-(1,3-oxazol-2-yl)-7H-indolo[2,1-a][2]benzazepine-10-carboxamide; and 13-Cyclohexyl-N-((dimethylamino)sulfonyl)-3-methoxy-6-(1,3-oxazol-2-yl)-6,7-dihydro-5H-indolo[2,1-a][2]benzazepine-10-carboxamide;

or a pharmaceutically acceptable salt thereof.

7. A composition comprising a compound of claim 1 or a pharmaceutically acceptable salt thereof and a pharmaceutically acceptable carrier.

8. A method of treating hepatitis C infection comprising administering a therapeutically effective amount of a compound of claim 1 to a patient.

* * * * *